US012162907B2

(12) United States Patent
Perugi et al.

(10) Patent No.: US 12,162,907 B2
(45) Date of Patent: Dec. 10, 2024

(54) SUBUNIT VACCINE FOR TREATMENT OR PREVENTION OF A RESPIRATORY TRACT INFECTION

(71) Applicant: Valneva SE, Saint-Herblain (FR)

(72) Inventors: Fabien Perugi, Nantes (FR); Klaus Schwamborn, Nantes (FR); Wolfgang Schüler, Vienna (AT); Urban Lundberg, Pressbaum (AT); Andreas Meinke, Pressbaum (AT)

(73) Assignee: Valneva SE, Nantes (FR)

( * ) Notice: Subject to any disclaimer, the term of this patent is extended or adjusted under 35 U.S.C. 154(b) by 447 days.

(21) Appl. No.: 17/606,811

(22) PCT Filed: May 19, 2020

(86) PCT No.: PCT/EP2020/063973
§ 371 (c)(1),
(2) Date: Oct. 27, 2021

(87) PCT Pub. No.: WO2020/234300
PCT Pub. Date: Nov. 26, 2020

(65) Prior Publication Data

US 2022/0185847 A1 Jun. 16, 2022

(30) Foreign Application Priority Data

May 20, 2019 (EP) .................................... 19175413

(51) Int. Cl.
*C07K 14/005* (2006.01)
*A61P 31/14* (2006.01)
*A61K 39/00* (2006.01)

(52) U.S. Cl.
CPC ............ *C07K 14/005* (2013.01); *A61P 31/14* (2018.01); *A61K 39/00* (2013.01)

(58) Field of Classification Search
None
See application file for complete search history.

(56) References Cited

U.S. PATENT DOCUMENTS 5,547,871 A 8/1996 Black et al.
8,715,922 B2 * 5/2014 De Jong ................ C12Q 1/701 435/7.1

(Continued)

FOREIGN PATENT DOCUMENTS

EA 023397 B1 5/2016
RU 2016111978 A 11/2017

(Continued)

OTHER PUBLICATIONS

[No Author Listed], GenBank Accession No. AGU13651.1. immunoglobulin heavy chain variable region MPE8, partial [*Homo sapiens*]. Sep. 19, 2013. 2 pages.

(Continued)

*Primary Examiner* — Agnieszka Boesen
(74) *Attorney, Agent, or Firm* — Wolf, Greenfield & Sacks, P.C.

(57) ABSTRACT

The present invention relates to modified metapneumovirus (hMPV) F proteins, stabilized in the pre-fusion conformation. It also relates to immunogenic compositions (vaccines) comprising these proteins for preventing and/or treating human subjects against respiratory tract infections.

20 Claims, 19 Drawing Sheets

Specification includes a Sequence Listing.

(56) References Cited

U.S. PATENT DOCUMENTS

| | | | | |
|---|---|---|---|---|
| 10,420,834 | B2 * | 9/2019 | Kwong | ................ C07K 14/135 |
| 2016/0220662 | A1 | 8/2016 | Bueno Ramirez et al. | |
| 2018/0008697 | A1 | 1/2018 | Kwong et al. | |
| 2018/0326045 | A1 | 11/2018 | Ciaramella et al. | |
| 2024/0067681 | A1 | 2/2024 | Perugi et al. | |
| 2024/0181034 | A1 | 6/2024 | Lundberg et al. | |

FOREIGN PATENT DOCUMENTS

| | | | |
|---|---|---|---|
| WO | WO 1996/002555 | A1 | 2/1996 |
| WO | WO 2001/024822 | A2 | 4/2001 |
| WO | WO 2001/054720 | A1 | 8/2001 |
| WO | WO 2001/093903 | A1 | 12/2001 |
| WO | WO 2001/093905 | A1 | 12/2001 |
| WO | WO 2002/013857 | A2 | 2/2002 |
| WO | WO 2002/032451 | A1 | 4/2002 |
| WO | WO 2002/095027 | A2 | 11/2002 |
| WO | WO 2003/047602 | A1 | 6/2003 |
| WO | WO 2004/084938 | A1 | 10/2004 |
| WO | WO 2004/096993 | A2 | 11/2004 |
| WO | WO 2010/149743 | A2 | 12/2010 |
| WO | WO 2011/050168 | A2 | 4/2011 |
| WO | WO 2011/150264 | A2 | 12/2011 |
| WO | WO 2013/083726 | A1 | 6/2013 |
| WO | WO 2016/103238 | A1 | 6/2016 |
| WO | WO 2018/005558 | A1 | 1/2018 |
| WO | WO 2019/092002 | A1 | 5/2019 |
| WO | WO 2020/234300 | A1 | 11/2020 |

OTHER PUBLICATIONS

[No Author Listed], GenBank Accession No. AGU13652.1. immunoglobulin light chain variable region MPE8, partial [*Homo sapiens*]. Sep. 19, 2013. 2 pages.

[No Author Listed], Ingredients of Vaccines—Fact Sheet. Centers for Disease Control and Prevention, United States Department of Health and Human Services. As available Apr. 9, 2021. 2 pages.

[No Author Listed], UniProtKB/Swiss-Prot; Accession No. Q6WB99. 1; RecName: Full=Matrix protein; AltName: Full=M protein. Apr. 7, 2021. 2 pages.

Aerts et al., Adjuvant effect of the human metapneumovirus (HMPV) matrix protein in HMPV subunit vaccines. J Gen Virol. Apr. 2015;96(Pt 4):767-774. doi: 10.1099/vir.0.000031. Epub Dec. 17, 2014.

Altschul et al., Basic local alignment search tool. J Mol Biol. Oct. 5, 1990;215(3):403-10. doi: 10.1016/S0022-2836(05)80360-2.

Altschul et al., Gapped BLAST and PSI-BLAST: a new generation of protein database search programs. Nucleic Acids Res. Sep. 1, 1997;25(17):3389-402. doi: 10.1093/nar/25.17.3389.

Anishkin et al., Symmetry-Restrained Molecular Dynamics Simulations Improve Homology Models of Potassium Channels. Proteins. Mar. 2010;78(4):932-49. doi: 10.1002/prot.22618. Author manuscript, 27 pages.

Battles et al., Structure and immunogenicity of pre-fusion-stabilized human metapneumovirus F glycoprotein. Nat Commun. Nov. 16, 2017;8(1):1528. doi: 10.1038/s41467-017-01708-9.

Berendsen et al., Gromacs: A message-passing parallel molecular dynamics implementation. Computer Physics Communications. 1995;91:43-56.

Biacchesi et al., Modification of the trypsin-dependent cleavage activation site of the human metapneumovirus fusion protein to be trypsin independent does not increase replication or spread in rodents or nonhuman primates. J Virol. Jun. 2006;80(12):5798-806. doi: 10.1128/JVI.00294-06.

Cluff, Monophosphoryl lipid A (MPL) as an adjuvant for anti-cancer vaccines: clinical results. Adv Exp Med Biol. 2010:667:111-23. doi: 10.1007/978-1-4419-1603-7_10.

Coler et al., Development and characterization of synthetic glucopyranosyl lipid adjuvant system as a vaccine adjuvant. PLoS One. Jan. 26, 2011;6(1):e16333. doi: 10.1371/journal.pone.0016333.

Corpet, Multiple sequence alignment with hierarchical clustering. Nucleic Acids Res. Nov. 25, 1988;16(22):10881-90. doi: 10.1093/nar/16.22.10881.

Corti et al., Cross-neutralization of four paramyxoviruses by a human monoclonal antibody. Nature. Sep. 19, 2013;501(7467):439-43. doi: 10.1038/nature12442. Epub Aug. 18, 2013.

Cox et al., The human metapneumovirus fusion protein mediates entry via an interaction with RGD-binding integrins. J Virol. Nov. 2012;86(22):12148-60. doi: 10.1128/JVI.01133-12. Epub Aug. 29, 2012.

Devereaux et al., A comprehensive set of sequence analysis programs for the VAX. Nucleic Acids Res. Jan. 11, 1984;12(1 Pt 1):387-95. doi: 10.1093/nar/12.1part1.387.

Dickinson et al., Dissociation of *Escherichia coli* heat-labile enterotoxin adjuvanticity from ADP-ribosyltransferase activity. Infect Immun. May 1995;63(5):1617-23. doi: 10.1128/iai.63.5.1617-1623.1995.

Falsey et al., Humoral immunity to human metapneumovirus infection in adults. Vaccine. Feb. 10, 2010;28(6):1477-80. doi: 10.1016/j.vaccine.2009.11.063. Epub Dec. 8, 2009.

Feng et al., Progressive sequence alignment as a prerequisite to correct phylogenetic trees. J Mol Evol. 1987;25(4):351-60. doi: 10.1007/BF02603120.

Giudice et al., Correlates of adjuvanticity: A review on adjuvants in licensed vaccines. Semin Immunol. Oct. 2018:39:14-21. doi: 10.1016/j.smim.2018.05.001. Epub May 23, 2018.

Harbury et al., A switch between two-, three-, and four-stranded coiled coils in GCN4 leucine zipper mutants. Science. Nov. 26, 1993;262(5138):1401-7. doi: 10.1126/science.8248779.

Henikoff et al., Amino acid substitution matrices from protein blocks. Proc Natl Acad Sci U S A. Nov. 15, 1992;89(22):10915-9. doi: 10.1073/pnas.89.22.10915.

Herfst et al., Immunization of Syrian golden hamsters with F subunit vaccine of human metapneumovirus induces protection against challenge with homologous or heterologous strains. J Gen Virol. Oct. 2007;88(Pt 10):2702-2709. doi: 10.1099/vir.0.83084-0.

Hess et al., GROMACS 4: Algorithms for Highly Efficient, Load-Balanced, and Scalable Molecular Simulation. J Chem Theory Comput. Mar. 2008;4(3):435-47. doi: 10.1021/ct700301q.

Higgins et al., CLUSTAL: a package for performing multiple sequence alignment on a microcomputer. Gene. Dec. 15, 1988;73(1):237-44. doi: 10.1016/0378-1119(88)90330-7.

Higgins et al., Fast and sensitive multiple sequence alignments on a microcomputer. Comput Appl Biosci. Apr. 1989;5(2):151-3. doi: 10.1093/bioinformatics/5.2.151.

Hombach et al., Report on a WHO consultation on immunological endpoints for evaluation of new Japanese encephalitis vaccines, WHO, Geneva, Sep. 2-3, 2004. Vaccine. Nov. 1, 2005;23(45):5205-11. doi: 10.1016/j.vaccine.2005.07.002. Epub Jul. 18, 2005.

Huang et al., Antibody Epitopes of Pneumovirus Fusion Proteins. Front Immunol. Nov. 29, 2019:10:2778. doi: 10.3389/fimmu.2019.02778. eCollection 2019.

Huang et al., Parallelization of a local similarity algorithm. Comput Appl Biosci. Apr. 1992;8(2):155-65. doi: 10.1093/bioinformatics/8.2.155.

Kahn, Epidemiology of human metapneumovirus. Clin Microbiol Rev. Jul. 2006;19(3):546-57. doi: 10.1128/CMR.00014-06.

Kolli et al., T lymphocytes contribute to antiviral immunity and pathogenesis in experimental human metapneumovirus infection. J Virol. Sep. 2008;82(17):8560-9. doi: 10.1128/JVI.00699-08. Epub Jun. 18, 2008.

Krarup et al., A highly stable prefusion RSV F vaccine derived from structural analysis of the fusion mechanism. Nat Commun. Sep. 3, 2015:6:8143. doi: 10.1038/ncomms9143.

Mackerell et al., All-atom empirical potential for molecular modeling and dynamics studies of proteins. J Phys Chem B. Apr. 30, 1998;102(18):3586-616. doi: 10.1021/jp973084f.

Más et al., Engineering, Structure and Immunogenicity of the Human Metapneumovirus F Protein in the Postfusion Conformation. PLoS Pathog. Sep. 9, 2016;12(9):e1005859. doi: 10.1371/journal.ppat.1005859. eCollection Sep. 2016.

Melero et al., The Pneumovirinae fusion (F) protein: A common target for vaccines and antivirals. Virus Res. Nov. 2, 2015;209:128-35. doi: 10.1016/j.virusres.2015.02.024. Epub Mar. 1, 2015.

(56) References Cited

OTHER PUBLICATIONS

Needleman et al., A general method applicable to the search for similarities in the amino acid sequence of two proteins. J Mol Biol. Mar. 1970;48(3):443-53. doi: 10.1016/0022-2836(70)90057-4.
Ngwuta et al., Prefusion F-specific antibodies determine the magnitude of RSV neutralizing activity in human sera. Sci Transl Med. Oct. 14, 2015;7(309):309ra162. doi: 10.1126/scitranslmed.aac4241.
Olafsdottir et al., IC31, a two-component novel adjuvant mixed with a conjugate vaccine enhances protective immunity against pneumococcal disease in neonatal mice. Scand J Immunol. Mar. 2009;69(3):194-202. doi: 10.1111/j.1365-3083.2008.02225.x.
Ott et al., MF59. Design and Evaluation of a Safe and Potent Adjuvant for Human Vaccines. Pharm Biotechnol. 1995:6:277-96. doi: 10.1007/978-1-4615-1823-5_10.
Ott et al., The Adjuvant MF59: A 10-Year Perspective. Methods in Molecular Medicine, Vaccine Adjuvants. 2000;42:211-28.
Pearson et al., Improved tools for biological sequence comparison. Proc Natl Acad Sci U S A. Apr. 1988;85(8):2444-8. doi: 10.1073/pnas.85.8.2444.
Pearson, Using the FASTA program to search protein and DNA sequence databases. Methods Mol Biol. 1994:24:307-31. doi: 10.1385/0-89603-246-9:307.
Phillips et al., Scalable molecular dynamics with NAMD. J Comput Chem. Dec. 2005;26(16):1781-802. doi: 10.1002/jcc.20289. Author manuscript, 43 pages.
Pilaev et al., Evaluation of pre- and post-fusion Human metapneumovirus F proteins as subunit vaccine candidates in mice. Vaccine. Feb. 24, 2020;38(9):2122-2127. doi: 10.1016/j.vaccine.2020.01.047. Epub Jan. 29, 2020.
Rahman et al., Genetic characterization of human metapneumovirus identified through community and facility-based surveillance of infants in Dhaka, Bangladesh. J Med Virol. 2018;91(4):549-554. doi: 10.1002/jmv.25351. Epub Nov. 13, 2018.
Rodriguez et al., Generation of monoclonal antibodies specific of the postfusion conformation of the Pneumovirinae fusion (F) protein. J Virol Methods. Nov. 2015:224:1-8. doi: 10.1016/j.jviromet.2015.08.002. Epub Aug. 12, 2015.
Rossey et al., Clinical Potential of Prefusion RSV F-specific Antibodies. Trends Microbiol. Mar. 2018;26(3):209-219. doi: 10.1016/j.tim.2017.09.009. Epub Oct. 17, 2017.
Russell et al., Studies with cross-linking reagents on the oligomeric form of the paramyxovirus fusion protein. Virology. Feb. 15, 1994;199(1):160-8. doi: 10.1006/viro.1994.1108.
Ryder et al., Soluble recombinant human metapneumovirus G protein is immunogenic but not protective. Vaccine. Jun. 7, 2010;28(25):4145-52. doi: 10.1016/j.vaccine.2010.04.007. Epub Apr. 22, 2010. Author manuscript, 17 pages.
Sarkar et al., Selection of adjuvants for vaccines targeting specific pathogens. Expert Rev Vaccines. May 2019;18(5):505-521. doi: 10.1080/14760584.2019.1604231. Epub Apr. 22, 2019.
Schildgen et al., Human Metapneumovirus: lessons learned over the first decade. Clin Microbiol Rev. Oct. 2011;24(4):734-54. doi: 10.1128/CMR.00015-11.
Schowalter et al., Characterization of human metapneumovirus F protein-promoted membrane fusion: critical roles for proteolytic processing and low pH. J Virol. Nov. 2006;80(22):10931-41. doi: 10.1128/JVI.01287-06. Epub Sep. 13, 2006.
Shirogane et al., Efficient multiplication of human metapneumovirus in Vero cells expressing the transmembrane serine protease TMPRSS2. J Virol. Sep. 2008;82(17):8942-6. doi: 10.1128/JVI.00676-08. Epub Jun. 18, 2008.
Skeiky et al., A recombinant Leishmania antigen that stimulates human peripheral blood mononuclear cells to express a Th1-type cytokine profile and to produce interleukin 12. J Exp Med. Apr. 1, 1995;181(4):1527-37. doi: 10.1084/jem.181.4.1527.
Skidopoulus et al., Individual contributions of the human metapneumovirus F, G, and SH surface glycoproteins to the induction of neutralizing antibodies and protective immunity. Virology. Feb. 20, 2006;345(2):492-501. doi: 10.1016/j.virol.2005.10.016. Epub Nov. 21, 2005.
Smith et al., Comparison of biosequences. Advances in Applied Mathematics. Dec. 1981;2(4):482-9.
Van Den Hoogen et al., Analysis of the genomic sequence of a human metapneumovirus. Virology. Mar. 30, 2002;295(1):119-32. doi: 10.1006/viro.2001.1355.
Van Den Hoogen et al., Antigenic and genetic variability of human metapneumoviruses. Emerg Infect Dis. Apr. 2004;10(4):658-66. doi: 10.3201/eid1004.030393.
Wen et al., Structure of the human metapneumovirus fusion protein with neutralizing antibody identifies a pneumovirus antigenic site. Nat Struct Mol Biol. Mar. 4, 2012;19(4):461-3. doi: 10.1038/nsmb.2250. Author manuscript, 10 pages.
Williams et al., A recombinant human monoclonal antibody to human metapneumovirus fusion protein that neutralizes virus in vitro and is effective therapeutically in vivo. J Virol. Aug. 2007;81(15):8315-24. doi: 10.1128/JVI.00106-07. Epub May 23, 2007.
Williams et al., The cotton rat (*Sigmodon hispidus*) is a permissive small animal model of human metapneumovirus infection, pathogenesis, and protective immunity. J Virol. Sep. 2005;79(17):10944-51. doi: 10.1128/JVI.79.17.10944-10951.2005.
Yang et al., Genetic diversity and evolution of human metapneumovirus fusion protein over twenty years. Virol J. Sep. 9, 2009:6:138. doi: 10.1186/1743-422X-6-138.
Yin et al., Structure of the parainfluenza virus 5 F protein in its metastable, prefusion conformation. Nature. Jan. 5, 2006;439(7072):38-44. doi: 10.1038/nature04322.
Yin et al., Structure of the uncleaved ectodomain of the paramyxovirus (hPIV3) fusion protein. Proc Natl Acad Sci U S A. Jun. 28, 2005;102(26):9288-93. doi: 10.1073/pnas.0503989102. Epub Jun. 17, 2005.
Yun et al., Trypsin- and low pH-mediated fusogenicity of avian metapneumovirus fusion proteins is determined by residues at positions 100, 101 and 294. Sci Rep. Oct. 26, 2015:5:15584. doi: 10.1038/srep15584.
Zhao et al., Combination therapy targeting toll like receptors 7, 8 and 9 eliminates large established tumors. J Immunother Cancer. May 13, 2014:2:12. doi: 10.1186/2051-1426-2-12. eCollection 2014.

* cited by examiner

A

B

C

D

G

A

B

SEQUENCE LISTING

```
<160> NUMBER OF SEQ ID NOS: 56

<210> SEQ ID NO 1
<211> LENGTH: 539
<212> TYPE: PRT
<213> ORGANISM: Human metapneumovirus

<400> SEQUENCE: 1

Met Ser Trp Lys Val Val Ile Ile Phe Ser Leu Leu Ile Thr Pro Gln
1               5                   10                  15

His Gly Leu Lys Glu Ser Tyr Leu Glu Glu Ser Cys Ser Thr Ile Thr
            20                  25                  30

Glu Gly Tyr Leu Ser Val Leu Arg Thr Gly Trp Tyr Thr Asn Val Phe
        35                  40                  45

Thr Leu Glu Val Gly Asp Val Glu Asn Leu Thr Cys Ala Asp Gly Pro
    50                  55                  60

Ser Leu Ile Lys Thr Glu Leu Asp Leu Thr Lys Ser Ala Leu Arg Glu
65                  70                  75                  80

Leu Arg Thr Val Ser Ala Asp Gln Leu Ala Arg Glu Glu Gln Ile Glu
                85                  90                  95

Asn Pro Arg Gln Ser Arg Phe Val Leu Gly Ala Ile Ala Leu Gly Val
            100                 105                 110

Ala Thr Ala Ala Ala Val Thr Ala Gly Val Ala Ile Ala Lys Thr Ile
        115                 120                 125
```

-continued

```
Arg Leu Glu Ser Glu Val Thr Ala Ile Lys Asn Ala Leu Lys Lys Thr
    130                 135                 140

Asn Glu Ala Val Ser Thr Leu Gly Asn Gly Val Arg Val Leu Ala Thr
145                 150                 155                 160

Ala Val Arg Glu Leu Lys Asp Phe Val Ser Lys Asn Leu Thr Arg Ala
                165                 170                 175

Ile Asn Lys Asn Lys Cys Asp Ile Ala Asp Leu Lys Met Ala Val Ser
            180                 185                 190

Phe Ser Gln Phe Asn Arg Arg Phe Leu Asn Val Val Arg Gln Phe Ser
        195                 200                 205

Asp Asn Ala Gly Ile Thr Pro Ala Ile Ser Leu Asp Leu Met Thr Asp
    210                 215                 220

Ala Glu Leu Ala Arg Ala Val Ser Asn Met Pro Thr Ser Ala Gly Gln
225                 230                 235                 240

Ile Lys Leu Met Leu Glu Asn Arg Ala Met Val Arg Arg Lys Gly Phe
                245                 250                 255

Gly Phe Leu Ile Gly Val Tyr Gly Ser Ser Val Ile Tyr Met Val Gln
            260                 265                 270

Leu Pro Ile Phe Gly Val Ile Asp Thr Pro Cys Trp Ile Val Lys Ala
        275                 280                 285

Ala Pro Ser Cys Ser Gly Lys Lys Gly Asn Tyr Ala Cys Leu Leu Arg
    290                 295                 300

Glu Asp Gln Gly Trp Tyr Cys Gln Asn Ala Gly Ser Thr Val Tyr Tyr
305                 310                 315                 320

Pro Asn Glu Lys Asp Cys Glu Thr Arg Gly Asp His Val Phe Cys Asp
                325                 330                 335

Thr Ala Ala Gly Ile Asn Val Ala Glu Gln Ser Lys Glu Cys Asn Ile
            340                 345                 350

Asn Ile Ser Thr Thr Asn Tyr Pro Cys Lys Val Ser Thr Gly Arg His
        355                 360                 365

Pro Ile Ser Met Val Ala Leu Ser Pro Leu Gly Ala Leu Val Ala Cys
    370                 375                 380

Tyr Lys Gly Val Ser Cys Ser Ile Gly Ser Asn Arg Val Gly Ile Ile
385                 390                 395                 400

Lys Gln Leu Asn Lys Gly Cys Ser Tyr Ile Thr Asn Gln Asp Ala Asp
                405                 410                 415

Thr Val Thr Ile Asp Asn Thr Val Tyr Gln Leu Ser Lys Val Glu Gly
            420                 425                 430

Glu Gln His Val Ile Lys Gly Arg Pro Val Ser Ser Ser Phe Asp Pro
        435                 440                 445

Val Lys Phe Pro Glu Asp Gln Phe Asn Val Ala Leu Asp Gln Val Phe
    450                 455                 460

Glu Ser Ile Glu Asn Ser Gln Ala Leu Val Asp Gln Ser Asn Arg Ile
465                 470                 475                 480

Leu Ser Ser Ala Glu Lys Gly Asn Thr Gly Phe Ile Ile Val Ile Ile
                485                 490                 495

Leu Ile Ala Val Leu Gly Ser Thr Met Ile Leu Val Ser Val Phe Ile
            500                 505                 510

Ile Ile Lys Lys Thr Lys Lys Pro Thr Gly Ala Pro Pro Glu Leu Ser
        515                 520                 525

Gly Val Thr Asn Asn Gly Phe Ile Pro His Asn
    530                 535
```

<210> SEQ ID NO 2
<211> LENGTH: 84
<212> TYPE: PRT
<213> ORGANISM: Human metapneumovirus

<400> SEQUENCE: 2

Leu Lys Glu Ser Tyr Leu Glu Glu Ser Cys Ser Thr Ile Thr Glu Gly
1               5                   10                  15

Tyr Leu Ser Val Leu Arg Thr Gly Trp Tyr Thr Asn Val Phe Thr Leu
            20                  25                  30

Glu Val Gly Asp Val Glu Asn Leu Thr Cys Ala Asp Gly Pro Ser Leu
        35                  40                  45

Ile Lys Thr Glu Leu Asp Leu Thr Lys Ser Ala Leu Arg Glu Leu Arg
    50                  55                  60

Thr Val Ser Ala Asp Gln Leu Ala Arg Glu Glu Gln Ile Glu Asn Pro
65                  70                  75                  80

Arg Gln Ser Arg

<210> SEQ ID NO 3
<211> LENGTH: 437
<212> TYPE: PRT
<213> ORGANISM: Human metapneumovirus

<400> SEQUENCE: 3

Phe Val Leu Gly Ala Ile Ala Leu Gly Val Ala Thr Ala Ala Ala Val
1               5                   10                  15

Thr Ala Gly Val Ala Ile Ala Lys Thr Ile Arg Leu Glu Ser Glu Val
            20                  25                  30

Thr Ala Ile Lys Asn Ala Leu Lys Lys Thr Asn Glu Ala Val Ser Thr
        35                  40                  45

Leu Gly Asn Gly Val Arg Val Leu Ala Thr Ala Val Arg Glu Leu Lys
    50                  55                  60

Asp Phe Val Ser Lys Asn Leu Thr Arg Ala Ile Asn Lys Asn Lys Cys
65                  70                  75                  80

Asp Ile Ala Asp Leu Lys Met Ala Val Ser Phe Ser Gln Phe Asn Arg
                85                  90                  95

Arg Phe Leu Asn Val Val Arg Gln Phe Ser Asp Asn Ala Gly Ile Thr
            100                 105                 110

Pro Ala Ile Ser Leu Asp Leu Met Thr Asp Ala Glu Leu Ala Arg Ala
        115                 120                 125

Val Ser Asn Met Pro Thr Ser Ala Gly Gln Ile Lys Leu Met Leu Glu
    130                 135                 140

Asn Arg Ala Met Val Arg Arg Lys Gly Phe Gly Phe Leu Ile Gly Val
145                 150                 155                 160

Tyr Gly Ser Ser Val Ile Tyr Met Val Gln Leu Pro Ile Phe Gly Val
                165                 170                 175

Ile Asp Thr Pro Cys Trp Ile Val Lys Ala Ala Pro Ser Cys Ser Gly
            180                 185                 190

Lys Lys Gly Asn Tyr Ala Cys Leu Leu Arg Glu Asp Gln Gly Trp Tyr
        195                 200                 205

Cys Gln Asn Ala Gly Ser Thr Val Tyr Tyr Pro Asn Glu Lys Asp Cys
    210                 215                 220

Glu Thr Arg Gly Asp His Val Phe Cys Asp Thr Ala Ala Gly Ile Asn
225                 230                 235                 240

Val Ala Glu Gln Ser Lys Glu Cys Asn Ile Asn Ile Ser Thr Thr Asn

```
                245                 250                 255

Tyr Pro Cys Lys Val Ser Thr Gly Arg His Pro Ile Ser Met Val Ala
            260                 265                 270

Leu Ser Pro Leu Gly Ala Leu Val Ala Cys Tyr Lys Gly Val Ser Cys
        275                 280                 285

Ser Ile Gly Ser Asn Arg Val Gly Ile Ile Lys Gln Leu Asn Lys Gly
    290                 295                 300

Cys Ser Tyr Ile Thr Asn Gln Asp Ala Asp Thr Val Thr Ile Asp Asn
305                 310                 315                 320

Thr Val Tyr Gln Leu Ser Lys Val Glu Gly Glu Gln His Val Ile Lys
                325                 330                 335

Gly Arg Pro Val Ser Ser Ser Phe Asp Pro Val Lys Phe Pro Glu Asp
            340                 345                 350

Gln Phe Asn Val Ala Leu Asp Gln Val Phe Glu Ser Ile Glu Asn Ser
        355                 360                 365

Gln Ala Leu Val Asp Gln Ser Asn Arg Ile Leu Ser Ser Ala Glu Lys
    370                 375                 380

Gly Asn Thr Gly Phe Ile Ile Val Ile Ile Leu Ile Ala Val Leu Gly
385                 390                 395                 400

Ser Thr Met Ile Leu Val Ser Val Phe Ile Ile Ile Lys Lys Thr Lys
                405                 410                 415

Lys Pro Thr Gly Ala Pro Pro Glu Leu Ser Gly Val Thr Asn Asn Gly
            420                 425                 430

Phe Ile Pro His Asn
        435


<210> SEQ ID NO 4
<211> LENGTH: 5
<212> TYPE: PRT
<213> ORGANISM: Artificial sequence
<220> FEATURE:
<223> OTHER INFORMATION: Synthetic

<400> SEQUENCE: 4

Cys Gly Ala Gly Ala
1               5


<210> SEQ ID NO 5
<211> LENGTH: 523
<212> TYPE: PRT
<213> ORGANISM: Artificial Sequence
<220> FEATURE:
<223> OTHER INFORMATION: Synthetic

<400> SEQUENCE: 5

Met Ser Trp Lys Val Val Ile Ile Phe Ser Leu Leu Ile Thr Pro Gln
1               5                   10                  15

His Gly Leu Lys Glu Ser Tyr Leu Glu Glu Ser Cys Ser Thr Ile Thr
            20                  25                  30

Glu Gly Tyr Leu Ser Val Leu Arg Thr Gly Trp Tyr Thr Asn Val Phe
        35                  40                  45

Thr Leu Glu Val Gly Asp Val Glu Asn Leu Thr Cys Ala Asp Gly Pro
    50                  55                  60

Ser Leu Ile Lys Thr Glu Leu Asp Leu Thr Lys Ser Ala Leu Arg Glu
65                  70                  75                  80

Leu Arg Thr Val Ser Ala Asp Gln Leu Ala Arg Glu Glu Gln Ile Glu
                85                  90                  95
```

-continued

```
Gln Pro Arg Gln Ser Gly Cys Gly Ala Gly Ala Thr Ala Gly Val Ala
            100                 105                 110

Ile Ala Lys Thr Ile Arg Leu Glu Ser Glu Val Thr Ala Ile Lys Asn
        115                 120                 125

Ala Leu Lys Lys Thr Asn Glu Ala Val Ser Thr Leu Gly Asn Gly Val
    130                 135                 140

Arg Val Leu Ala Thr Ala Val Arg Glu Leu Lys Asp Phe Val Ser Lys
145                 150                 155                 160

Asn Leu Thr Arg Ala Ile Asn Lys Asn Lys Cys Asp Ile Ala Asp Leu
                165                 170                 175

Lys Met Ala Val Ser Phe Ser Gln Phe Asn Arg Arg Phe Leu Asn Val
            180                 185                 190

Val Arg Gln Phe Ser Asp Asn Ala Gly Ile Thr Pro Ala Ile Ser Leu
        195                 200                 205

Asp Leu Met Thr Asp Ala Glu Leu Ala Arg Ala Val Ser Asn Met Pro
    210                 215                 220

Thr Ser Ala Gly Gln Ile Lys Leu Met Leu Glu Asn Arg Ala Met Val
225                 230                 235                 240

Arg Arg Lys Gly Phe Gly Phe Leu Ile Gly Val Tyr Gly Ser Ser Val
                245                 250                 255

Ile Tyr Met Val Gln Leu Pro Ile Phe Gly Val Ile Asp Thr Pro Cys
            260                 265                 270

Trp Ile Val Lys Ala Ala Pro Ser Cys Ser Glu Lys Lys Gly Asn Tyr
        275                 280                 285

Ala Cys Leu Leu Arg Glu Asp Gln Gly Trp Tyr Cys Gln Asn Ala Gly
    290                 295                 300

Ser Thr Val Tyr Tyr Pro Asn Glu Lys Asp Cys Glu Thr Arg Gly Asp
305                 310                 315                 320

His Val Phe Cys Asp Thr Cys Ala Gly Ile Asn Val Ala Glu Gln Ser
                325                 330                 335

Lys Glu Cys Asn Ile Asn Ile Ser Thr Thr Asn Tyr Pro Cys Lys Val
            340                 345                 350

Ser Thr Gly Arg His Pro Ile Ser Met Val Ala Leu Ser Pro Leu Gly
        355                 360                 365

Ala Leu Val Ala Cys Tyr Lys Gly Val Ser Cys Ser Ile Gly Ser Asn
    370                 375                 380

Arg Val Gly Ile Ile Lys Gln Leu Asn Lys Gly Cys Ser Tyr Ile Thr
385                 390                 395                 400

Asn Gln Asp Ala Asp Thr Val Thr Ile Asp Asn Thr Val Tyr Gln Leu
                405                 410                 415

Ser Lys Val Glu Gly Glu Gln His Val Ile Lys Gly Arg Pro Val Ser
            420                 425                 430

Ser Ser Phe Asp Pro Val Lys Phe Pro Glu Asp Gln Phe Asn Val Ala
        435                 440                 445

Leu Asp Gln Val Phe Glu Ser Ile Glu Asn Ser Gln Ala Leu Val Asp
    450                 455                 460

Gln Ser Asn Arg Ile Leu Ser Ala Gly Tyr Ile Pro Glu Ala Pro Arg
465                 470                 475                 480

Asp Gly Gln Ala Tyr Val Arg Lys Asp Gly Glu Trp Val Leu Leu Ser
                485                 490                 495

Thr Phe Leu Gly Gly Leu Val Pro Arg Gly Ser His His His His His
            500                 505                 510

His Ser Ala Trp Ser His Pro Gln Phe Glu Lys
```

515 520

<210> SEQ ID NO 6
<211> LENGTH: 529
<212> TYPE: PRT
<213> ORGANISM: Artificial Sequence
<220> FEATURE:
<223> OTHER INFORMATION: Synthetic

<400> SEQUENCE: 6

Met Ser Trp Lys Val Val Ile Ile Phe Ser Leu Leu Ile Thr Pro Gln
1 5 10 15

His Gly Leu Lys Glu Ser Tyr Leu Glu Glu Ser Cys Ser Thr Ile Thr
20 25 30

Glu Gly Tyr Leu Ser Val Leu Arg Thr Gly Trp Tyr Thr Asn Val Phe
35 40 45

Thr Leu Glu Val Gly Asp Val Glu Asn Leu Thr Cys Ala Asp Gly Pro
50 55 60

Ser Leu Ile Lys Thr Glu Leu Asp Leu Thr Lys Ser Ala Leu Arg Glu
65 70 75 80

Leu Arg Thr Val Ser Ala Asp Gln Leu Ala Arg Glu Glu Gln Ile Glu
85 90 95

Gln Pro Arg Gln Ser Gly Cys Gly Ala Gly Ala Thr Ala Gly Val Ala
100 105 110

Ile Ala Lys Thr Ile Arg Leu Glu Ser Glu Val Thr Ala Ile Lys Asn
115 120 125

Ala Leu Lys Lys Thr Asn Glu Ala Val Ser Thr Leu Gly Asn Gly Val
130 135 140

Arg Val Leu Ala Phe Ala Val Arg Glu Leu Lys Asp Phe Val Ser Lys
145 150 155 160

Asn Leu Thr Arg Ala Leu Asn Lys Asn Lys Cys Asp Ile Ala Asp Leu
165 170 175

Lys Met Ala Val Ser Phe Ser Gln Phe Asn Arg Arg Phe Leu Asn Val
180 185 190

Val Arg Gln Phe Ser Asp Asn Ala Gly Ile Thr Pro Ala Ile Ser Leu
195 200 205

Asp Leu Met Thr Asp Ala Glu Leu Ala Arg Ala Val Ser Asn Met Pro
210 215 220

Thr Ser Ala Gly Gln Ile Lys Leu Met Leu Glu Asn Arg Ala Met Val
225 230 235 240

Arg Arg Lys Gly Phe Gly Phe Leu Ile Gly Val Tyr Gly Ser Ser Val
245 250 255

Ile Tyr Met Val Gln Leu Pro Ile Phe Gly Val Ile Asp Thr Pro Cys
260 265 270

Trp Ile Val Lys Ala Ala Pro Ser Cys Ser Glu Lys Lys Gly Asn Tyr
275 280 285

Ala Cys Leu Leu Arg Glu Asp Gln Gly Trp Tyr Cys Gln Asn Ala Gly
290 295 300

Ser Thr Val Tyr Tyr Pro Asn Glu Lys Asp Cys Glu Thr Arg Gly Asp
305 310 315 320

His Val Phe Cys Asp Thr Cys Ala Gly Ile Asn Val Ala Glu Gln Ser
325 330 335

Lys Glu Cys Asn Ile Asn Ile Ser Thr Thr Asn Tyr Pro Cys Lys Val
340 345 350

Ser Thr Gly Arg His Pro Ile Ser Met Val Ala Leu Ser Pro Leu Gly

-continued

```
        355                 360                 365

Ala Leu Val Ala Cys Tyr Lys Gly Val Ser Cys Ser Ile Gly Ser Asn
    370                 375                 380

Arg Val Gly Ile Ile Lys Gln Leu Asn Lys Gly Cys Ser Tyr Ile Thr
385                 390                 395                 400

Asn Gln Asp Ala Asp Thr Val Thr Ile Asp Asn Thr Val Tyr Gln Leu
                405                 410                 415

Ser Lys Val Glu Gly Glu Gln His Val Ile Lys Gly Arg Pro Val Ser
            420                 425                 430

Ser Ser Phe Asp Pro Val Lys Phe Pro Glu Asp Gln Phe Asn Val Ala
        435                 440                 445

Leu Asp Gln Val Phe Glu Ser Ile Glu Asn Ser Gln Ala Leu Val Asp
    450                 455                 460

Gln Ser Asn Arg Ile Leu Ser Ser Ala Glu Ser Ala Ile Gly Gly Tyr
465                 470                 475                 480

Ile Pro Glu Ala Pro Arg Asp Gly Gln Ala Tyr Val Arg Lys Asp Gly
                485                 490                 495

Glu Trp Val Leu Leu Ser Thr Phe Leu Gly Gly Leu Val Pro Arg Gly
            500                 505                 510

Ser His His His His His His Ser Ala Trp Ser His Pro Gln Phe Glu
        515                 520                 525

Lys


<210> SEQ ID NO 7
<211> LENGTH: 523
<212> TYPE: PRT
<213> ORGANISM: Artificial Sequence
<220> FEATURE:
<223> OTHER INFORMATION: Synthetic

<400> SEQUENCE: 7

Met Ser Trp Lys Val Val Ile Ile Phe Ser Leu Leu Ile Thr Pro Gln
1               5                   10                  15

His Gly Leu Lys Glu Ser Tyr Leu Glu Glu Ser Cys Ser Thr Ile Thr
            20                  25                  30

Glu Gly Tyr Leu Ser Val Leu Arg Thr Gly Trp Tyr Thr Asn Val Phe
        35                  40                  45

Met Leu Glu Val Gly Asp Val Glu Asn Leu Thr Cys Ala Asp Gly Pro
    50                  55                  60

Ser Leu Leu Lys Thr Glu Leu Asp Leu Thr Lys Ser Ala Leu Arg Asn
65                  70                  75                  80

Leu Arg Thr Val Ser Ala Asp Gln Leu Ala Arg Glu Glu Gln Ile Glu
                85                  90                  95

Gln Pro Arg Gln Ser Gly Cys Gly Ala Gly Ala Thr Ala Gly Val Ala
            100                 105                 110

Ile Ala Lys Thr Ile Arg Leu Glu Ser Glu Val Thr Ala Ile Lys Asn
        115                 120                 125

Ala Leu Lys Lys Thr Asn Glu Ala Val Ser Thr Leu Gly Asn Gly Val
    130                 135                 140

Arg Val Leu Ala Thr Met Val Arg Glu Leu Lys Asp Phe Val Ser Lys
145                 150                 155                 160

Asn Leu Thr Arg Ala Ile Asn Lys Asn Lys Cys Asp Ile Ala Asp Leu
                165                 170                 175

Lys Met Ala Val Ser Phe Ser Gln Phe Asn Arg Arg Phe Leu Asn Val
            180                 185                 190
```

```
Val Arg Gln Phe Ser Asp Asn Ala Gly Ile Thr Pro Ala Ile Ser Leu
        195                 200                 205

Asp Leu Met Thr Asp Ala Glu Leu Ala Arg Ala Val Ser Asn Met Pro
    210                 215                 220

Thr Ser Ala Gly Gln Ile Lys Leu Met Leu Glu Asn Arg Ala Met Val
225                 230                 235                 240

Arg Arg Lys Gly Phe Gly Ile Leu Ile Gly Val Tyr Gly Ser Ser Val
                245                 250                 255

Ile Tyr Met Val Gln Leu Pro Ile Phe Gly Val Ile Asp Thr Pro Cys
            260                 265                 270

Trp Ile Val Lys Ala Ala Pro Ser Cys Ser Glu Lys Lys Gly Asn Tyr
        275                 280                 285

Ala Cys Leu Leu Arg Glu Asp Gln Gly Trp Tyr Cys Gln Asn Ala Gly
    290                 295                 300

Ser Thr Val Tyr Tyr Pro Asn Glu Lys Asp Cys Glu Thr Arg Gly Asp
305                 310                 315                 320

His Val Phe Cys Asp Thr Cys Ala Gly Ile Asn Val Ala Glu Gln Ser
                325                 330                 335

Lys Glu Cys Asn Ile Asn Ile Ser Thr Thr Asn Tyr Pro Cys Lys Val
            340                 345                 350

Ser Thr Gly Arg His Pro Ile Ser Met Val Ala Leu Ser Pro Leu Gly
        355                 360                 365

Ala Leu Val Ala Cys Tyr Lys Gly Val Ser Cys Ser Ile Gly Ser Asn
    370                 375                 380

Arg Val Gly Ile Ile Lys Gln Leu Asn Lys Gly Cys Ser Tyr Ile Thr
385                 390                 395                 400

Asn Gln Asp Ala Asp Thr Val Thr Ile Asp Asn Thr Val Tyr Gln Leu
                405                 410                 415

Ser Lys Val Glu Gly Glu Gln His Val Ile Lys Gly Arg Pro Val Ser
            420                 425                 430

Ser Ser Phe Asp Pro Val Lys Phe Pro Glu Asp Gln Phe Asn Val Ala
        435                 440                 445

Leu Asp Gln Val Phe Glu Ser Ile Glu Asn Ser Gln Ala Leu Val Asp
    450                 455                 460

Gln Ser Asn Arg Ile Leu Ser Ala Gly Tyr Ile Pro Glu Ala Pro Arg
465                 470                 475                 480

Asp Gly Gln Ala Tyr Val Arg Lys Asp Gly Glu Trp Val Leu Leu Ser
                485                 490                 495

Thr Phe Leu Gly Gly Leu Val Pro Arg Gly Ser His His His His His
            500                 505                 510

His Ser Ala Trp Ser His Pro Gln Phe Glu Lys
        515                 520
```

<210> SEQ ID NO 8
<211> LENGTH: 523
<212> TYPE: PRT
<213> ORGANISM: Artificial Sequence
<220> FEATURE:
<223> OTHER INFORMATION: Synthetic

<400> SEQUENCE: 8

```
Met Ser Trp Lys Val Val Ile Ile Phe Ser Leu Leu Ile Thr Pro Gln
1               5                   10                  15

His Gly Leu Lys Glu Ser Tyr Leu Glu Glu Ser Cys Ser Thr Ile Thr
            20                  25                  30
```

-continued

```
Glu Gly Tyr Leu Ser Val Leu Arg Thr Gly Trp Tyr Thr Asn Val Phe
        35                  40                  45

Met Leu Cys Val Gly Asp Val Glu Asn Leu Thr Cys Ala Asp Gly Pro
    50                  55                  60

Ser Leu Leu Lys Thr Glu Leu Asp Leu Thr Lys Ser Ala Leu Arg Glu
65                  70                  75                  80

Leu Arg Thr Val Ser Ala Asp Gln Leu Ala Arg Glu Glu Gln Ile Glu
                85                  90                  95

Gln Pro Arg Gln Ser Gly Cys Gly Ala Gly Ala Thr Ala Gly Val Ala
            100                 105                 110

Ile Ala Lys Thr Ile Arg Leu Glu Ser Glu Val Thr Ala Ile Lys Asn
        115                 120                 125

Ala Leu Lys Lys Thr Asn Glu Ala Val Ser Thr Leu Gly Asn Gly Val
    130                 135                 140

Arg Val Leu Ala Thr Met Val Arg Glu Leu Cys Asp Phe Val Ser Lys
145                 150                 155                 160

Asn Leu Thr Arg Ala Ile Asn Lys Asn Lys Cys Asp Ile Ala Asp Leu
                165                 170                 175

Lys Met Ala Val Ser Phe Ser Gln Phe Asn Arg Arg Phe Leu Asn Val
            180                 185                 190

Val Arg Gln Phe Ser Asp Asn Ala Gly Ile Thr Pro Ala Ile Ser Leu
        195                 200                 205

Asp Leu Met Thr Asp Ala Glu Leu Ala Arg Ala Val Ser Asn Met Pro
    210                 215                 220

Thr Ser Ala Gly Gln Ile Lys Leu Met Leu Glu Asn Arg Ala Met Val
225                 230                 235                 240

Arg Arg Lys Gly Phe Gly Phe Leu Ile Gly Val Tyr Gly Ser Asp Val
                245                 250                 255

Ile Tyr Met Val Gln Leu Pro Ile Phe Gly Val Ile Asp Thr Pro Cys
            260                 265                 270

Trp Ile Val Lys Ala Ala Pro Ser Cys Ser Glu Lys Lys Gly Asn Tyr
        275                 280                 285

Ala Cys Leu Leu Arg Glu Asp Gln Gly Trp Tyr Cys Gln Asn Ala Gly
    290                 295                 300

Ser Thr Val Tyr Tyr Pro Asn Glu Lys Asp Cys Glu Thr Arg Gly Asp
305                 310                 315                 320

His Val Phe Cys Asp Thr Cys Ala Gly Ile Asn Val Ala Glu Gln Ser
                325                 330                 335

Lys Glu Cys Asn Ile Asn Ile Ser Thr Thr Asn Tyr Pro Cys Lys Val
            340                 345                 350

Ser Thr Gly Arg His Pro Ile Ser Met Val Ala Leu Ser Pro Leu Gly
        355                 360                 365

Ala Leu Val Ala Cys Tyr Lys Gly Val Ser Cys Ser Ile Gly Ser Asn
    370                 375                 380

Arg Val Gly Ile Ile Lys Gln Leu Asn Lys Gly Cys Ser Tyr Ile Thr
385                 390                 395                 400

Asn Gln Asp Ala Asp Thr Val Thr Ile Asp Asn Thr Val Tyr Gln Leu
                405                 410                 415

Ser Lys Val Glu Gly Glu Gln His Val Ile Lys Gly Arg Pro Val Ser
            420                 425                 430

Ser Ser Phe Asp Pro Val Lys Phe Pro Glu Asp Gln Phe Asn Val Ala
        435                 440                 445
```

-continued

```
Leu Asp Gln Val Phe Glu Ser Ile Glu Asn Ser Gln Ala Leu Val Asp
    450                 455                 460

Gln Ser Asn Arg Cys Cys Ser Ala Gly Tyr Ile Pro Glu Ala Pro Arg
465                 470                 475                 480

Asp Gly Gln Ala Tyr Val Arg Lys Asp Gly Glu Trp Val Leu Leu Ser
                485                 490                 495

Thr Phe Leu Gly Gly Leu Val Pro Arg Gly Ser His His His His His
            500                 505                 510

His Ser Ala Trp Ser His Pro Gln Phe Glu Lys
        515                 520


<210> SEQ ID NO 9
<211> LENGTH: 529
<212> TYPE: PRT
<213> ORGANISM: Artificial Sequence
<220> FEATURE:
<223> OTHER INFORMATION: Synthetic

<400> SEQUENCE: 9

Met Ser Trp Lys Val Val Ile Ile Phe Ser Leu Leu Ile Thr Pro Gln
1               5                   10                  15

His Gly Leu Lys Glu Ser Tyr Leu Glu Glu Ser Cys Ser Thr Ile Thr
            20                  25                  30

Glu Gly Tyr Leu Ser Val Leu Arg Thr Gly Trp Tyr Thr Asn Val Phe
        35                  40                  45

Met Leu Glu Val Gly Asp Val Glu Asn Leu Thr Cys Ala Asp Gly Pro
    50                  55                  60

Ser Leu Ile Lys Thr Glu Leu Asp Leu Thr Lys Ser Ala Leu Arg Glu
65                  70                  75                  80

Leu Arg Thr Val Ser Ala Asp Gln Leu Ala Arg Glu Glu Gln Ile Glu
                85                  90                  95

Gln Pro Arg Gln Ser Gly Cys Gly Ala Gly Ala Thr Ala Gly Val Ala
            100                 105                 110

Ile Ala Lys Thr Ile Arg Leu Glu Ser Glu Val Thr Ala Trp Lys Asn
        115                 120                 125

Ala Leu Lys Lys Thr Asn Glu Val Val Ser Thr Leu Gly Asn Gly Val
    130                 135                 140

Arg Val Leu Val Thr Met Val Arg Glu Leu Lys Asp Phe Val Ser Lys
145                 150                 155                 160

Asn Leu Thr Arg Ala Leu Asn Lys Asn Lys Cys Asp Ile Ala Asp Leu
                165                 170                 175

Lys Met Ala Val Ser Phe Ser Gln Phe Asn Arg Arg Phe Leu Asn Val
            180                 185                 190

Val Arg Gln Phe Ser Asp Asn Ala Gly Ile Thr Pro Ala Ile Ser Leu
        195                 200                 205

Asp Leu Met Thr Asp Ala Glu Leu Ala Arg Ala Val Ser Asn Met Pro
    210                 215                 220

Thr Ser Ala Gly Gln Ile Lys Leu Met Leu Glu Asn Arg Ala Met Val
225                 230                 235                 240

Arg Arg Lys Gly Phe Gly Phe Leu Ile Gly Val Tyr Gly Ser Ser Val
                245                 250                 255

Ile Tyr Met Val Gln Leu Pro Ile Phe Gly Val Ile Asp Thr Pro Cys
            260                 265                 270

Trp Ile Val Lys Ala Ala Pro Ser Cys Ser Glu Lys Lys Gly Asn Tyr
        275                 280                 285
```

-continued

```
Ala Cys Leu Leu Arg Glu Asp Gln Gly Trp Tyr Cys Gln Asn Ala Gly
    290                 295                 300

Ser Thr Val Tyr Tyr Pro Asn Glu Lys Asp Cys Glu Thr Arg Gly Asp
305                 310                 315                 320

His Val Phe Cys Asp Thr Cys Ala Gly Ile Asn Val Ala Glu Gln Ser
                325                 330                 335

Lys Glu Cys Asn Ile Asn Ile Ser Thr Thr Asn Tyr Pro Cys Lys Val
            340                 345                 350

Ser Thr Gly Arg His Pro Ile Ser Met Val Ala Leu Ser Pro Leu Gly
        355                 360                 365

Ala Leu Val Ala Cys Tyr Lys Gly Val Ser Cys Ser Ile Gly Ser Asn
    370                 375                 380

Arg Val Gly Ile Ile Lys Gln Leu Asn Lys Gly Cys Ser Tyr Ile Thr
385                 390                 395                 400

Asn Gln Asp Ala Asp Thr Val Thr Ile Asp Asn Thr Val Tyr Gln Leu
                405                 410                 415

Ser Lys Val Glu Gly Glu Gln His Val Ile Lys Gly Arg Pro Val Ser
            420                 425                 430

Ser Ser Phe Asp Pro Val Lys Phe Pro Glu Asp Gln Phe Asn Val Ala
        435                 440                 445

Leu Asp Gln Val Phe Glu Ser Ile Glu Asn Ser Gln Ala Leu Val Asp
    450                 455                 460

Gln Ser Asn Arg Ile Leu Ser Ser Ala Glu Ser Ala Ile Gly Gly Tyr
465                 470                 475                 480

Ile Pro Glu Ala Pro Arg Asp Gly Gln Ala Tyr Val Arg Lys Asp Gly
                485                 490                 495

Glu Trp Val Leu Leu Ser Thr Phe Leu Gly Gly Leu Val Pro Arg Gly
            500                 505                 510

Ser His His His His His His Ser Ala Trp Ser His Pro Gln Phe Glu
        515                 520                 525

Lys


<210> SEQ ID NO 10
<211> LENGTH: 27
<212> TYPE: PRT
<213> ORGANISM: T4 bacteriophage

<400> SEQUENCE: 10

Gly Tyr Ile Pro Glu Ala Pro Arg Asp Gly Gln Ala Tyr Val Arg Lys
1               5                   10                  15

Asp Gly Glu Trp Val Leu Leu Ser Thr Phe Leu
            20                  25


<210> SEQ ID NO 11
<211> LENGTH: 8
<212> TYPE: PRT
<213> ORGANISM: Artificial Sequence
<220> FEATURE:
<223> OTHER INFORMATION: Synthetic

<400> SEQUENCE: 11

Gly Ser His His His His His His
1               5


<210> SEQ ID NO 12
<211> LENGTH: 10
<212> TYPE: PRT
<213> ORGANISM: Artificial Sequence
```

<220> FEATURE:
<223> OTHER INFORMATION: Synthetic

<400> SEQUENCE: 12

Ser Ala Trp Ser His Pro Gln Phe Glu Lys
1 5 10

<210> SEQ ID NO 13
<211> LENGTH: 539
<212> TYPE: PRT
<213> ORGANISM: Human metapneumovirus

<400> SEQUENCE: 13

Met Ser Trp Lys Val Val Ile Ile Phe Ser Leu Leu Ile Thr Pro Gln
1 5 10 15

His Gly Leu Lys Glu Ser Tyr Leu Glu Glu Ser Cys Ser Thr Ile Thr
20 25 30

Glu Gly Tyr Leu Ser Val Leu Arg Thr Gly Trp Tyr Thr Asn Val Phe
35 40 45

Thr Leu Glu Val Gly Asp Val Glu Asn Leu Thr Cys Ser Asp Gly Pro
50 55 60

Ser Leu Ile Lys Thr Glu Leu Asp Leu Thr Lys Ser Ala Leu Arg Glu
65 70 75 80

Leu Lys Thr Val Ser Ala Asp Gln Leu Ala Arg Glu Glu Gln Ile Glu
85 90 95

Asn Pro Arg Gln Ser Arg Phe Val Leu Gly Ala Ile Ala Leu Gly Val
100 105 110

Ala Thr Ala Ala Ala Val Thr Ala Gly Val Ala Ile Ala Lys Thr Ile
115 120 125

Arg Leu Glu Ser Glu Val Thr Ala Ile Lys Asn Ala Leu Lys Thr Thr
130 135 140

Asn Glu Ala Val Ser Thr Leu Gly Asn Gly Val Arg Val Leu Ala Thr
145 150 155 160

Ala Val Arg Glu Leu Lys Asp Phe Val Ser Lys Asn Leu Thr Arg Ala
165 170 175

Ile Asn Lys Asn Lys Cys Asp Ile Asp Asp Leu Lys Met Ala Val Ser
180 185 190

Phe Ser Gln Phe Asn Arg Arg Phe Leu Asn Val Val Arg Gln Phe Ser
195 200 205

Asp Asn Ala Gly Ile Thr Pro Ala Ile Ser Leu Asp Leu Met Thr Asp
210 215 220

Ala Glu Leu Ala Arg Ala Val Ser Asn Met Pro Thr Ser Ala Gly Gln
225 230 235 240

Ile Lys Leu Met Leu Glu Asn Arg Ala Met Val Arg Arg Lys Gly Phe
245 250 255

Gly Ile Leu Ile Gly Val Tyr Gly Ser Ser Val Ile Tyr Thr Val Gln
260 265 270

Leu Pro Ile Phe Gly Val Ile Asp Thr Pro Cys Trp Ile Val Lys Ala
275 280 285

Ala Pro Ser Cys Ser Glu Lys Lys Gly Asn Tyr Ala Cys Leu Leu Arg
290 295 300

Glu Asp Gln Gly Trp Tyr Cys Gln Asn Ala Gly Ser Thr Val Tyr Tyr
305 310 315 320

Pro Asn Glu Lys Asp Cys Glu Thr Arg Gly Asp His Val Phe Cys Asp
325 330 335

-continued

```
Thr Ala Ala Gly Ile Asn Val Ala Glu Gln Ser Lys Glu Cys Asn Ile
            340                 345                 350

Asn Ile Ser Thr Thr Asn Tyr Pro Cys Lys Val Ser Thr Gly Arg His
        355                 360                 365

Pro Ile Ser Met Val Ala Leu Ser Pro Leu Gly Ala Leu Val Ala Cys
    370                 375                 380

Tyr Lys Gly Val Ser Cys Ser Ile Gly Ser Asn Arg Val Gly Ile Ile
385                 390                 395                 400

Lys Gln Leu Asn Lys Gly Cys Ser Tyr Ile Thr Asn Gln Asp Ala Asp
                405                 410                 415

Thr Val Thr Ile Asp Asn Thr Val Tyr Gln Leu Ser Lys Val Glu Gly
            420                 425                 430

Glu Gln His Val Ile Lys Gly Arg Pro Val Ser Ser Ser Phe Asp Pro
        435                 440                 445

Ile Lys Phe Pro Glu Asp Gln Phe Asn Val Ala Leu Asp Gln Val Phe
    450                 455                 460

Glu Asn Ile Glu Asn Ser Gln Ala Leu Val Asp Gln Ser Asn Arg Ile
465                 470                 475                 480

Leu Ser Ser Ala Glu Lys Gly Asn Thr Gly Phe Ile Ile Val Ile Ile
                485                 490                 495

Leu Ile Ala Val Leu Gly Ser Ser Met Ile Leu Val Ser Ile Phe Ile
            500                 505                 510

Ile Ile Lys Lys Thr Lys Lys Pro Thr Gly Ala Pro Pro Glu Leu Ser
        515                 520                 525

Gly Val Thr Asn Asn Gly Phe Ile Pro His Ser
    530                 535


<210> SEQ ID NO 14
<211> LENGTH: 539
<212> TYPE: PRT
<213> ORGANISM: Human metapneumovirus

<400> SEQUENCE: 14

Met Ser Trp Lys Val Val Ile Ile Phe Ser Leu Leu Ile Thr Pro Gln
1               5                   10                  15

His Gly Leu Lys Glu Ser Tyr Leu Glu Glu Ser Cys Ser Thr Ile Thr
            20                  25                  30

Glu Gly Tyr Leu Ser Val Leu Arg Thr Gly Trp Tyr Thr Asn Val Phe
        35                  40                  45

Thr Leu Glu Val Gly Asp Val Glu Asn Leu Thr Cys Ser Asp Gly Pro
    50                  55                  60

Ser Leu Ile Lys Thr Glu Leu Asp Leu Thr Lys Ser Ala Leu Arg Glu
65                  70                  75                  80

Leu Lys Thr Val Ser Ala Asp Gln Leu Ala Arg Glu Glu Gln Ile Glu
                85                  90                  95

Asn Pro Arg Gln Ser Arg Phe Val Leu Gly Ala Ile Ala Leu Gly Val
            100                 105                 110

Ala Thr Ala Ala Ala Val Thr Ala Gly Val Ala Ile Ala Lys Thr Ile
        115                 120                 125

Arg Leu Glu Ser Glu Val Thr Ala Ile Lys Asn Ala Leu Lys Thr Thr
    130                 135                 140

Asn Glu Ala Val Ser Thr Leu Gly Asn Gly Val Arg Val Leu Ala Thr
145                 150                 155                 160

Ala Val Arg Glu Leu Lys Asp Phe Val Ser Lys Asn Leu Thr Arg Ala
                165                 170                 175
```

-continued

```
Ile Asn Lys Asn Lys Cys Asp Ile Asp Asp Leu Lys Met Ala Val Ser
            180                 185                 190

Phe Ser Gln Phe Asn Arg Arg Phe Leu Asn Val Val Arg Gln Phe Ser
        195                 200                 205

Asp Asn Ala Gly Ile Thr Pro Ala Ile Ser Leu Asp Leu Met Thr Asp
    210                 215                 220

Ala Glu Leu Ala Arg Ala Val Ser Asn Met Pro Thr Ser Ala Gly Gln
225                 230                 235                 240

Ile Lys Leu Met Leu Glu Asn Arg Ala Met Val Arg Arg Lys Gly Phe
                245                 250                 255

Gly Ile Leu Ile Gly Val Tyr Gly Ser Ser Val Ile Tyr Met Val Gln
            260                 265                 270

Leu Pro Ile Phe Gly Val Ile Asp Thr Pro Cys Trp Ile Val Lys Ala
        275                 280                 285

Ala Pro Ser Cys Ser Gly Lys Lys Gly Asn Tyr Ala Cys Leu Leu Arg
    290                 295                 300

Glu Asp Gln Gly Trp Tyr Cys Gln Asn Ala Gly Ser Thr Val Tyr Tyr
305                 310                 315                 320

Pro Asn Glu Lys Asp Cys Glu Thr Arg Gly Asp His Val Phe Cys Asp
                325                 330                 335

Thr Ala Ala Gly Ile Asn Val Ala Glu Gln Ser Lys Glu Cys Asn Ile
            340                 345                 350

Asn Ile Ser Thr Thr Asn Tyr Pro Cys Lys Val Ser Thr Gly Arg His
        355                 360                 365

Pro Ile Ser Met Val Ala Leu Ser Pro Leu Gly Ala Leu Val Ala Cys
    370                 375                 380

Tyr Lys Gly Val Ser Cys Ser Ile Gly Ser Asn Arg Val Gly Ile Ile
385                 390                 395                 400

Lys Gln Leu Asn Lys Gly Cys Ser Tyr Ile Thr Asn Gln Asp Ala Asp
                405                 410                 415

Thr Val Thr Ile Asp Asn Thr Val Tyr Gln Leu Ser Lys Val Glu Gly
            420                 425                 430

Glu Gln His Val Ile Lys Gly Arg Pro Val Ser Ser Ser Phe Asp Pro
        435                 440                 445

Ile Lys Phe Pro Glu Asp Gln Phe Asn Val Ala Leu Asp Gln Val Phe
    450                 455                 460

Glu Asn Ile Glu Asn Ser Gln Ala Leu Val Asp Gln Ser Asn Arg Ile
465                 470                 475                 480

Leu Ser Ser Ala Glu Lys Gly Asn Thr Gly Phe Ile Ile Val Ile Ile
                485                 490                 495

Leu Ile Ala Val Leu Gly Ser Ser Met Ile Leu Val Ser Ile Phe Ile
            500                 505                 510

Ile Ile Lys Lys Thr Lys Lys Pro Thr Gly Ala Pro Pro Glu Leu Ser
        515                 520                 525

Gly Val Thr Asn Asn Gly Phe Ile Pro His Ser
    530                 535
```

```
<210> SEQ ID NO 15
<211> LENGTH: 539
<212> TYPE: PRT
<213> ORGANISM: Human metapneumovirus

<400> SEQUENCE: 15

Met Ser Trp Lys Val Val Ile Ile Phe Ser Leu Leu Ile Thr Pro Gln
```

-continued

```
1               5                   10                  15

His Ser Leu Lys Glu Ser Tyr Leu Glu Glu Ser Cys Ser Thr Ile Thr
            20                  25                  30

Glu Gly Tyr Leu Ser Val Leu Arg Thr Gly Trp Tyr Thr Asn Val Phe
        35                  40                  45

Thr Leu Glu Val Gly Asp Val Glu Asn Leu Thr Cys Ala Asp Gly Pro
    50                  55                  60

Ser Leu Ile Lys Thr Glu Leu Asp Leu Thr Lys Ser Ala Leu Arg Glu
65                  70                  75                  80

Leu Lys Pro Val Ser Ala Asp Gln Leu Ala Arg Glu Glu Gln Ile Glu
                85                  90                  95

Asn Pro Arg Gln Ser Arg Phe Val Leu Gly Ala Ile Ala Leu Gly Val
            100                 105                 110

Ala Thr Ala Ala Ala Val Thr Ala Gly Val Ala Ile Ala Lys Thr Ile
        115                 120                 125

Arg Leu Glu Ser Glu Val Thr Ala Ile Lys Asn Ala Leu Lys Lys Thr
    130                 135                 140

Asn Glu Ala Val Ser Thr Leu Gly Asn Gly Val Arg Val Leu Ala Thr
145                 150                 155                 160

Ala Val Arg Glu Leu Lys Asp Phe Val Ser Lys Asn Leu Thr Arg Ala
                165                 170                 175

Ile Asn Lys Asn Lys Cys Asp Ile Asp Asp Leu Lys Met Ala Val Ser
            180                 185                 190

Phe Ser Gln Phe Asn Arg Arg Phe Leu Asn Val Val Arg Gln Phe Ser
        195                 200                 205

Asp Asn Ala Gly Ile Thr Pro Ala Ile Ser Leu Asp Leu Met Thr Asp
    210                 215                 220

Ala Glu Leu Ala Arg Ala Val Ser Asn Met Pro Thr Ala Ala Gly Gln
225                 230                 235                 240

Ile Lys Leu Met Leu Glu Asn Arg Ala Met Val Arg Arg Lys Gly Phe
                245                 250                 255

Gly Ile Leu Ile Gly Val Tyr Gly Ser Ser Val Ile Tyr Met Val Gln
            260                 265                 270

Leu Pro Ile Phe Gly Val Ile Asp Thr Pro Cys Trp Ile Val Lys Ala
        275                 280                 285

Ala Pro Ser Cys Ser Glu Lys Lys Gly Asn Tyr Ala Cys Leu Leu Arg
    290                 295                 300

Glu Asp Gln Gly Trp Tyr Cys Gln Asn Ala Gly Ser Thr Val Tyr Tyr
305                 310                 315                 320

Pro Asn Glu Lys Asp Cys Glu Thr Arg Gly Asp His Val Phe Cys Asp
                325                 330                 335

Thr Ala Ala Gly Ile Asn Val Ala Glu Gln Ser Lys Glu Cys Asn Ile
            340                 345                 350

Asn Ile Ser Thr Thr Asn Tyr Pro Cys Lys Val Ser Thr Gly Arg His
        355                 360                 365

Pro Ile Ser Met Val Ala Leu Ser Pro Leu Gly Ala Leu Val Ala Cys
    370                 375                 380

Tyr Lys Gly Val Ser Cys Ser Ile Gly Ser Asn Arg Val Gly Ile Ile
385                 390                 395                 400

Lys Gln Leu Asn Lys Gly Cys Ser Tyr Ile Thr Asn Gln Asp Ala Asp
                405                 410                 415

Thr Val Thr Ile Asp Asn Thr Val Tyr Gln Leu Ser Lys Val Glu Gly
            420                 425                 430
```

```
Glu Gln His Val Ile Lys Gly Arg Pro Val Ser Ser Ser Phe Asp Pro
        435                 440                 445

Val Lys Phe Pro Glu Asp Gln Phe Asn Val Ala Leu Asp Gln Val Phe
    450                 455                 460

Glu Asn Ile Glu Asn Ser Gln Ala Leu Val Asp Gln Ser Asn Arg Ile
465                 470                 475                 480

Leu Ser Ser Ala Glu Lys Gly Asn Thr Gly Phe Ile Ile Val Ile Ile
                485                 490                 495

Leu Ile Ala Val Leu Gly Ser Ser Met Ile Leu Val Ser Val Phe Ile
            500                 505                 510

Ile Ile Lys Lys Thr Arg Lys Pro Thr Gly Ala Pro Pro Glu Leu Ser
        515                 520                 525

Gly Val Thr Asn Asn Gly Phe Ile Pro His Ser
    530                 535


<210> SEQ ID NO 16
<211> LENGTH: 539
<212> TYPE: PRT
<213> ORGANISM: Human metapneumovirus

<400> SEQUENCE: 16

Met Ser Trp Lys Val Met Ile Ile Ile Ser Leu Leu Ile Thr Pro Gln
1               5                   10                  15

His Gly Leu Lys Glu Ser Tyr Leu Glu Glu Ser Cys Ser Thr Ile Thr
            20                  25                  30

Glu Gly Tyr Leu Ser Val Leu Arg Thr Gly Trp Tyr Thr Asn Val Phe
        35                  40                  45

Thr Leu Glu Val Gly Asp Val Glu Asn Leu Thr Cys Thr Asp Gly Pro
    50                  55                  60

Ser Leu Ile Lys Thr Glu Leu Asp Leu Thr Lys Ser Ala Leu Arg Glu
65                  70                  75                  80

Leu Lys Thr Val Ser Ala Asp Gln Leu Ala Arg Glu Glu Gln Ile Glu
                85                  90                  95

Asn Pro Arg Gln Ser Arg Phe Val Leu Gly Ala Ile Ala Leu Gly Val
            100                 105                 110

Ala Thr Ala Ala Ala Val Thr Ala Gly Ile Ala Ile Ala Lys Thr Ile
        115                 120                 125

Arg Leu Glu Ser Glu Val Asn Ala Ile Lys Gly Ala Leu Lys Gln Thr
    130                 135                 140

Asn Glu Ala Val Ser Thr Leu Gly Asn Gly Val Arg Val Leu Ala Thr
145                 150                 155                 160

Ala Val Arg Glu Leu Lys Glu Phe Val Ser Lys Asn Leu Thr Ser Ala
                165                 170                 175

Ile Asn Arg Asn Lys Cys Asp Ile Ala Asp Leu Lys Met Ala Val Ser
            180                 185                 190

Phe Ser Gln Phe Asn Arg Arg Phe Leu Asn Val Val Arg Gln Phe Ser
        195                 200                 205

Asp Asn Ala Gly Ile Thr Pro Ala Ile Ser Leu Asp Leu Met Thr Asp
    210                 215                 220

Ala Glu Leu Ala Arg Ala Val Ser Tyr Met Pro Thr Ser Ala Gly Gln
225                 230                 235                 240

Ile Lys Leu Met Leu Glu Asn Arg Ala Met Val Arg Arg Lys Gly Phe
                245                 250                 255

Gly Ile Leu Ile Gly Val Tyr Gly Ser Ser Val Ile Tyr Met Val Gln
```

-continued

```
            260                 265                 270

Leu Pro Ile Phe Gly Val Ile Asp Thr Pro Cys Trp Ile Ile Lys Ala
        275                 280                 285

Ala Pro Ser Cys Ser Glu Lys Asn Gly Asn Tyr Ala Cys Leu Leu Arg
    290                 295                 300

Glu Asp Gln Gly Trp Tyr Cys Lys Asn Ala Gly Ser Thr Val Tyr Tyr
305                 310                 315                 320

Pro Asn Glu Lys Asp Cys Glu Thr Arg Gly Asp His Val Phe Cys Asp
                325                 330                 335

Thr Ala Ala Gly Ile Asn Val Ala Glu Gln Ser Arg Glu Cys Asn Ile
            340                 345                 350

Asn Ile Ser Thr Thr Asn Tyr Pro Cys Lys Val Ser Thr Gly Arg His
        355                 360                 365

Pro Ile Ser Met Val Ala Leu Ser Pro Leu Gly Ala Leu Val Ala Cys
    370                 375                 380

Tyr Lys Gly Val Ser Cys Ser Ile Gly Ser Asn Trp Val Gly Ile Ile
385                 390                 395                 400

Lys Gln Leu Pro Lys Gly Cys Ser Tyr Ile Thr Asn Gln Asp Ala Asp
                405                 410                 415

Thr Val Thr Ile Asp Asn Thr Val Tyr Gln Leu Ser Lys Val Glu Gly
            420                 425                 430

Glu Gln His Val Ile Lys Gly Arg Pro Val Ser Ser Ser Phe Asp Pro
        435                 440                 445

Ile Lys Phe Pro Glu Asp Gln Phe Asn Val Ala Leu Asp Gln Val Phe
    450                 455                 460

Glu Ser Ile Glu Asn Ser Gln Ala Leu Val Asp Gln Ser Asn Lys Ile
465                 470                 475                 480

Leu Asn Ser Ala Glu Lys Gly Asn Thr Gly Phe Ile Ile Val Val Ile
                485                 490                 495

Leu Val Ala Val Leu Gly Leu Thr Met Ile Ser Val Ser Ile Ile Ile
            500                 505                 510

Ile Ile Lys Lys Thr Arg Lys Pro Thr Gly Ala Pro Pro Glu Leu Asn
        515                 520                 525

Gly Val Thr Asn Gly Gly Phe Ile Pro His Ser
    530                 535


<210> SEQ ID NO 17
<211> LENGTH: 539
<212> TYPE: PRT
<213> ORGANISM: Human metapneumovirus

<400> SEQUENCE: 17

Met Ser Trp Lys Val Val Ile Ile Phe Ser Leu Leu Ile Thr Pro Gln
1               5                   10                  15

His Gly Leu Lys Glu Ser Tyr Leu Glu Glu Ser Cys Ser Thr Ile Thr
            20                  25                  30

Glu Gly Tyr Leu Ser Val Leu Arg Thr Gly Trp Tyr Thr Asn Val Phe
        35                  40                  45

Thr Leu Glu Val Gly Asp Val Glu Asn Leu Thr Cys Ala Asp Gly Pro
    50                  55                  60

Ser Leu Ile Lys Thr Glu Leu Asp Leu Thr Lys Ser Ala Leu Arg Glu
65                  70                  75                  80

Leu Arg Thr Val Ser Ala Asp Gln Leu Ala Arg Glu Glu Gln Ile Glu
                85                  90                  95
```

-continued

```
Asn Pro Arg Gln Ser Arg Phe Val Leu Gly Ala Ile Ala Leu Gly Val
            100                 105                 110

Ala Thr Ala Ala Ala Val Thr Ala Gly Val Ala Ile Ala Lys Thr Ile
        115                 120                 125

Arg Leu Glu Ser Glu Val Thr Ala Ile Lys Asn Ala Leu Lys Lys Thr
    130                 135                 140

Asn Glu Ala Val Ser Thr Leu Gly Asn Gly Val Arg Val Leu Ala Thr
145                 150                 155                 160

Ala Val Arg Glu Leu Lys Asp Phe Val Ser Lys Asn Leu Thr Arg Ala
                165                 170                 175

Ile Asn Lys Asn Lys Cys Asp Ile Ala Asp Leu Lys Met Ala Val Ser
            180                 185                 190

Phe Ser Gln Phe Asn Arg Arg Phe Leu Asn Val Val Arg Gln Phe Ser
        195                 200                 205

Asp Asn Ala Gly Ile Thr Pro Ala Ile Ser Leu Asp Leu Met Thr Asp
    210                 215                 220

Ala Glu Leu Ala Arg Ala Val Ser Asn Met Pro Thr Ser Ala Gly Gln
225                 230                 235                 240

Ile Lys Leu Met Leu Glu Asn Arg Ala Met Val Arg Arg Lys Gly Phe
                245                 250                 255

Gly Phe Leu Ile Gly Val Tyr Gly Ser Ser Val Ile Tyr Met Val Gln
            260                 265                 270

Leu Pro Ile Phe Gly Val Ile Asp Thr Pro Cys Trp Ile Val Lys Ala
        275                 280                 285

Ala Pro Ser Cys Ser Gly Lys Lys Gly Asn Tyr Ala Cys Leu Leu Arg
    290                 295                 300

Glu Asp Gln Gly Trp Tyr Cys Gln Asn Ala Gly Ser Thr Val Tyr Tyr
305                 310                 315                 320

Pro Asn Glu Lys Asp Cys Glu Thr Arg Gly Asp His Val Phe Cys Asp
                325                 330                 335

Thr Ala Ala Gly Ile Asn Val Ala Glu Gln Ser Lys Glu Cys Asn Ile
            340                 345                 350

Asn Ile Ser Thr Thr Asn Tyr Pro Cys Lys Val Ser Thr Gly Arg His
        355                 360                 365

Pro Ile Ser Met Val Ala Leu Ser Pro Leu Gly Ala Leu Val Ala Cys
    370                 375                 380

Tyr Lys Gly Val Ser Cys Ser Ile Gly Ser Asn Arg Val Gly Ile Ile
385                 390                 395                 400

Lys Gln Leu Asn Lys Gly Cys Ser Tyr Ile Thr Asn Gln Asp Ala Asp
                405                 410                 415

Thr Val Thr Ile Asp Asn Thr Val Tyr Gln Leu Ser Lys Val Glu Gly
            420                 425                 430

Glu Gln His Val Ile Lys Gly Arg Pro Val Ser Ser Ser Phe Asp Pro
        435                 440                 445

Val Lys Phe Pro Glu Asp Gln Phe Asn Val Ala Leu Asp Gln Val Phe
    450                 455                 460

Glu Ser Ile Glu Asn Ser Gln Ala Leu Val Asp Gln Ser Asn Arg Ile
465                 470                 475                 480

Leu Ser Ser Ala Glu Lys Gly Asn Thr Gly Phe Ile Ile Val Ile Ile
                485                 490                 495

Leu Ile Ala Val Leu Gly Ser Thr Met Ile Leu Val Ser Val Phe Ile
            500                 505                 510

Ile Ile Lys Lys Thr Lys Lys Pro Thr Gly Ala Pro Pro Glu Leu Ser
```

```
        515                 520                 525

Gly Val Thr Asn Asn Gly Phe Ile Pro His Asn
    530                 535


<210> SEQ ID NO 18
<211> LENGTH: 539
<212> TYPE: PRT
<213> ORGANISM: Human metapneumovirus

<400> SEQUENCE: 18

Met Ser Trp Lys Val Met Ile Ile Ile Ser Leu Leu Ile Thr Pro Gln
1               5                   10                  15

His Gly Leu Lys Glu Ser Tyr Leu Glu Glu Ser Cys Ser Thr Ile Thr
            20                  25                  30

Glu Gly Tyr Leu Ser Val Leu Arg Thr Gly Trp Tyr Thr Asn Val Phe
        35                  40                  45

Thr Leu Glu Val Gly Asp Val Glu Asn Leu Thr Cys Thr Asp Gly Pro
    50                  55                  60

Ser Leu Ile Lys Thr Glu Leu Asp Leu Thr Lys Ser Ala Leu Arg Glu
65                  70                  75                  80

Leu Lys Thr Val Ser Ala Asp Gln Leu Ala Arg Glu Glu Gln Ile Glu
                85                  90                  95

Asn Pro Arg Gln Ser Arg Phe Val Leu Gly Ala Ile Ala Leu Gly Val
            100                 105                 110

Ala Thr Ala Ala Ala Val Thr Ala Gly Ile Ala Ile Ala Lys Thr Ile
        115                 120                 125

Arg Leu Glu Ser Glu Val Asn Ala Ile Lys Gly Ala Leu Lys Thr Thr
    130                 135                 140

Asn Glu Ala Val Ser Thr Leu Gly Asn Gly Val Arg Val Leu Ala Thr
145                 150                 155                 160

Ala Val Arg Glu Leu Lys Glu Phe Val Ser Lys Asn Leu Thr Ser Ala
                165                 170                 175

Ile Asn Lys Asn Lys Cys Asp Ile Ala Asp Leu Lys Met Ala Val Ser
            180                 185                 190

Phe Ser Gln Phe Asn Arg Arg Phe Leu Asn Val Val Arg Gln Phe Ser
        195                 200                 205

Asp Asn Ala Gly Ile Thr Pro Ala Ile Ser Leu Asp Leu Met Thr Asp
    210                 215                 220

Ala Glu Leu Ala Arg Ala Val Ser Tyr Met Pro Thr Ser Ala Gly Gln
225                 230                 235                 240

Ile Lys Leu Met Leu Glu Asn Arg Ala Met Val Arg Arg Lys Gly Phe
                245                 250                 255

Gly Ile Leu Ile Gly Val Tyr Gly Ser Ser Val Ile Tyr Met Val Gln
            260                 265                 270

Leu Pro Ile Phe Gly Val Ile Asp Thr Pro Cys Trp Ile Ile Lys Ala
        275                 280                 285

Ala Pro Ser Cys Ser Glu Lys Asp Gly Asn Tyr Ala Cys Leu Leu Arg
    290                 295                 300

Glu Asp Gln Gly Trp Tyr Cys Lys Asn Ala Gly Ser Thr Val Tyr Tyr
305                 310                 315                 320

Pro Asn Lys Lys Asp Cys Glu Thr Arg Gly Asp His Val Phe Cys Asp
                325                 330                 335

Thr Ala Ala Gly Ile Asn Val Ala Glu Gln Ser Arg Glu Cys Asn Ile
            340                 345                 350
```

```
Asn Ile Ser Thr Thr Asn Tyr Pro Cys Lys Val Ser Thr Gly Arg His
        355                 360                 365

Pro Ile Ser Met Val Ala Leu Ser Pro Leu Gly Ala Leu Val Ala Cys
    370                 375                 380

Tyr Lys Gly Val Ser Cys Ser Ile Gly Ser Asn Arg Val Gly Ile Ile
385                 390                 395                 400

Lys Gln Leu Pro Lys Gly Cys Ser Tyr Ile Thr Asn Gln Asp Ala Asp
                405                 410                 415

Thr Val Thr Ile Asp Asn Thr Val Tyr Gln Leu Ser Lys Val Glu Gly
            420                 425                 430

Glu Gln His Val Ile Lys Gly Arg Pro Val Ser Ser Ser Phe Asp Pro
        435                 440                 445

Ile Lys Phe Pro Glu Asp Gln Phe Asn Val Ala Leu Asp Gln Val Phe
    450                 455                 460

Glu Ser Ile Glu Asn Ser Gln Ala Leu Val Asp Gln Ser Asn Lys Ile
465                 470                 475                 480

Leu Asn Ser Ala Glu Lys Gly Asn Thr Gly Phe Ile Ile Val Ile Ile
                485                 490                 495

Leu Ile Ala Val Leu Gly Leu Thr Met Ile Ser Val Ser Ile Ile Ile
            500                 505                 510

Ile Ile Lys Lys Thr Arg Lys Pro Thr Gly Ala Pro Pro Glu Leu Asn
        515                 520                 525

Gly Val Thr Asn Gly Gly Phe Ile Pro His Ser
    530                 535
```

<210> SEQ ID NO 19
<211> LENGTH: 1590
<212> TYPE: DNA
<213> ORGANISM: Artificial Sequence
<220> FEATURE:
<223> OTHER INFORMATION: Synthetic

<400> SEQUENCE: 19

```
atgtcttgga aggtggtcat catcttctcc ctgctgatca cccctcagca cggcctgaaa     60

gagtcctacc tggaagagag ctgctccacc atcaccgagg gctacctgtc tgtgctgaga    120

accggctggt acaccaacgt gttcaccctg gaagtgggcg acgtggaaaa cctgacctgt    180

gctgatggcc ccagcctgat caagaccgag ctggacctga ccaagtctgc cctgagagaa    240

ctgaggaccg tgtctgccga tcagctggcc agagaggaac agatcgagca gcctagacag    300

tccggatgtg gtgctggtgc tacagctggc gtggccattg ccaagaccat ccggctggaa    360

tctgaagtga ccgccatcaa gaacgccctg aaaaagacca acgaggccgt gtctaccctc    420

ggcaatggcg ttagagtgct ggcctttgct gtgcgcgagc tgaaggactt cgtgtccaag    480

aacctgacca gggctctgaa caagaacaag tgtgatatcg ccgacctgaa gatggccgtg    540

tcctttagcc agttcaaccg gcggttcctg aacgtcgtgc ggcagttctc tgataacgcc    600

ggcatcaccc ctgccatcag cctggatctg atgaccgatg ccgagctggc tagagccgtg    660

tccaacatgc ctacctctgc cggccagatc aagctgatgc tggaaaacag agccatggtc    720

cgacggaaag gcttcggctt tctgatcggc gtgtacggct cctccgtgat ctacatggtg    780

cagctgccta tcttcggcgt gatcgacacc ccttgctgga tcgtgaaggc cgctcctagc    840

tgctctgaga agaagggcaa ctacgcctgc ctgctgagag aggaccaagg ctggtactgt    900

cagaacgccg gctccaccgt gtactacccc aacgagaagg actgcgagac aagaggcgac    960

cacgtgttct gcgatacctg cgctggcatc aatgtggccg agcagtccaa agagtgcaac   1020
```

atcaacatct ccaccaccaa ctatccctgc aaggtgtcca ccggcaggca ccctatttcc 1080
atggtggctc tgtctccact gggcgccctg gtggcttgtt ataagggcgt gtcctgctcc 1140
atcggctcca acagagtggg catcatcaag cagctgaaca agggctgcag ctacatcacc 1200
aaccaggacg ccgataccgt gaccatcgac aataccgtgt atcagctgtc caaggtggaa 1260
ggcgagcagc acgtgatcaa gggcagacct gtgtcctcca gcttcgaccc cgtgaagttc 1320
cctgaggatc agttcaacgt ggccctggac caggtgttcg agtccatcga gaactctcag 1380
gctctggtgg accagtccaa ccggatcctg tcctctgccg agtctgctat cggcggctat 1440
atccccgagg ctcctagaga tggccaggcc tatgttcgga aggatggcga atgggtgctg 1500
ctgtctacct tcctcggagg cctggtgcct agaggctctc accaccatca tcaccactcc 1560
gcttggtccc atccacagtt cgagaagtga 1590

<210> SEQ ID NO 20
<211> LENGTH: 1572
<212> TYPE: DNA
<213> ORGANISM: Artificial Sequence
<220> FEATURE:
<223> OTHER INFORMATION: Synthetic

<400> SEQUENCE: 20
atgtcttgga aggtggtcat catcttctcc ctgctgatca cccctcagca cggcctgaaa 60
gagtcctacc tggaagagag ctgctccacc atcaccgagg gctacctgtc tgtgctgaga 120
accggctggt acaccaacgt gttcaccctg gaagtgggcg acgtggaaaa cctgacctgt 180
gctgatggcc ccagcctgat caagaccgag ctggacctga ccaagtctgc cctgagagaa 240
ctgaggaccg tgtctgccga tcagctggcc agagaggaac agatcgagca gcctagacag 300
tccggatgtg gtgctggtgc tacagctggc gtggccattg ccaagaccat ccggctggaa 360
tctgaagtga ccgccatcaa gaacgccctg aaaaagacca acgaggccgt gtctaccctc 420
ggcaatggcg ttagagtgct ggccacagcc gtgcgcgagc tgaaggattt cgtgtccaag 480
aacctgacca gggccatcaa caagaacaag tgtgatatcg ccgacctgaa gatggccgtg 540
tccttcagcc agttcaaccg gcggttcctg aatgtcgtgc ggcagttctc tgacaacgcc 600
ggcatcaccc ctgccatcag cctggatctg atgaccgatg ccgagctggc tagagccgtg 660
tccaacatgc ctacctctgc cggccagatc aagctgatgc tggaaaacag agccatggtc 720
cgacggaaag gcttcggctt tctgatcggc gtgtacggct cctccgtgat ctacatggtg 780
cagctgccta tcttcggcgt gatcgacacc ccttgctgga tcgtgaaggc cgctcctagc 840
tgctctgaga agaagggcaa ctacgcctgc ctgctgagag aggaccaagg ctggtactgt 900
cagaacgccg gctccaccgt gtactacccc aacgagaagg actgcgagac aagaggcgac 960
cacgtgttct gcgatacctg cgctggcatc aatgtggccg agcagtccaa agagtgcaac 1020
atcaacatct ccaccaccaa ctatccctgc aaggtgtcca ccggcaggca ccctatttcc 1080
atggtggctc tgtctccact gggcgccctg gtggcttgtt ataagggcgt gtcctgctcc 1140
atcggctcca acagagtggg catcatcaag cagctgaaca agggctgcag ctacatcacc 1200
aaccaggacg ccgataccgt gaccatcgac aataccgtgt atcagctgtc caaggtggaa 1260
ggcgagcagc acgtgatcaa gggcagacct gtgtcctcca gcttcgaccc cgtgaagttc 1320
cctgaggatc agttcaacgt ggccctggac caggtgttcg agtccatcga gaactctcag 1380
gctctggtgg accagtccaa ccggattctg tctgccggct acatccccga ggctcctaga 1440
gatggacagg cctacgtcag aaaggacggc gaatgggtgc tgctgtctac ctttctcgga 1500
ggcctggtgc ctagaggctc tcaccaccat catcaccact ccgcttggtc ccatccacag 1560
ttcgagaagt ga 1572

<210> SEQ ID NO 21
<211> LENGTH: 1572
<212> TYPE: DNA
<213> ORGANISM: Artificial Sequence
<220> FEATURE:
<223> OTHER INFORMATION: Synthetic

<400> SEQUENCE: 21
atgtcttgga aggtggtcat catcttctcc ctgctgatca cccctcagca cggcctgaaa 60
gagtcctacc tggaagagag ctgctccacc atcaccgagg gctacctgtc tgtgctgaga 120
accggctggt acaccaacgt gttcatgctg gaagtgggcg acgtggaaaa cctgacctgt 180
gctgatggcc ccagcctgct gaaaacagag ctggacctga ccaagagcgc cctgagaaat 240
ctgaggaccg tgtctgccga tcagctggcc agagaggaac agatcgagca gcctagacag 300
tccggatgtg gtgctggtgc tacagctggc gtggccattg ccaagaccat ccggctggaa 360
tctgaagtga ccgccatcaa gaatgccctg aaaaagacca acgaggccgt gtctaccctc 420
ggcaatggcg ttagagtgct ggccacaatg gtccgagagc tgaaggactt cgtgtccaag 480
aacctgacca gggccatcaa caagaacaag tgtgatatcg ccgacctgaa gatggccgtg 540
tcctttagcc agttcaaccg gcggttcctg aacgtcgtgc ggcagttctc tgataacgcc 600
ggcatcaccc ctgccatcag cctggatctg atgaccgatg ccgagctggc tagagccgtg 660
tccaacatgc ctacctctgc cggccagatc aagctgatgc tcgagaacag agctatggtc 720
cgacggaaag gcttcggcat cctgatcggc gtgtacggct cctccgtgat ctacatggtg 780
cagctgccta tcttcggcgt gatcgacacc ccttgctgga tcgtgaaggc cgctcctagc 840
tgctctgaga agaagggcaa ctacgcctgc ctgctgagag aggaccaagg ctggtactgt 900
cagaacgccg gctccaccgt gtactacccc aacgagaagg actgcgagac aagaggcgac 960
cacgtgttct gcgatacctg cgctggcatc aatgtggccg agcagtccaa agagtgcaac 1020
atcaacatct ccaccaccaa ctatccctgc aaggtgtcca ccggcaggca ccctatttcc 1080
atggtggctc tgtctccact gggcgccctg gtggcttgtt ataagggcgt gtcctgctcc 1140
atcggctcca acagagtggg catcatcaag cagctgaaca agggctgcag ctacatcacc 1200
aaccaggacg ccgataccgt gaccatcgac aataccgtgt atcagctgtc caaggtggaa 1260
ggcgagcagc acgtgatcaa gggcagacct gtgtcctcca gcttcgaccc cgtgaagttc 1320
cctgaggatc agttcaacgt ggccctggac caggtgttcg agtccatcga gaactctcag 1380
gctctggtgg accagtccaa ccggattctg tctgccggct acatccccga ggctcctaga 1440
gatggacagg cctacgtcag aaaggacggc gaatgggtgc tgctgtctac ctttctcgga 1500
ggcctggtgc ctagaggctc tcaccaccat catcaccact ccgcttggtc ccatcctcag 1560
ttcgagaagt ga 1572

<210> SEQ ID NO 22
<211> LENGTH: 1572
<212> TYPE: DNA
<213> ORGANISM: Artificial Sequence
<220> FEATURE:
<223> OTHER INFORMATION: Synthetic

<400> SEQUENCE: 22

-continued

```
atgtcttgga aggtggtcat catcttctcc ctgctgatca cccctcagca cggcctgaaa     60

gagtcctacc tggaagagag ctgctccacc atcaccgagg gctacctgtc tgtgctgaga    120

accggctggt acaccaacgt gttcatgctg tgtgtgggcg acgtggaaaa cctgacctgt    180

gctgatggcc ccagcctgct gaaaacagag ctggacctga ccaagagcgc cctgagagaa    240

ctgaggaccg tgtctgcaga tcagctggcc agagaggaac agatcgagca gcctagacag    300

tccggatgtg gtgctggtgc tacagctggc gtggccattg ccaagaccat ccggctggaa    360

tctgaagtga ccgccatcaa gaatgccctg aaaaagacca acgaggccgt gtctaccctc    420

ggcaatggcg ttagagtgct ggccacaatg gtccgagagc tgtgcgactt cgtgtccaag    480

aatctgaccc gggccatcaa caagaacaag tgtgatatcg ccgacctgaa gatggccgtg    540

tccttcagcc agttcaaccg gcggttcctg aatgtcgtgc ggcagttctc tgacaacgcc    600

ggcatcaccc ctgccatcag cctggatctg atgaccgatg ccgagctggc tagagccgtg    660

tccaacatgc ctacctctgc cggccagatc aagctgatgc tcgagaacag agctatggtc    720

cgacggaaag gcttcggctt cctgatcggc gtgtacggct ctgacgtgat ctacatggtg    780

cagctgccta tcttcggcgt gatcgacacc ccttgctgga tcgtgaaggc cgctcctagc    840

tgctctgaga agaagggcaa ctacgcctgc ctgctgagag aggaccaagg ctggtactgt    900

cagaacgccg gctccaccgt gtactacccc aacgagaagg actgcgagac aagaggcgac    960

cacgtgttct gcgatacctg cgctggcatc aatgtggccg agcagtccaa agagtgcaac   1020

atcaacatct ccaccaccaa ctatccctgc aaggtgtcca ccggcagaca ccccatttcc   1080

atggtggctc tgtctccact gggtgccctg gtggcttgtt ataagggcgt gtcctgctcc   1140

atcggctcca acagagtggg catcatcaag cagctgaaca agggctgcag ctacatcacc   1200

aaccaggacg ccgataccgt gaccatcgac aataccgtgt atcagctgtc caaggtggaa   1260

ggcgagcagc acgtgatcaa gggcagacct gtgtcctcca gcttcgaccc cgtgaagttc   1320

cctgaggatc agttcaacgt ggccctggac caggtgttcg agtccatcga gaactctcag   1380

gctctggtgg accagtccaa cagatgctgt tccgccggct acatccccga ggctcctaga   1440

gatggacagg cctacgtcag aaaggacggc gaatgggtgc tgctgtctac ctttctcgga   1500

ggcctggtgc ctagaggctc tcaccaccat catcaccact ccgcttggtc ccatccacag   1560

ttcgagaagt ga                                                        1572
```

<210> SEQ ID NO 23
<211> LENGTH: 1590
<212> TYPE: DNA
<213> ORGANISM: Artificial Sequence
<220> FEATURE:
<223> OTHER INFORMATION: Synthetic

<400> SEQUENCE: 23

```
atgtcttgga aggtggtcat catcttctcc ctgctgatca cccctcagca cggcctgaaa     60

gagtcctacc tggaagagag ctgctccacc atcaccgagg gctacctgtc tgtgctgaga    120

accggctggt acaccaacgt gttcatgctg gaagtgggcg acgtggaaaa cctgacctgt    180

gctgatggcc ccagcctgat caagaccgag ctggacctga ccaagtctgc cctgagagaa    240

ctgaggaccg tgtctgccga tcagctggcc agagaggaac agatcgagca gcctagacag    300

tccggatgtg gtgctggtgc tacagctggc gtggccattg ccaagaccat ccggctggaa    360

tctgaagtga ccgcctggaa gaacgccctg aaaaagacca acgaggtggt gtctaccctc    420
```

-continued

```
ggcaacggcg tcagagtgct ggtcacaatg gtccgagagc tgaaggactt cgtgtccaag    480

aacctgacca gggctctgaa caagaacaag tgtgatatcg ccgacctgaa gatggccgtg    540

tctttcagcc agttcaaccg gcggttcctg aacgtcgtgc ggcagttctc tgataacgcc    600

ggcatcaccc ctgccatcag cctggatctg atgaccgatg ccgagctggc tagagccgtg    660

tccaacatgc ctacctctgc cggccagatc aagctgatgc tggaaaacag agccatggtc    720

cgacggaaag gcttcggctt tctgatcggc gtgtacggct cctccgtgat ctacatggtg    780

cagctgccta tcttcggcgt gatcgacacc ccttgctgga tcgtgaaggc cgctcctagc    840

tgctctgaga agaagggcaa ctacgcctgc ctgctgagag aggaccaagg ctggtactgt    900

cagaacgccg gctccaccgt gtactacccc aacgagaagg actgcgagac aagaggcgac    960

cacgtgttct gcgatacctg cgctggcatc aatgtggccg agcagtccaa agagtgcaac   1020

atcaacatct ccaccaccaa ctatccctgc aaggtgtcca ccggcaggca ccctatttcc   1080

atggtggctc tgtctccact gggcgccctg gtggcttgtt ataagggcgt gtcctgctcc   1140

atcggctcca acagagtggg catcatcaag cagctgaaca agggctgcag ctacatcacc   1200

aaccaggacg ccgataccgt gaccatcgac aataccgtgt atcagctgtc caaggtggaa   1260

ggcgagcagc acgtgatcaa gggcagacct gtgtcctcca gcttcgaccc cgtgaagttc   1320

cctgaggatc agttcaacgt ggccctggac caggtgttcg agtccatcga gaactctcag   1380

gctctggtgg accagtccaa ccggatcctg tcctctgccg agtctgctat cggcggctat   1440

atccccgagg ctcctagaga tggccaggcc tatgttcgga aggatggcga atgggtgctg   1500

ctgtctacct tcctcggagg cctggtgcct agaggctctc accaccatca tcaccactcc   1560

gcttggtccc atccacagtt cgagaagtga                                    1590
```

```
<210> SEQ ID NO 24
<211> LENGTH: 487
<212> TYPE: PRT
<213> ORGANISM: Artificial Sequence
<220> FEATURE:
<223> OTHER INFORMATION: Synthetic

<400> SEQUENCE: 24

Leu Lys Glu Ser Tyr Leu Glu Glu Ser Cys Ser Thr Ile Thr Glu Gly
1               5                   10                  15

Tyr Leu Ser Val Leu Arg Thr Gly Trp Tyr Thr Asn Val Phe Thr Leu
            20                  25                  30

Glu Val Gly Asp Val Glu Asn Leu Thr Cys Ala Asp Gly Pro Ser Leu
        35                  40                  45

Ile Lys Thr Glu Leu Asp Leu Thr Lys Ser Ala Leu Arg Glu Leu Arg
    50                  55                  60

Thr Val Ser Ala Asp Gln Leu Ala Arg Glu Glu Gln Ile Glu Gln Pro
65                  70                  75                  80

Arg Gln Ser Gly Cys Gly Ala Gly Ala Thr Ala Gly Val Ala Ile Ala
                85                  90                  95

Lys Thr Ile Arg Leu Glu Ser Glu Val Thr Ala Ile Lys Asn Ala Leu
            100                 105                 110

Lys Lys Thr Asn Glu Ala Val Ser Thr Leu Gly Asn Gly Val Arg Val
        115                 120                 125

Leu Ala Phe Ala Val Arg Glu Leu Lys Asp Phe Val Ser Lys Asn Leu
    130                 135                 140

Thr Arg Ala Leu Asn Lys Asn Lys Cys Asp Ile Ala Asp Leu Lys Met
145                 150                 155                 160
```

```
Ala Val Ser Phe Ser Gln Phe Asn Arg Arg Phe Leu Asn Val Val Arg
                165                 170                 175

Gln Phe Ser Asp Asn Ala Gly Ile Thr Pro Ala Ile Ser Leu Asp Leu
            180                 185                 190

Met Thr Asp Ala Glu Leu Ala Arg Ala Val Ser Asn Met Pro Thr Ser
        195                 200                 205

Ala Gly Gln Ile Lys Leu Met Leu Glu Asn Arg Ala Met Val Arg Arg
    210                 215                 220

Lys Gly Phe Gly Phe Leu Ile Gly Val Tyr Gly Ser Ser Val Ile Tyr
225                 230                 235                 240

Met Val Gln Leu Pro Ile Phe Gly Val Ile Asp Thr Pro Cys Trp Ile
                245                 250                 255

Val Lys Ala Ala Pro Ser Cys Ser Glu Lys Lys Gly Asn Tyr Ala Cys
            260                 265                 270

Leu Leu Arg Glu Asp Gln Gly Trp Tyr Cys Gln Asn Ala Gly Ser Thr
        275                 280                 285

Val Tyr Tyr Pro Asn Glu Lys Asp Cys Glu Thr Arg Gly Asp His Val
    290                 295                 300

Phe Cys Asp Thr Cys Ala Gly Ile Asn Val Ala Glu Gln Ser Lys Glu
305                 310                 315                 320

Cys Asn Ile Asn Ile Ser Thr Thr Asn Tyr Pro Cys Lys Val Ser Thr
                325                 330                 335

Gly Arg His Pro Ile Ser Met Val Ala Leu Ser Pro Leu Gly Ala Leu
            340                 345                 350

Val Ala Cys Tyr Lys Gly Val Ser Cys Ser Ile Gly Ser Asn Arg Val
        355                 360                 365

Gly Ile Ile Lys Gln Leu Asn Lys Gly Cys Ser Tyr Ile Thr Asn Gln
    370                 375                 380

Asp Ala Asp Thr Val Thr Ile Asp Asn Thr Val Tyr Gln Leu Ser Lys
385                 390                 395                 400

Val Glu Gly Glu Gln His Val Ile Lys Gly Arg Pro Val Ser Ser Ser
                405                 410                 415

Phe Asp Pro Val Lys Phe Pro Glu Asp Gln Phe Asn Val Ala Leu Asp
            420                 425                 430

Gln Val Phe Glu Ser Ile Glu Asn Ser Gln Ala Leu Val Asp Gln Ser
        435                 440                 445

Asn Arg Ile Leu Ser Ser Ala Glu Ser Ala Ile Gly Gly Tyr Ile Pro
    450                 455                 460

Glu Ala Pro Arg Asp Gly Gln Ala Tyr Val Arg Lys Asp Gly Glu Trp
465                 470                 475                 480

Val Leu Leu Ser Thr Phe Leu
                485


<210> SEQ ID NO 25
<211> LENGTH: 481
<212> TYPE: PRT
<213> ORGANISM: Artificial Sequence
<220> FEATURE:
<223> OTHER INFORMATION: Synthetic

<400> SEQUENCE: 25

Leu Lys Glu Ser Tyr Leu Glu Glu Ser Cys Ser Thr Ile Thr Glu Gly
1               5                   10                  15

Tyr Leu Ser Val Leu Arg Thr Gly Trp Tyr Thr Asn Val Phe Thr Leu
            20                  25                  30
```

-continued

```
Glu Val Gly Asp Val Glu Asn Leu Thr Cys Ala Asp Gly Pro Ser Leu
        35                  40                  45

Ile Lys Thr Glu Leu Asp Leu Thr Lys Ser Ala Leu Arg Glu Leu Arg
    50                  55                  60

Thr Val Ser Ala Asp Gln Leu Ala Arg Glu Glu Gln Ile Glu Gln Pro
65                  70                  75                  80

Arg Gln Ser Gly Cys Gly Ala Gly Ala Thr Ala Gly Val Ala Ile Ala
                85                  90                  95

Lys Thr Ile Arg Leu Glu Ser Glu Val Thr Ala Ile Lys Asn Ala Leu
            100                 105                 110

Lys Lys Thr Asn Glu Ala Val Ser Thr Leu Gly Asn Gly Val Arg Val
        115                 120                 125

Leu Ala Thr Ala Val Arg Glu Leu Lys Asp Phe Val Ser Lys Asn Leu
    130                 135                 140

Thr Arg Ala Ile Asn Lys Asn Lys Cys Asp Ile Ala Asp Leu Lys Met
145                 150                 155                 160

Ala Val Ser Phe Ser Gln Phe Asn Arg Arg Phe Leu Asn Val Val Arg
                165                 170                 175

Gln Phe Ser Asp Asn Ala Gly Ile Thr Pro Ala Ile Ser Leu Asp Leu
            180                 185                 190

Met Thr Asp Ala Glu Leu Ala Arg Ala Val Ser Asn Met Pro Thr Ser
        195                 200                 205

Ala Gly Gln Ile Lys Leu Met Leu Glu Asn Arg Ala Met Val Arg Arg
    210                 215                 220

Lys Gly Phe Gly Phe Leu Ile Gly Val Tyr Gly Ser Ser Val Ile Tyr
225                 230                 235                 240

Met Val Gln Leu Pro Ile Phe Gly Val Ile Asp Thr Pro Cys Trp Ile
                245                 250                 255

Val Lys Ala Ala Pro Ser Cys Ser Glu Lys Lys Gly Asn Tyr Ala Cys
            260                 265                 270

Leu Leu Arg Glu Asp Gln Gly Trp Tyr Cys Gln Asn Ala Gly Ser Thr
        275                 280                 285

Val Tyr Tyr Pro Asn Glu Lys Asp Cys Glu Thr Arg Gly Asp His Val
    290                 295                 300

Phe Cys Asp Thr Cys Ala Gly Ile Asn Val Ala Glu Gln Ser Lys Glu
305                 310                 315                 320

Cys Asn Ile Asn Ile Ser Thr Thr Asn Tyr Pro Cys Lys Val Ser Thr
                325                 330                 335

Gly Arg His Pro Ile Ser Met Val Ala Leu Ser Pro Leu Gly Ala Leu
            340                 345                 350

Val Ala Cys Tyr Lys Gly Val Ser Cys Ser Ile Gly Ser Asn Arg Val
        355                 360                 365

Gly Ile Ile Lys Gln Leu Asn Lys Gly Cys Ser Tyr Ile Thr Asn Gln
    370                 375                 380

Asp Ala Asp Thr Val Thr Ile Asp Asn Thr Val Tyr Gln Leu Ser Lys
385                 390                 395                 400

Val Glu Gly Glu Gln His Val Ile Lys Gly Arg Pro Val Ser Ser Ser
                405                 410                 415

Phe Asp Pro Val Lys Phe Pro Glu Asp Gln Phe Asn Val Ala Leu Asp
            420                 425                 430

Gln Val Phe Glu Ser Ile Glu Asn Ser Gln Ala Leu Val Asp Gln Ser
        435                 440                 445
```

```
Asn Arg Ile Leu Ser Ala Gly Tyr Ile Pro Glu Ala Pro Arg Asp Gly
    450                 455                 460

Gln Ala Tyr Val Arg Lys Asp Gly Glu Trp Val Leu Leu Ser Thr Phe
465                 470                 475                 480

Leu


<210> SEQ ID NO 26
<211> LENGTH: 481
<212> TYPE: PRT
<213> ORGANISM: Artificial Sequence
<220> FEATURE:
<223> OTHER INFORMATION: Synthetic

<400> SEQUENCE: 26

Leu Lys Glu Ser Tyr Leu Glu Glu Ser Cys Ser Thr Ile Thr Glu Gly
1               5                   10                  15

Tyr Leu Ser Val Leu Arg Thr Gly Trp Tyr Thr Asn Val Phe Met Leu
            20                  25                  30

Glu Val Gly Asp Val Glu Asn Leu Thr Cys Ala Asp Gly Pro Ser Leu
        35                  40                  45

Leu Lys Thr Glu Leu Asp Leu Thr Lys Ser Ala Leu Arg Asn Leu Arg
    50                  55                  60

Thr Val Ser Ala Asp Gln Leu Ala Arg Glu Glu Gln Ile Glu Gln Pro
65                  70                  75                  80

Arg Gln Ser Gly Cys Gly Ala Gly Ala Thr Ala Gly Val Ala Ile Ala
                85                  90                  95

Lys Thr Ile Arg Leu Glu Ser Glu Val Thr Ala Ile Lys Asn Ala Leu
            100                 105                 110

Lys Lys Thr Asn Glu Ala Val Ser Thr Leu Gly Asn Gly Val Arg Val
        115                 120                 125

Leu Ala Thr Met Val Arg Glu Leu Lys Asp Phe Val Ser Lys Asn Leu
    130                 135                 140

Thr Arg Ala Ile Asn Lys Asn Lys Cys Asp Ile Ala Asp Leu Lys Met
145                 150                 155                 160

Ala Val Ser Phe Ser Gln Phe Asn Arg Arg Phe Leu Asn Val Val Arg
                165                 170                 175

Gln Phe Ser Asp Asn Ala Gly Ile Thr Pro Ala Ile Ser Leu Asp Leu
            180                 185                 190

Met Thr Asp Ala Glu Leu Ala Arg Ala Val Ser Asn Met Pro Thr Ser
        195                 200                 205

Ala Gly Gln Ile Lys Leu Met Leu Glu Asn Arg Ala Met Val Arg Arg
    210                 215                 220

Lys Gly Phe Gly Ile Leu Ile Gly Val Tyr Gly Ser Ser Val Ile Tyr
225                 230                 235                 240

Met Val Gln Leu Pro Ile Phe Gly Val Ile Asp Thr Pro Cys Trp Ile
                245                 250                 255

Val Lys Ala Ala Pro Ser Cys Ser Glu Lys Lys Gly Asn Tyr Ala Cys
            260                 265                 270

Leu Leu Arg Glu Asp Gln Gly Trp Tyr Cys Gln Asn Ala Gly Ser Thr
        275                 280                 285

Val Tyr Tyr Pro Asn Glu Lys Asp Cys Glu Thr Arg Gly Asp His Val
    290                 295                 300

Phe Cys Asp Thr Cys Ala Gly Ile Asn Val Ala Glu Gln Ser Lys Glu
305                 310                 315                 320

Cys Asn Ile Asn Ile Ser Thr Thr Asn Tyr Pro Cys Lys Val Ser Thr
```

```
                325                 330                 335

Gly Arg His Pro Ile Ser Met Val Ala Leu Ser Pro Leu Gly Ala Leu
            340                 345                 350

Val Ala Cys Tyr Lys Gly Val Ser Cys Ser Ile Gly Ser Asn Arg Val
        355                 360                 365

Gly Ile Ile Lys Gln Leu Asn Lys Gly Cys Ser Tyr Ile Thr Asn Gln
    370                 375                 380

Asp Ala Asp Thr Val Thr Ile Asp Asn Thr Val Tyr Gln Leu Ser Lys
385                 390                 395                 400

Val Glu Gly Glu Gln His Val Ile Lys Gly Arg Pro Val Ser Ser Ser
                405                 410                 415

Phe Asp Pro Val Lys Phe Pro Glu Asp Gln Phe Asn Val Ala Leu Asp
            420                 425                 430

Gln Val Phe Glu Ser Ile Glu Asn Ser Gln Ala Leu Val Asp Gln Ser
        435                 440                 445

Asn Arg Ile Leu Ser Ala Gly Tyr Ile Pro Glu Ala Pro Arg Asp Gly
    450                 455                 460

Gln Ala Tyr Val Arg Lys Asp Gly Glu Trp Val Leu Leu Ser Thr Phe
465                 470                 475                 480

Leu


<210> SEQ ID NO 27
<211> LENGTH: 481
<212> TYPE: PRT
<213> ORGANISM: Artificial Sequence
<220> FEATURE:
<223> OTHER INFORMATION: Synthetic

<400> SEQUENCE: 27

Leu Lys Glu Ser Tyr Leu Glu Glu Ser Cys Ser Thr Ile Thr Glu Gly
1               5                   10                  15

Tyr Leu Ser Val Leu Arg Thr Gly Trp Tyr Thr Asn Val Phe Met Leu
            20                  25                  30

Cys Val Gly Asp Val Glu Asn Leu Thr Cys Ala Asp Gly Pro Ser Leu
        35                  40                  45

Leu Lys Thr Glu Leu Asp Leu Thr Lys Ser Ala Leu Arg Glu Leu Arg
    50                  55                  60

Thr Val Ser Ala Asp Gln Leu Ala Arg Glu Glu Gln Ile Glu Gln Pro
65                  70                  75                  80

Arg Gln Ser Gly Cys Gly Ala Gly Ala Thr Ala Gly Val Ala Ile Ala
                85                  90                  95

Lys Thr Ile Arg Leu Glu Ser Glu Val Thr Ala Ile Lys Asn Ala Leu
            100                 105                 110

Lys Lys Thr Asn Glu Ala Val Ser Thr Leu Gly Asn Gly Val Arg Val
        115                 120                 125

Leu Ala Thr Met Val Arg Glu Leu Cys Asp Phe Val Ser Lys Asn Leu
    130                 135                 140

Thr Arg Ala Ile Asn Lys Asn Lys Cys Asp Ile Ala Asp Leu Lys Met
145                 150                 155                 160

Ala Val Ser Phe Ser Gln Phe Asn Arg Arg Phe Leu Asn Val Val Arg
                165                 170                 175

Gln Phe Ser Asp Asn Ala Gly Ile Thr Pro Ala Ile Ser Leu Asp Leu
            180                 185                 190

Met Thr Asp Ala Glu Leu Ala Arg Ala Val Ser Asn Met Pro Thr Ser
        195                 200                 205
```

```
Ala Gly Gln Ile Lys Leu Met Leu Glu Asn Arg Ala Met Val Arg Arg
    210                 215                 220

Lys Gly Phe Gly Phe Leu Ile Gly Val Tyr Gly Ser Asp Val Ile Tyr
225                 230                 235                 240

Met Val Gln Leu Pro Ile Phe Gly Val Ile Asp Thr Pro Cys Trp Ile
                245                 250                 255

Val Lys Ala Ala Pro Ser Cys Ser Glu Lys Lys Gly Asn Tyr Ala Cys
            260                 265                 270

Leu Leu Arg Glu Asp Gln Gly Trp Tyr Cys Gln Asn Ala Gly Ser Thr
        275                 280                 285

Val Tyr Tyr Pro Asn Glu Lys Asp Cys Glu Thr Arg Gly Asp His Val
    290                 295                 300

Phe Cys Asp Thr Cys Ala Gly Ile Asn Val Ala Glu Gln Ser Lys Glu
305                 310                 315                 320

Cys Asn Ile Asn Ile Ser Thr Thr Asn Tyr Pro Cys Lys Val Ser Thr
                325                 330                 335

Gly Arg His Pro Ile Ser Met Val Ala Leu Ser Pro Leu Gly Ala Leu
            340                 345                 350

Val Ala Cys Tyr Lys Gly Val Ser Cys Ser Ile Gly Ser Asn Arg Val
        355                 360                 365

Gly Ile Ile Lys Gln Leu Asn Lys Gly Cys Ser Tyr Ile Thr Asn Gln
    370                 375                 380

Asp Ala Asp Thr Val Thr Ile Asp Asn Thr Val Tyr Gln Leu Ser Lys
385                 390                 395                 400

Val Glu Gly Glu Gln His Val Ile Lys Gly Arg Pro Val Ser Ser Ser
                405                 410                 415

Phe Asp Pro Val Lys Phe Pro Glu Asp Gln Phe Asn Val Ala Leu Asp
            420                 425                 430

Gln Val Phe Glu Ser Ile Glu Asn Ser Gln Ala Leu Val Asp Gln Ser
        435                 440                 445

Asn Arg Cys Cys Ser Ala Gly Tyr Ile Pro Glu Ala Pro Arg Asp Gly
    450                 455                 460

Gln Ala Tyr Val Arg Lys Asp Gly Glu Trp Val Leu Leu Ser Thr Phe
465                 470                 475                 480

Leu


<210> SEQ ID NO 28
<211> LENGTH: 487
<212> TYPE: PRT
<213> ORGANISM: Artificial Sequence
<220> FEATURE:
<223> OTHER INFORMATION: Synthetic

<400> SEQUENCE: 28

Leu Lys Glu Ser Tyr Leu Glu Glu Ser Cys Ser Thr Ile Thr Glu Gly
1               5                   10                  15

Tyr Leu Ser Val Leu Arg Thr Gly Trp Tyr Thr Asn Val Phe Met Leu
            20                  25                  30

Glu Val Gly Asp Val Glu Asn Leu Thr Cys Ala Asp Gly Pro Ser Leu
        35                  40                  45

Ile Lys Thr Glu Leu Asp Leu Thr Lys Ser Ala Leu Arg Glu Leu Arg
    50                  55                  60

Thr Val Ser Ala Asp Gln Leu Ala Arg Glu Glu Gln Ile Glu Gln Pro
65                  70                  75                  80
```

-continued

```
Arg Gln Ser Gly Cys Gly Ala Gly Ala Thr Ala Gly Val Ala Ile Ala
                85                  90                  95

Lys Thr Ile Arg Leu Glu Ser Glu Val Thr Ala Trp Lys Asn Ala Leu
            100                 105                 110

Lys Lys Thr Asn Glu Val Val Ser Thr Leu Gly Asn Gly Val Arg Val
        115                 120                 125

Leu Val Thr Met Val Arg Glu Leu Lys Asp Phe Val Ser Lys Asn Leu
    130                 135                 140

Thr Arg Ala Leu Asn Lys Asn Lys Cys Asp Ile Ala Asp Leu Lys Met
145                 150                 155                 160

Ala Val Ser Phe Ser Gln Phe Asn Arg Arg Phe Leu Asn Val Val Arg
                165                 170                 175

Gln Phe Ser Asp Asn Ala Gly Ile Thr Pro Ala Ile Ser Leu Asp Leu
            180                 185                 190

Met Thr Asp Ala Glu Leu Ala Arg Ala Val Ser Asn Met Pro Thr Ser
        195                 200                 205

Ala Gly Gln Ile Lys Leu Met Leu Glu Asn Arg Ala Met Val Arg Arg
    210                 215                 220

Lys Gly Phe Gly Phe Leu Ile Gly Val Tyr Gly Ser Ser Val Ile Tyr
225                 230                 235                 240

Met Val Gln Leu Pro Ile Phe Gly Val Ile Asp Thr Pro Cys Trp Ile
                245                 250                 255

Val Lys Ala Ala Pro Ser Cys Ser Glu Lys Lys Gly Asn Tyr Ala Cys
            260                 265                 270

Leu Leu Arg Glu Asp Gln Gly Trp Tyr Cys Gln Asn Ala Gly Ser Thr
        275                 280                 285

Val Tyr Tyr Pro Asn Glu Lys Asp Cys Glu Thr Arg Gly Asp His Val
    290                 295                 300

Phe Cys Asp Thr Cys Ala Gly Ile Asn Val Ala Glu Gln Ser Lys Glu
305                 310                 315                 320

Cys Asn Ile Asn Ile Ser Thr Thr Asn Tyr Pro Cys Lys Val Ser Thr
                325                 330                 335

Gly Arg His Pro Ile Ser Met Val Ala Leu Ser Pro Leu Gly Ala Leu
            340                 345                 350

Val Ala Cys Tyr Lys Gly Val Ser Cys Ser Ile Gly Ser Asn Arg Val
        355                 360                 365

Gly Ile Ile Lys Gln Leu Asn Lys Gly Cys Ser Tyr Ile Thr Asn Gln
    370                 375                 380

Asp Ala Asp Thr Val Thr Ile Asp Asn Thr Val Tyr Gln Leu Ser Lys
385                 390                 395                 400

Val Glu Gly Glu Gln His Val Ile Lys Gly Arg Pro Val Ser Ser Ser
                405                 410                 415

Phe Asp Pro Val Lys Phe Pro Glu Asp Gln Phe Asn Val Ala Leu Asp
            420                 425                 430

Gln Val Phe Glu Ser Ile Glu Asn Ser Gln Ala Leu Val Asp Gln Ser
        435                 440                 445

Asn Arg Ile Leu Ser Ser Ala Glu Ser Ala Ile Gly Gly Tyr Ile Pro
    450                 455                 460

Glu Ala Pro Arg Asp Gly Gln Ala Tyr Val Arg Lys Asp Gly Glu Trp
465                 470                 475                 480

Val Leu Leu Ser Thr Phe Leu
                485
```

<210> SEQ ID NO 29
<211> LENGTH: 27
<212> TYPE: PRT
<213> ORGANISM: Artificial Sequence
<220> FEATURE:
<223> OTHER INFORMATION: Synthetic

<400> SEQUENCE: 29

```
Gly Tyr Ile Pro Glu Ala Pro Arg Asn Gly Thr Ala Tyr Val Arg Lys
1               5                   10                  15

Asp Gly Glu Trp Val Leu Leu Ser Thr Phe Leu
            20                  25
```

<210> SEQ ID NO 30
<211> LENGTH: 27
<212> TYPE: PRT
<213> ORGANISM: Artificial Sequence
<220> FEATURE:
<223> OTHER INFORMATION: Synthetic

<400> SEQUENCE: 30

```
Gly Tyr Ile Pro Glu Ala Pro Arg Asp Gly Gln Ala Tyr Val Arg Lys
1               5                   10                  15

Asn Gly Thr Trp Val Leu Leu Ser Thr Phe Leu
            20                  25
```

<210> SEQ ID NO 31
<211> LENGTH: 27
<212> TYPE: PRT
<213> ORGANISM: Artificial Sequence
<220> FEATURE:
<223> OTHER INFORMATION: Synthetic

<400> SEQUENCE: 31

```
Gly Tyr Ile Pro Glu Ala Pro Arg Asp Gly Gln Ala Tyr Val Arg Lys
1               5                   10                  15

Asp Gly Asn Trp Thr Leu Leu Ser Thr Phe Leu
            20                  25
```

<210> SEQ ID NO 32
<211> LENGTH: 27
<212> TYPE: PRT
<213> ORGANISM: Artificial Sequence
<220> FEATURE:
<223> OTHER INFORMATION: Synthetic

<400> SEQUENCE: 32

```
Gly Tyr Ile Pro Glu Ala Pro Arg Asn Gly Thr Ala Tyr Val Arg Lys
1               5                   10                  15

Asn Gly Thr Trp Val Leu Leu Ser Thr Phe Leu
            20                  25
```

<210> SEQ ID NO 33
<211> LENGTH: 27
<212> TYPE: PRT
<213> ORGANISM: Artificial Sequence
<220> FEATURE:
<223> OTHER INFORMATION: Synthetic

<400> SEQUENCE: 33

```
Gly Tyr Ile Pro Glu Ala Pro Arg Asn Gly Thr Ala Tyr Val Arg Lys
1               5                   10                  15

Asp Gly Asn Trp Thr Leu Leu Ser Thr Phe Leu
            20                  25
```

-continued

<210> SEQ ID NO 34
<211> LENGTH: 4
<212> TYPE: PRT
<213> ORGANISM: Artificial Sequence
<220> FEATURE:
<223> OTHER INFORMATION: Synthetic

<400> SEQUENCE: 34

Ile Leu Ser Ala
1

<210> SEQ ID NO 35
<211> LENGTH: 4
<212> TYPE: PRT
<213> ORGANISM: Artificial Sequence
<220> FEATURE:
<223> OTHER INFORMATION: Synthetic

<400> SEQUENCE: 35

Cys Cys Ser Ala
1

<210> SEQ ID NO 36
<211> LENGTH: 18
<212> TYPE: PRT
<213> ORGANISM: Artificial Sequence
<220> FEATURE:
<223> OTHER INFORMATION: Synthetic

<400> SEQUENCE: 36

Cys Cys Lys Gln Thr Asn Glu Cys Cys Lys Asn Leu Glu Arg Ala Val
1 5 10 15

Ser Ala

<210> SEQ ID NO 37
<211> LENGTH: 18
<212> TYPE: PRT
<213> ORGANISM: Artificial Sequence
<220> FEATURE:
<223> OTHER INFORMATION: Synthetic

<400> SEQUENCE: 37

Cys Cys Arg Glu Leu Lys Glu Cys Cys Lys Asn Leu Glu Asn Ala Val
1 5 10 15

Ser Ala

<210> SEQ ID NO 38
<211> LENGTH: 18
<212> TYPE: PRT
<213> ORGANISM: Artificial Sequence
<220> FEATURE:
<223> OTHER INFORMATION: Artificial

<400> SEQUENCE: 38

Cys Cys Arg Glu Leu Lys Asp Cys Cys Lys Asn Leu Glu Asn Ala Val
1 5 10 15

Ser Ala

<210> SEQ ID NO 39
<211> LENGTH: 18
<212> TYPE: PRT
<213> ORGANISM: Artificial Sequence
<220> FEATURE:
<223> OTHER INFORMATION: Synthetic

<400> SEQUENCE: 39

Cys Cys Arg Glu Leu Lys Asp Cys Cys Lys Asn Leu Glu Arg Ala Val
1 5 10 15

Ser Ala

<210> SEQ ID NO 40
<211> LENGTH: 18
<212> TYPE: PRT
<213> ORGANISM: Artificial Sequence
<220> FEATURE:
<223> OTHER INFORMATION: Synthetic

<400> SEQUENCE: 40

Cys Cys Arg Glu Leu Lys Asp Cys Cys Lys Gln Leu Asn Lys Ala Val
1 5 10 15

Ser Ala

<210> SEQ ID NO 41
<211> LENGTH: 18
<212> TYPE: PRT
<213> ORGANISM: Artificial Sequence
<220> FEATURE:
<223> OTHER INFORMATION: Synthetic

<400> SEQUENCE: 41

Cys Cys Arg Glu Leu Lys Glu Cys Cys Lys Gln Leu Asn Lys Ala Val
1 5 10 15

Ser Ala

<210> SEQ ID NO 42
<211> LENGTH: 6
<212> TYPE: PRT
<213> ORGANISM: Artificial Sequence
<220> FEATURE:
<223> OTHER INFORMATION: Synthetic

<400> SEQUENCE: 42

Leu Val Pro Arg Gly Ser
1 5

<210> SEQ ID NO 43
<211> LENGTH: 7
<212> TYPE: PRT
<213> ORGANISM: Artificial Sequence
<220> FEATURE:
<223> OTHER INFORMATION: Synthetic

<400> SEQUENCE: 43

Glu Asn Leu Tyr Phe Gln Gly
1 5

<210> SEQ ID NO 44
<211> LENGTH: 4
<212> TYPE: PRT
<213> ORGANISM: Artificial Sequence
<220> FEATURE:
<223> OTHER INFORMATION: Synthetic

<400> SEQUENCE: 44

Ile Glu Gly Arg
1

<210> SEQ ID NO 45
<211> LENGTH: 17

<212> TYPE: PRT
<213> ORGANISM: Artificial Sequence
<220> FEATURE:
<223> OTHER INFORMATION: Synthetic

<400> SEQUENCE: 45

Cys Cys Lys Gln Thr Asn Glu Cys Cys Lys Asn Leu Glu Arg Ala Val
1 5 10 15

Ser

<210> SEQ ID NO 46
<211> LENGTH: 17
<212> TYPE: PRT
<213> ORGANISM: Artificial Sequence
<220> FEATURE:
<223> OTHER INFORMATION: Synthetic

<400> SEQUENCE: 46

Cys Cys Lys Gln Thr Asn Glu Cys Cys Lys Asn Leu Glu Arg Ala Val
1 5 10 15

Ser

<210> SEQ ID NO 47
<211> LENGTH: 17
<212> TYPE: PRT
<213> ORGANISM: Artificial Sequence
<220> FEATURE:
<223> OTHER INFORMATION: Synthetic

<400> SEQUENCE: 47

Cys Cys Lys Gln Thr Asn Glu Cys Cys Lys Asn Leu Glu Arg Ala Val
1 5 10 15

Ser

<210> SEQ ID NO 48
<211> LENGTH: 17
<212> TYPE: PRT
<213> ORGANISM: Artificial Sequence
<220> FEATURE:
<223> OTHER INFORMATION: Synthetic

<400> SEQUENCE: 48

Cys Cys Arg Glu Leu Lys Glu Cys Cys Lys Asn Leu Glu Asn Ala Val
1 5 10 15

Ser

<210> SEQ ID NO 49
<211> LENGTH: 17
<212> TYPE: PRT
<213> ORGANISM: Artificial Sequence
<220> FEATURE:
<223> OTHER INFORMATION: Synthetic

<400> SEQUENCE: 49

Cys Cys Arg Glu Leu Lys Glu Cys Cys Lys Asn Leu Glu Asn Ala Val
1 5 10 15

Ser

<210> SEQ ID NO 50
<211> LENGTH: 17
<212> TYPE: PRT
<213> ORGANISM: Artificial Sequence
<220> FEATURE:
<223> OTHER INFORMATION: Synthetic

<400> SEQUENCE: 50

Cys Cys Arg Glu Leu Lys Glu Cys Cys Lys Asn Leu Glu Asn Ala Val
1 5 10 15

Ser

<210> SEQ ID NO 51
<211> LENGTH: 540
<212> TYPE: PRT
<213> ORGANISM: Artificial Sequence
<220> FEATURE:
<223> OTHER INFORMATION: Synthetic

<400> SEQUENCE: 51

Met Ser Trp Lys Val Val Ile Ile Phe Ser Leu Leu Ile Thr Pro Gln
1 5 10 15

His Gly Leu Lys Glu Ser Tyr Leu Glu Glu Ser Cys Ser Thr Ile Thr
20 25 30

Glu Gly Tyr Leu Ser Val Leu Arg Thr Gly Trp Tyr Thr Asn Val Phe
35 40 45

Thr Leu Glu Val Gly Asp Val Glu Asn Leu Thr Cys Ala Asp Gly Pro
50 55 60

Ser Leu Ile Lys Thr Glu Leu Asp Leu Thr Lys Ser Ala Leu Arg Glu
65 70 75 80

Leu Arg Thr Val Ser Ala Asp Gln Leu Ala Arg Glu Glu Gln Ile Glu
85 90 95

Asn Pro Arg Gln Ser Arg Phe Val Leu Gly Ala Ile Ala Leu Gly Val
100 105 110

Cys Thr Ala Ala Ala Val Thr Ala Gly Val Ala Ile Ala Lys Thr Ile
115 120 125

Arg Leu Glu Ser Glu Val Thr Ala Ile Lys Asn Ala Leu Lys Lys Thr
130 135 140

Asn Glu Ala Val Ser Thr Leu Gly Asn Gly Val Arg Val Leu Ala Phe
145 150 155 160

Ala Val Arg Glu Leu Lys Asp Phe Val Ser Lys Asn Leu Thr Arg Ala
165 170 175

Leu Asn Lys Asn Lys Cys Asp Ile Ala Asp Leu Lys Met Ala Val Ser
180 185 190

Phe Ser Gln Phe Asn Arg Arg Phe Leu Asn Val Val Arg Gln Phe Ser
195 200 205

Asp Asn Ala Gly Ile Thr Pro Ala Ile Ser Leu Asp Leu Met Thr Asp
210 215 220

Ala Glu Leu Ala Arg Ala Val Ser Asn Met Pro Thr Ser Ala Gly Gln
225 230 235 240

Ile Lys Leu Met Leu Glu Asn Arg Ala Met Val Arg Arg Lys Gly Phe
245 250 255

Gly Phe Leu Ile Gly Val Tyr Gly Ser Ser Val Ile Tyr Met Val Gln
260 265 270

Leu Pro Ile Phe Gly Val Ile Asp Thr Pro Cys Trp Ile Val Lys Ala
275 280 285

Ala Pro Ser Cys Ser Glu Lys Lys Gly Asn Tyr Ala Cys Leu Leu Arg
290 295 300

Glu Asp Gln Gly Trp Tyr Cys Gln Asn Ala Gly Ser Thr Val Tyr Tyr
305 310 315 320

Pro Asn Glu Lys Asp Cys Glu Thr Arg Gly Asp His Val Phe Cys Asp

-continued

```
                325                 330                 335

Thr Ala Cys Gly Ile Asn Val Ala Glu Gln Ser Lys Glu Cys Asn Ile
            340                 345                 350

Asn Ile Ser Thr Thr Asn Tyr Pro Cys Lys Val Ser Thr Gly Arg His
        355                 360                 365

Pro Ile Ser Met Val Ala Leu Ser Pro Leu Gly Ala Leu Val Ala Cys
    370                 375                 380

Tyr Lys Gly Val Ser Cys Ser Ile Gly Ser Asn Arg Val Gly Ile Ile
385                 390                 395                 400

Lys Gln Leu Asn Lys Gly Cys Ser Tyr Ile Thr Asn Gln Asp Ala Asp
                405                 410                 415

Thr Val Thr Ile Asp Asn Thr Val Tyr Gln Leu Ser Lys Val Glu Gly
            420                 425                 430

Glu Gln His Val Ile Lys Gly Arg Pro Val Ser Ser Ser Phe Asp Pro
        435                 440                 445

Val Lys Phe Pro Glu Asp Gln Phe Asn Val Ala Leu Asp Gln Val Phe
    450                 455                 460

Glu Ser Ile Glu Asn Ser Gln Ala Leu Val Asp Gln Ser Asn Arg Ile
465                 470                 475                 480

Leu Ser Ser Ala Glu Ser Ala Ile Gly Gly Tyr Ile Pro Glu Ala Pro
                485                 490                 495

Arg Asp Gly Gln Ala Tyr Val Arg Lys Asp Gly Glu Trp Val Leu Leu
            500                 505                 510

Ser Thr Phe Leu Gly Gly Leu Val Pro Arg Gly Ser His His His His
        515                 520                 525

His His Ser Ala Trp Ser His Pro Gln Phe Glu Lys
    530                 535                 540
```

<210> SEQ ID NO 52
<211> LENGTH: 1623
<212> TYPE: DNA
<213> ORGANISM: Artificial Sequence
<220> FEATURE:
<223> OTHER INFORMATION: Synthetic

<400> SEQUENCE: 52

```
atgtcttgga aggtggtcat catcttctcc ctgctgatca cccctcagca cggcctgaaa      60

gagtcctacc tggaagagag ctgctccacc atcaccgagg gctacctgtc tgtgctgaga     120

accggctggt acaccaacgt gttcaccctg gaagtgggcg acgtggaaaa cctgacctgt     180

gctgatggcc ccagcctgat caagaccgag ctggacctga ccaagtctgc cctgagagaa     240

ctgaggaccg tgtctgccga tcagctggcc agagaggaac agatcgagaa ccctcggcag     300

tccagattcg tgctgggagc tattgctctg ggcgtgtgta cagccgctgc tgtgacagct     360

ggtgtcgcta tcgccaagac catccggctg gaatctgaag tgaccgccat caagaacgcc     420

ctgaaaaaga ccaacgaggc cgtgtccaca ctcggcaatg gcgttagagt gctggccttt     480

gctgtgcgcg agctgaagga cttcgtgtcc aagaacctga ccagggctct gaacaagaac     540

aagtgtgata tcgccgacct gaagatggcc gtgtctttca gccagttcaa ccggcggttc     600

ctgaacgtcg tgcggcagtt ctctgataac gccggcatca cccctgccat cagcctggat     660

ctgatgaccg atgccgagct ggctagagcc gtgtctaaca tgcctacctc tgccggccag     720

atcaagctga tgctggaaaa cagagccatg gtccgacgga aaggcttcgg ctttctgatc     780

ggcgtgtacg gctcctccgt gatctacatg gtgcagctgc ctatcttcgg cgtgatcgac     840
```

```
acccccttgct ggatcgtgaa ggccgctcct agctgctctg agaagaaggg caactacgcc    900

tgcctgctga gagaggacca aggctggtac tgtcagaacg ccggctccac cgtgtactac    960

cccaacgaga aggactgcga gacaagaggc gaccacgtgt tctgcgatac cgcctgtggc   1020

atcaatgtgg ccgagcagtc caaagagtgc aacatcaaca tctccaccac caactatccc   1080

tgcaaggtgt ccaccggcag gcaccctatt tccatggtgg ctctgtctcc actgggcgcc   1140

ctggtggctt gttataaggg cgtgtcctgc tccatcggct ccaacagagt gggcatcatc   1200

aagcagctga acaagggctg cagctacatc accaaccagg acgccgatac cgtgaccatc   1260

gacaataccg tgtatcagct gtccaaggtg gaaggcgagc agcacgtgat caagggcaga   1320

cctgtgtcct ccagcttcga ccccgtgaag ttccctgagg atcagttcaa cgtggccctg   1380

gaccaggtgt tcgagtccat cgagaactct caggctctgg tggaccagtc caaccggatc   1440

ctgtcctctg ccgagtctgc tatcggcggc tatatccccg aggctcctag agatggccag   1500

gcctatgttc ggaaggatgg cgaatgggtg ctgctgtcta ccttcctcgg aggcctggtg   1560

cctagaggct ctcaccacca tcatcaccac tccgcttggt cccatccaca gttcgagaag   1620

tga                                                                 1623
```

<210> SEQ ID NO 53
<211> LENGTH: 538
<212> TYPE: PRT
<213> ORGANISM: Artificial Sequence
<220> FEATURE:
<223> OTHER INFORMATION: Synthetic

<400> SEQUENCE: 53

```
Met Ser Trp Lys Val Val Ile Ile Phe Ser Leu Leu Ile Thr Pro Gln
1               5                   10                  15

His Gly Leu Lys Glu Ser Tyr Leu Glu Glu Ser Cys Ser Thr Ile Thr
            20                  25                  30

Glu Gly Tyr Leu Ser Val Leu Arg Thr Gly Trp Tyr Thr Asn Val Phe
        35                  40                  45

Thr Leu Glu Val Gly Asp Val Glu Asn Leu Thr Cys Ala Asp Gly Pro
    50                  55                  60

Ser Leu Ile Lys Thr Glu Leu Asp Leu Thr Lys Ser Ala Leu Arg Glu
65                  70                  75                  80

Leu Arg Thr Val Ser Ala Asp Gln Leu Ala Arg Glu Glu Gln Ile Glu
                85                  90                  95

Asn Pro Arg Gln Ser Lys Lys Arg Lys Arg Arg Val Ala Thr Ala Ala
            100                 105                 110

Ala Val Thr Ala Gly Val Ala Ile Ala Lys Thr Ile Arg Leu Glu Ser
        115                 120                 125

Glu Val Thr Ala Ile Lys Asn Ala Leu Lys Lys Thr Asn Glu Ala Val
    130                 135                 140

Ser Thr Leu Gly Asn Gly Val Arg Val Leu Ala Thr Ala Val Arg Glu
145                 150                 155                 160

Leu Lys Asp Phe Val Ser Lys Asn Leu Thr Arg Ala Ile Asn Lys Asn
                165                 170                 175

Lys Cys Asp Ile Ala Asp Leu Lys Met Ala Val Ser Phe Ser Gln Phe
            180                 185                 190

Asn Arg Arg Phe Leu Asn Val Val Arg Gln Phe Ser Asp Asn Ala Gly
        195                 200                 205

Ile Thr Pro Ala Ile Ser Leu Asp Leu Met Thr Asp Ala Glu Leu Ala
    210                 215                 220
```

```
Arg Ala Val Ser Asn Met Pro Thr Ser Ala Gly Gln Ile Lys Leu Met
225                 230                 235                 240

Leu Glu Asn Arg Ala Met Val Arg Arg Lys Gly Phe Gly Phe Leu Ile
                245                 250                 255

Gly Val Tyr Gly Ser Ser Val Ile Tyr Met Val Gln Leu Pro Ile Phe
            260                 265                 270

Gly Val Ile Asp Thr Pro Cys Trp Ile Val Lys Ala Ala Pro Ser Cys
        275                 280                 285

Ser Glu Lys Lys Gly Asn Tyr Ala Cys Leu Leu Arg Glu Asp Gln Gly
    290                 295                 300

Trp Tyr Cys Gln Asn Ala Gly Ser Thr Val Tyr Tyr Pro Asn Glu Lys
305                 310                 315                 320

Asp Cys Glu Thr Arg Gly Asp His Val Phe Cys Asp Thr Ala Ala Gly
                325                 330                 335

Ile Asn Val Ala Glu Gln Ser Lys Glu Cys Asn Ile Asn Ile Ser Thr
            340                 345                 350

Thr Asn Tyr Pro Cys Lys Val Ser Thr Gly Arg His Pro Ile Ser Met
        355                 360                 365

Val Ala Leu Ser Pro Leu Gly Ala Leu Val Ala Cys Tyr Lys Gly Val
    370                 375                 380

Ser Cys Ser Ile Gly Ser Asn Arg Val Gly Ile Ile Lys Gln Leu Asn
385                 390                 395                 400

Lys Gly Cys Ser Tyr Ile Thr Asn Gln Asp Ala Asp Thr Val Thr Ile
                405                 410                 415

Asp Asn Thr Val Tyr Gln Leu Ser Lys Val Glu Gly Glu Gln His Val
            420                 425                 430

Ile Lys Gly Arg Pro Val Ser Ser Ser Phe Asp Pro Val Lys Phe Pro
        435                 440                 445

Glu Asp Gln Phe Asn Val Ala Leu Asp Gln Val Phe Glu Ser Ile Glu
    450                 455                 460

Asn Ser Gln Ala Leu Val Asp Gln Ser Asn Arg Ile Leu Ser Ser Ala
465                 470                 475                 480

Glu Lys Gly Asn Thr Ser Gly Arg Glu Asn Leu Tyr Phe Gln Gly Gly
                485                 490                 495

Gly Gly Ser Gly Tyr Ile Pro Glu Ala Pro Arg Asp Gly Gln Ala Tyr
            500                 505                 510

Val Arg Lys Asp Gly Glu Trp Val Leu Leu Ser Thr Phe Leu Gly Gly
        515                 520                 525

Ile Glu Gly Arg His His His His His His
    530                 535
```

<210> SEQ ID NO 54
<211> LENGTH: 1617
<212> TYPE: DNA
<213> ORGANISM: Artificial Sequence
<220> FEATURE:
<223> OTHER INFORMATION: Synthetic

<400> SEQUENCE: 54

```
atgtcctgga aggtcgtgat catcttctcc ctgctgatca ccccccagca cggcctgaaa      60

gagtcctacc tggaagagag ctgctccacc atcaccgagg gctacctgtc tgtgctgcgg     120

accggctggt acaccaacgt gttcaccctg gaagtgggcg acgtggaaaa cctgacctgc     180

gccgatggcc ccagcctgat caagaccgag ctggacctga ccaagtccgc cctgcgggaa     240
```

-continued

```
ctgagaaccg tgtctgccga tcagctggcc agagaggaac agatcgagaa cccccggcag    300

tccaagaaac ggaagcggag agtggccacc gccgctgctg tgacagctgg cgtggccatt    360

gccaagacca tccggctgga atccgaagtg accgccatca agaacgccct gaaaaagacc    420

aacgaggccg tgtctaccct gggcaatggc gtgcgagtgc tggctacagc tgtgcgcgag    480

ctgaaggact tcgtgtccaa gaacctgacc cgggccatca acaagaacaa gtgtgatatc    540

gccgacctga agatggccgt gtcctttagc cagttcaacc ggcggttcct gaacgtcgtg    600

cggcagttct ctgacaacgc cggcatcacc cctgccatct ccctggatct gatgaccgac    660

gccgagctgg ctagagccgt gtccaacatg cctacctctg ccggccagat caagctgatg    720

ctggaaaacc gggccatggt gcgacggaag ggcttcggct ttctgatcgg cgtgtacggc    780

tcctccgtga tctacatggt gcagctgcct atcttcggcg tgatcgacac cccctgctgg    840

atcgtgaagg ccgctcctag ctgctccgag aagaagggca actacgcctg cctgctgaga    900

gaggaccagg gctggtactg tcagaacgcc ggctccaccg tgtactaccc caacgagaag    960

gactgcgaga cacggggcga ccacgtgttc tgtgataccg ctgctggcat caacgtggcc   1020

gagcagtcca aagagtgcaa catcaacatc tccaccacca actacccctg caaggtgtcc   1080

accggcaggc accccatctc tatggtggcc ctgtctcctc tgggcgccct ggtggcttgt   1140

tacaagggcg tgtcctgctc catcggctcc aacagagtgg gcatcatcaa gcagctgaac   1200

aagggctgca gctacatcac caaccaggac gccgacaccg tgaccatcga caataccgtg   1260

tatcagctgt ccaaggtgga aggcgagcag cacgtgatca agggcagacc cgtgtcctcc   1320

agcttcgacc ccgtgaagtt ccccgaggat cagttcaatg tggccctgga ccaggtgttc   1380

gagtccatcg agaactccca ggctctggtg gaccagtcca accggatcct gtcctctgcc   1440

gagaagggaa acacctccgg cagagagaac ctgtattttc aaggcggcgg aggctccggc   1500

tacatccctg aggctcctag agatggccag gcctacgtgc ggaaggatgg cgaatgggtg   1560

ctgctgtcca ccttcctggg cggcatcgag ggcagacacc accatcatca ccactga      1617
```

<210> SEQ ID NO 55
<211> LENGTH: 11
<212> TYPE: PRT
<213> ORGANISM: Artificial Sequence
<220> FEATURE:
<223> OTHER INFORMATION: Synthetic

<400> SEQUENCE: 55

```
Lys Leu Lys Leu Leu Leu Leu Leu Lys Leu Lys
1               5                   10
```

<210> SEQ ID NO 56
<211> LENGTH: 26
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(1)
<223> OTHER INFORMATION: i
<220> FEATURE:
<221> NAME/KEY: modified_base
<222> LOCATION: (3)..(3)
<223> OTHER INFORMATION: i
<220> FEATURE:
<221> NAME/KEY: modified_base
<222> LOCATION: (5)..(5)
<223> OTHER INFORMATION: i
<220> FEATURE:

-continued

```
<221> NAME/KEY: modified_base
<222> LOCATION: (7)..(7)
<223> OTHER INFORMATION: i
<220> FEATURE:
<221> NAME/KEY: modified_base
<222> LOCATION: (9)..(9)
<223> OTHER INFORMATION: i
<220> FEATURE:
<221> NAME/KEY: modified_base
<222> LOCATION: (11)..(11)
<223> OTHER INFORMATION: i
<220> FEATURE:
<221> NAME/KEY: modified_base
<222> LOCATION: (13)..(13)
<223> OTHER INFORMATION: i
<220> FEATURE:
<221> NAME/KEY: modified_base
<222> LOCATION: (15)..(15)
<223> OTHER INFORMATION: i
<220> FEATURE:
<221> NAME/KEY: modified_base
<222> LOCATION: (17)..(17)
<223> OTHER INFORMATION: i
<220> FEATURE:
<221> NAME/KEY: modified_base
<222> LOCATION: (19)..(19)
<223> OTHER INFORMATION: i
<220> FEATURE:
<221> NAME/KEY: modified_base
<222> LOCATION: (21)..(21)
<223> OTHER INFORMATION: i
<220> FEATURE:
<221> NAME/KEY: modified_base
<222> LOCATION: (23)..(23)
<223> OTHER INFORMATION: i
<220> FEATURE:
<221> NAME/KEY: modified_base
<222> LOCATION: (25)..(25)
<223> OTHER INFORMATION: i

<400> SEQUENCE: 56

ncncncncnc ncncncncnc ncncnc                                    26
```

SUBUNIT VACCINE FOR TREATMENT OR PREVENTION OF A RESPIRATORY TRACT INFECTION

RELATED APPLICATION

This application is a national stage filing under 35 U.S.C. 371 of International Patent Application Serial No. PCT/EP2020/063973, filed May 19, 2020, the content of which is incorporated by reference herein in its entirety.

REFERENCE TO A SEQUENCE LISTING SUBMITTED AS A TEXT FILE

The instant application contains a Sequence Listing which has been submitted in ASCII format and is hereby incorporated by reference in its entirety. Said ASCII copy, created on Jun. 25, 2024, is named I042270140US00-SUBSEQ-NTJ and is 114,053 bytes in size.

FIELD OF THE INVENTION

The present invention relates to modified metapneumovirus (hMPV) F proteins, stabilized in the pre-fusion conformation. It also relates to immunogenic compositions (vaccines) comprising these proteins for preventing and/or treating human subjects against respiratory tract infections.

BACKGROUND OF THE INVENTION

Human metapneumovirus (hMPV) is a leading cause of acute respiratory tract infections in young children (0-4 years), immunocompromised patients and in elderly that can be fatal for these categories of patients (Schildgen et al. 2011. *Clinical Microbiology Reviews* 24(4): 734-54). Despite intensive efforts, currently there are no licensed vaccines or antivirals to prevent or treat hMPV infection. Among several vaccination strategies investigated, a subunit vaccine containing a viral protein, especially the hMPV F protein, is the most promising (Melero & Mas. 2015. *Virus Res.* 209: 128-35).

hMPV is an enveloped, single-stranded RNA virus of the genus Pneumovirus of the family Paramyxoviridae. The hMPV genome consists of eight genes encoding nine proteins, including three surface glycoproteins F, G and SH. Protection against hMPV is afforded mainly by neutralizing antibodies directed against the fusion (F) glycoprotein, which is highly conserved between different genotypes and shares similarities to other paramyxoviruses (see van den Hoogen et al. 2004. *Emerging Infectious Diseases* 10(4): 658-66; van den Hoogen et al. 2002. *Virology* 295(1): 119-32).

Paramyxoviral F protein is a type I integral membrane protein that spans the membrane once and contains at its N-terminus a signal peptide, which targets the ectodomain to the extracellular membrane. At the C-terminus, a hydrophobic stop-transfer domain (TM domain) anchors the protein in the membrane, leaving a short cytoplasmic tail (see FIG. 1).

The native F protein is synthesized as an inactive precursor, designated F0 after a cleavage of the signal peptide (Yin et al. 2006. Nature 439 (7072): 38-44; Yin et al. 2005. *Proc. Nat. Acad. Sci.* 102(26): 9288-93; Russell et al. 1994. *Virology* 199(1): 160-8). To become biologically active, F0 is processed by a host protease generating two chains called F1 and F2, which remain covalently linked by disulfide bonds (Schowalter et al. 2006. *Journal of Virology* 80(22): 10931-41; Biacchesi et al. 2006. *Journal of Virology* 80(12):

5798-806; Yun et al. 2015. *Scientific Reports* 5: 15584). Three F1-F2 heterodimers form a mature F protein that is incorporated into the virion envelope in a metastable pre-fusion conformation (Battles et al. 2017. *Nat. Commun.* 8(1): 1528) and mediates fusion of the virion envelope and the host cell plasma membrane. During the fusion process, the F protein undergoes irreversible refolding from the labile pre-fusion conformation to the stable post-fusion conformation (see FIG. 2).

Neutralizing antibodies specifically recognizing the pre-fusion hMPV F protein structure were found in human sera (Wen et al. 20012. *Nat. Struct. Mol. Biol.* 19: 461-463; Ngwuta et al. 2015. *Science Translational Medicine* 7(309): 309; Rossey et al. 2018. *Trends in Microbiology* 26(3): 209-19) indicating that the pre-fusion F protein could be a favorable vaccine candidate (Melero & Mas. 2015. *Virus Res.* 209: 128-35). One clear disadvantage of the pre-fusion over post-fusion F protein conformation is its instability. Previous attempts to produce stabilized pre-fusion F protein employed thorough structural analysis and computer modeling. In particular, one group described design of a highly stable pre-fusion RSV F protein, capable to provide protective response in rats (see Krarup et al. 2015. *Nat. Commun.* 6: 8143). Another group disclosed construction of stabilized pre-fusion forms of the hMPV F protein, which elicited neutralizing antibodies in mice immunized with those proteins (see WO2016/103238).

Crystal structures of the F protein in pre-fusion and post-fusion conformations were determined for hMPV, RSV and other paramyxoviruses (see e.g. Battles et al. 2017. *Nat. Commun.* 8(1): 1528). In spite of general structural similarities, it was revealed that the pre-fusion hMPV F protein possesses unique structural features that confer substantial functional and immunological differences between the F proteins of hMPV and RSV.

Despite significant progress in understanding a mechanism of action, structure and immunogenic properties of the hMPV F protein, no F protein based vaccine is on the market. Therefore, the objective of this invention is to provide novel modified pre-fusion hMPV F protein candidates for development of a human vaccine against a respiratory tract infection.

SUMMARY OF THE INVENTION

The present disclosure provides recombinant immunogenic human metapneumovirus (hMPV) F proteins and fragments thereof (herein referred to as the hMPV F proteins) capable to elicit neutralizing antibodies and protect against hMPV infection. A native coding sequence of the hMPV F protein was modified to generate stable pre-fusion conformation. Such modifications were designed based on three-dimensional (3D) homology models included as a part of the present invention. The invention further includes methods of producing the recombinant immunogenic proteins and methods of using the immunogenic proteins for prevention and/or treatment of hMPV infection in humans.

In one aspect, the present disclosure provides a modified hMPV F protein or a fragment thereof, stabilized in the pre-fusion conformation, comprising a single-chain polypeptide composed of an F2 domain, a heterologous peptide linker and an F1 domain lacking a fusion peptide (FP), wherein the linker is positioned between the F2 and F1 domains and contains one or more cysteine residue(s) each of which forms a non-natural disulfide bond with a cysteine residue present in the F1 domain.

In one embodiment, the single-chain F protein comprises F2 domain and F1 domains connected so that the C-terminus of F2 is proximal to the N-terminus of F1. A protease cleavage site between F2 and F1 may be mutated to eliminate the cleavage of the protein precursor. In some embodiments, the F1 domain may be a truncated F1 domain, e.g. so that it lacks the fusion peptide (FP) spanning the amino acid residues at positions 103-118 of the native hMPV F protein sequence of SEQ ID NO: 1, corresponding to residues 1 to 16 of the native F1 domain sequence of SEQ ID NO: 3. Thus, the F1 domain may comprise a fragment corresponding to residues 119 to 539 of SEQ ID NO: 1 or residues 17 to 437 of SEQ ID NO: 3. In some embodiments, the single-chain polypeptide may comprise a fragment of the F1 domain corresponding to residues 119 to 490 of SEQ ID NO: 1 or residues 17 to 338 of SEQ ID NO: 3, which does not contain an anchor transmembrane (TM) domain and a cytoplasmic tail at its C-terminus. Additionally, the F1 and F2 domains may be joined via a heterologous peptide linker containing e.g. five residues comprising at least one cysteine residue, preferably the linker of SEQ ID NO: 4.

In yet one embodiment, the single-chain F protein of the present invention has a stable pre-fusion conformation. On one side, the pre-fusion conformation is stabilized by abolished protease cleavage between F1 and F2 domains and lack of the free N-terminus of F1. Another feature that confers stabilization is the presence of at least one additional (including a non-natural) disulfide bond, which fixes the HRA domain inside the cavity formed by trimerization (see FIG. 3). In one embodiment, a non-natural disulfide bond can be formed between a cysteine residue of the heterologous peptide linker inserted between F2 and F1 and a cysteine residue located in the F1 domain, preferably in the C-terminal region thereof and located within said cavity. For instance, a non-natural disulfide bond can be formed between a cysteine residue in the peptide linker and a non-natural cysteine residue present in the F1 domain at position 338 of the native hMPV F protein sequence of SEQ ID NO: 1, corresponding to position 236 of the native F1 domain sequence of SEQ ID NO: 3. In such embodiments, the F1 domain present in the single-chain F protein (e.g. a truncated F1 domain lacking the fusion peptide of residues 1-16 of SEQ ID NO: 3) may comprise a mutation such as A236C in the sequence of SEQ ID NO: 3 (corresponding to A338C in SEQ ID NO: 1). The cysteine residue in the peptide linker may, for example, be immediately adjacent to the F2 domain, e.g. may be the first residue at the N-terminus of the heterologous linker and adjacent to the C-terminus of the F2 domain. For instance, the cysteine residue in the peptide linker may be present in the recombinant polypeptide at a position equivalent to residue 103 of SEQ ID NO: 1.

In a further embodiment, the single-chain F protein may comprise one or more additional modification(s) that compensate for an altered geometry of the single-chain-containing F trimer. Preferably, said modification(s) is(are) substitution(s) at positions corresponding to positions 49, 51, 67, 80, 97, 137, 147, 159, 160, 161, 166, 177, 185, 258, 266, 294, 480 and/or 481 of the native hMPV F protein sequence of SEQ ID NO: 1. In particular, an asparagine at position 97 can be substituted for a glutamate (N97Q) or an alanine at position 185 can be substituted for a proline (A185P). Thus, the recombinant polypeptide may comprise the F2 domain comprising one or more substitution(s) at positions 31, 33, 49, 62 and/or 79 of SEQ ID NO: 2. The recombinant polypeptide may comprise an F1 domain (e.g. a truncated F1 domain lacking residues 1-16 of SEQ ID NO: 3) comprising one or more substitution(s) at positions 35, 45, 57, 58, 59, 64, 75, 83, 156, 164, 192, 378 and/or 379 of SEQ ID NO: 3.

Furthermore, some mutation(s) can compensate for a deficiency of cavity filling. Particularly, the cavity filling mutations can be selected from the list comprising the amino acid substitutions at positions 49, 67, 80, 137, 147, 159, 160, 161, 177 and 258 of the native hMPV F protein sequence of SEQ ID NO: 1. In one embodiment, the cavity filling mutations include a T49M substitution, an I67L substitution, an I137W substitution, an A147V substitution, an A159V substitution, a T160F substitution, an A161M substitution and/or an I177L substitution in SEQ ID NO: 1. Thus in some embodiments, the recombinant polypeptide may comprise an F2 domain comprising a T31M or I49L substitution in the sequence of SEQ ID NO: 2. In other embodiments, the recombinant polypeptide may comprise an (e.g. truncated) F1 domain comprising one or more substitutions in SEQ ID NO: 3 selected from I35W, A45V, A57V, T58F, A59M, I75L and/or F156I.

In another embodiment, the recombinant single-chain F protein may comprise one or more substitution(s) leading to formation of non-natural hydrogen bond(s) or salt bridge(s). For example, such substitutions include an E80N and S266D in SEQ ID NO: 1. Thus the recombinant polypeptide may comprise the F2 domain comprising a E62N substitution in the sequence of SEQ ID NO: 2. In other embodiments, the recombinant polypeptide may comprise an (e.g. truncated) F1 domain comprising the substitution S164D in SEQ ID NO: 3.

In some embodiments, the recombinant single-chain F protein may comprise further cysteine substitution(s) for creation an additional stabilizing disulfide bond(s). For example, substitutions E51C and K166C can form a non-natural disulfide bond between a cysteine residues at position 51 of the β-strand of the F2 domain and a cysteine at position 166 of the HRA α4 element of the native hMPV F protein sequence of SEQ ID NO: 1. This modification impairs a possible salt-bridge between E51 and K138 from a helix in HRA. Mutation S266D introduces a non-natural salt-bridge to K138 to compensate loss of attachment for this helix. Additionally, substitution of the vicinal residues I480 and L481 of SEQ ID NO: 1 for cysteine allows introduction of three disulfide bonds across three protomers to make the covalently linked trimer protein. Thus in one embodiment, the recombinant polypeptide may comprise an F2 domain comprising a E33C substitution in the sequence of SEQ ID NO: 2. In other embodiments, the recombinant polypeptide may comprise an (e.g. truncated) F1 domain comprising the substitution(s) K64C, S164D, I378C and/or L379C in SEQ ID NO: 3.

In another embodiment, the recombinant single-chain F protein may comprise a modification(s) helpful for expression of a soluble recombinant protein. For instance, a substitution of a glycine for a glutamic acid residue may be present at position 294 (G294E) of the native hMPV F protein sequence of SEQ ID NO: 1, which may lead to a higher yield of the protein expression. Thus in one embodiment, the recombinant polypeptide may comprise a (e.g. truncated) F1 domain comprising a substitution G192E in SEQ ID NO: 3.

In some embodiments, the recombinant single-chain F protein may comprise combinations of two, three, four, five, six, seven, eight, nine, ten or more amino acid substitutions and/or other modifications. In some embodiments, the recombinant single-chain F protein may comprise a trimerization helper, so called foldon domain, e.g. linked to the C-terminus of the recombinant F protein subunit, that allows formation of a protein trimer. The foldon domain may derive from fibritin of T4 bacteriophage. The recombinant hMPV F protein of the present invention may be produced as mono- or hetero-trimer.

In some embodiments, the recombinant hMPV F protein may comprise or consist of an amino acid sequence having at least 85%, 90%, 95%, 96%, 97%, 98% or 99% sequence identity to the amino acid sequence of any one of SEQ ID NOs: 5 to 9 or 24 to 28. The recombinant single-chain F protein may comprise an F2 domain comprising or consisting of an amino acid sequence having at least 85%, 90%, 95%, 96%, 97%, 98% or 99% sequence identity to the amino acid sequence of SEQ ID NO: 2. The recombinant single-chain F protein may comprise an F1 domain comprising or consisting of an amino acid sequence having at least 85%, 90%, 95%, 96%, 97%, 98% or 99% sequence identity to the amino acid sequence of SEQ ID NO: 3. In some embodiments, the recombinant single-chain F protein may comprise a truncated F1 domain comprising or consisting of an amino acid sequence having at least 85%, 90%, 95%, 96%, 97%, 98% or 99% sequence identity to residues 17-437 or 17-388 of the amino acid sequence of SEQ ID NO: 3.

The recombinant hMPV proteins of the present invention are immunogenic and can induce neutralizing antibodies recognizing the native hMPV F protein. The present disclosure also includes immunogenic fragments of the recombinant hMPV proteins and the immunogenic proteins having at least 85%, 90%, 95%, 96%, 97%, 98% or 99% sequence identity to the sequence of anyone of SEQ ID NOs: 5 to 9 or 24 to 28.

The present disclosure also provides isolated nucleic acid molecules encoding the modified hMPV F-proteins, vectors comprising the isolated nucleic acid molecules, host cells for recombinant expression of the modified hMPV F proteins.

The present disclosure also provides immunogenic compositions or vaccines comprising the recombinant hMPV F proteins, or isolated DNA molecules encoding the hMPV F protein or vectors of the invention, further comprising a pharmaceutically acceptable carrier and/or excipient, used with or without an adjuvant. Particularly, the disclosure provides immunogenic compositions or vaccines for stimulating an immune response in a subject, particularly an immune response, which can neutralize hMPV viruses and protect against hMPV infections. The disclosure further provides immunogenic compositions or vaccines comprising additional antigens derived from hMPV, RSV or PIV3 (parainfluenza virus type 3). The immunogenic proteins, isolated DNA molecules, vectors and immunogenic compositions or vaccines disclosed herein are suitable for use as a medicament, particularly for the prophylactic and/or therapeutic treatment of viral respiratory tract infections and associated diseases, especially infections and disease caused by hMPV.

Methods of production the recombinant hMPV F proteins, or isolated DNA molecules encoding the hMPV F protein or immunogenic compositions (vaccines) are encompassed in the present disclosure.

Methods of generating an immune response in a subject, and methods of treating, inhibiting or preventing hMPV infections are also included.

In a further aspect, the present invention provides an immunogenic human metapneumovirus (hMPV) modified F protein or fragment thereof, stabilized in a pre-fusion conformation by one or more amino acid substitutions relative to a native hMPV F protein sequence; wherein the modified F protein or fragment thereof comprises a glutamine residue substituted for an asparagine residue at a position corresponding to position 97 of the native hMPV F protein sequence of SEQ ID NO: 1 (N97Q).

In a further aspect, the present invention provides an immunogenic human metapneumovirus (hMPV) modified F protein or fragment thereof, stabilized in a pre-fusion conformation by one or more amino acid substitutions relative to a native hMPV F protein sequence; wherein the modified F protein or fragment thereof comprises a glycine residue substituted for a glutamic acid residue at a position corresponding to position 294 of the native hMPV F protein sequence of SEQ ID NO: 1 (G294E).

In a further aspect, the present invention provides an immunogenic human metapneumovirus (hMPV) modified F protein or fragment thereof, stabilized in a pre-fusion conformation by one or more amino acid substitutions relative to a native hMPV F protein sequence; wherein the modified F protein or fragment thereof comprises one or more substitution(s) at positions corresponding to positions 49, 51, 67, 80, 137, 147, 159, 160, 161, 166, 177, 258, 266, 480 and/or 481 of the native hMPV F protein sequence of SEQ ID NO: 1.

In a further aspect, the present invention provides an immunogenic human metapneumovirus (hMPV) modified F protein or fragment thereof, stabilized in a pre-fusion conformation by two or more amino acid substitutions relative to a native hMPV F protein sequence; wherein the modified F protein or fragment thereof comprises the substitutions E51C and K166C relative to the native hMPV F protein sequence of SEQ ID NO: 1, and wherein the substituted cysteine residues form a non-native disulfide bond.

In a further aspect, the present invention provides an immunogenic human metapneumovirus (hMPV) modified F protein or fragment thereof, stabilized in a pre-fusion conformation by one or more amino acid substitutions relative to a native hMPV F protein sequence; wherein the modified F protein or fragment thereof comprises one or more substitutions selected from the group consisting of T49M, E80N, I137W, A147V, A159V, T160F, A161M, 167L, I177L, F258I, S266D, I480C and/or L481C relative to the native hMPV F protein sequence of SEQ ID NO: 1.

In a further aspect, the present invention provides an immunogenic human metapneumovirus (hMPV) modified F protein or fragment thereof, stabilized in a pre-fusion conformation by three or more amino acid substitutions relative to a native hMPV F protein sequence; wherein the modified F protein or fragment thereof comprises at least the substitutions T49M, A161M and I67L or I177L relative to the native hMPV F protein sequence of SEQ ID NO: 1.

In a further aspect, the present invention provides an immunogenic human metapneumovirus (hMPV) modified F protein or fragment thereof, stabilized in a pre-fusion conformation by three or more amino acid substitutions relative to a native hMPV F protein sequence; wherein the modified F protein or fragment thereof comprises one of the following substitution combinations relative to the native hMPV F protein sequence of SEQ ID NO: 1:

N97Q, R102G and G294E;

N97Q, R102G, T160F, I177L and G294E;

N97Q, R102G, T49M, I67L, A161M, E80N, F258I and G294E;

N97Q, R102G, T49M, I67L, A161M, E51C, K166C, S266D, G294E, I480C and L481C; or

N97Q, R102G, T49M, A161M, I137W, A159V, A147V, I177L and G294E.

Unless otherwise specified herein, all amino acid positions mentioned in the present specification correspond to the amino acid positions of the native hMPV F protein sequence of SEQ ID NO: 1. The corresponding positions of such mutations in the F2 domain of SEQ ID NO: 2 and the F1 domain of SEQ ID NO: 3 can be derived directly therefrom. The F2 domain of SEQ ID NO: 2 corresponds to residues 19 to 102 of SEQ ID NO: 1. The F1 domain of SEQ ID NO: 3 corresponds to residues 103 to 539 of SEQ ID NO: 1.

DETAILED DESCRIPTION OF THE INVENTION

Definitions

Adjuvant

Figure 1:
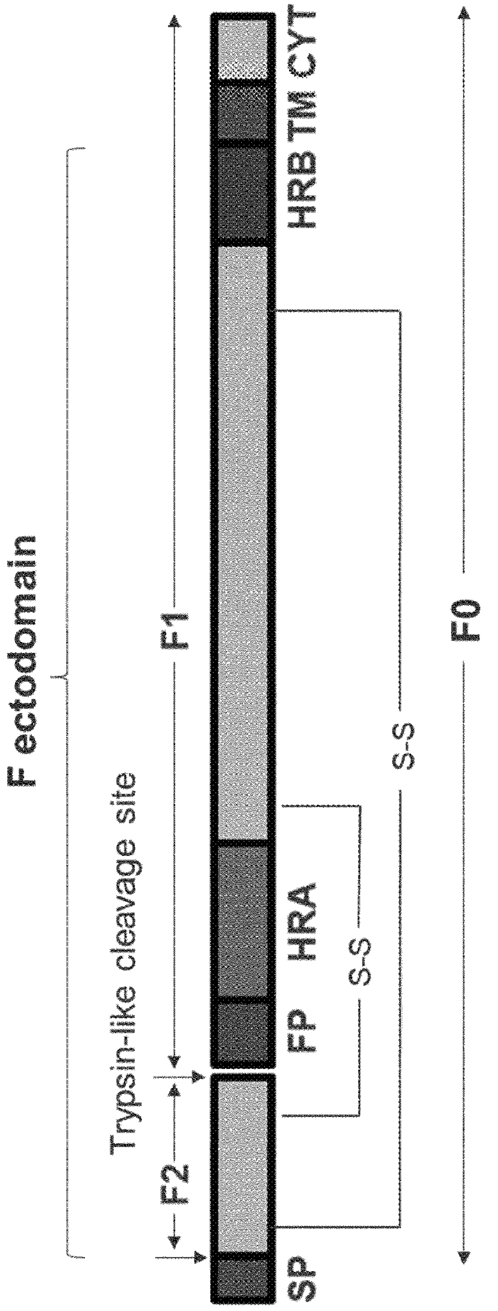
FIG. 1 shows the schematic diagram of the native hMPV F protein with the indicated domains and important motifs. F0: protein precursor; F1, F2: F1 and F2 domains; SP: signal peptide; FP: fusion peptide; HRA, HRB: Heptad Repeat domain A and B, TM: transmembrane domain; CYT: cytoplasmic tail; S—S: disulfide bond.

By "adjuvant" is meant any substance that is used to specifically or non-specifically potentiate an antigen-specific immune response, perhaps through activation of antigen presenting cells. Examples of adjuvants include an oil emulsion (e.g., complete or incomplete Freund's adjuvant), montanide Incomplete Seppic Adjuvant such as ISA51, a squalene-based oil-in-water emulsion adjuvants such as MF59® (Novartis AG) (Ott G. et al. 1995. *Pharm Biotechnol* 6: 277-96) or AddaVax™ (InvivoGen), monophosphoryl lipid A (MPL) (Cluff C W. 2010. *Adv Exp Med Biol* 667:111-23), aluminum salt adjuvant (alum) (as described in WO 2013/083726), polycationic polymer, especially polycationic peptide, especially polyarginine or a peptide containing at least two LysLeuLys motifs, especially KLKLLLLLKLK (SEQ ID NO: 55), immunostimulatory oligodeoxynucleotide (ODN) containing non-methylated cytosine-guanine dinucleotides (CpG), e.g. CpG 1018 (Dynavax), in a defined base context (e.g., as described in WO 96/02555) or ODNs based on inosine and cytidine (e.g., as described in WO 01/93903), or deoxynucleic acid containing deoxy-inosine and/or deoxyuridine residues (as described in WO 01/93905 and WO 02/095027), especially $oligo(dIdC)_{13}$ (SEQ ID NO: 56) based adjuvant IC31® (Valneva SE) (as described in WO 04/084938 and Olafsdottir et al. 2009. *Scand J Immunol.* 69(3): 194-202), neuroactive compound, especially human growth hormone (described in WO 01/24822), a chemokine (e.g., defensins 1 or 2, RANTES, MIP1-α, MIP-2, interleukin-8, or a cytokine (e.g., interleukin-1β, -2, -6, -10 or -12; interferon-γ; tumor necrosis factor-α; or granulocyte-monocyte-colony stimulating factor), muramyl dipeptide (MDP) variants, non-toxic variants of bacterial toxins, QS-21 (Antigenics Inc.), Quill A, N-acetylmuramyl-L-alanyl-D-isoglutamyl-L-alanine-2-[1,2-dipalmitoyl-s-glycero-3-(hydroxyphosphoryloxy)]ethylamide (MTP-PE) and others as described in Sarkar et al. 2019. *Expert Rev Vaccine:* 18(5): 505-521, as well as compositions e.g. adjuvant systems, such as AF03, AS01, AS03 and AS04 (Giudice et al. 2018. *Seminars in Immunology* 39: 14-21). Adjuvants that transduce immunological signals via TLR3, TLR4, TLR7, TLR8, and TLR9 receptors promotes Th1-biased immunity, while signaling via TLR2/TLR1, TLR2/TLR6 and TLR5 promotes Th2-biased immunity. For instance, such adjuvants as CpG ODN, polyIC and MPL predominantly induce Th1 responses, alum is strong inducer of Th2 response, while MF59®, Addavax™, and IC31® may induce mixed Th1 and Th2 responses. An adjuvant may be administered with an antigen or may be administered by itself, either by the same route as that of the antigen or by a different route than that of the antigen. A single adjuvant molecule may have both adjuvant and antigen properties.

Amino Acid Substitutions

Amino acid substitution refers to the replacement of one amino acid in a polypeptide with a different amino acid or with no amino acid (i.e., a deletion). As used herein, conservative substitutions are those substitutions that do not alter a basic structure and function of a protein, e.g. as the ability of the protein to induce an immune response when administered to a subject.

The following six groups are considered conservative substitutions for one another:

1) alanine (A), serine (S), threonine (T);
2) aspartic acid (D), glutamic acid (E);
3) asparagine (N), glutamine (G);
4) arginine (R), lysine (K);
5) leucine (L), isoleucine (I), methionine (M), valine (V); and
6) phenylalanine (F), tyrosine (Y), tryptophan (W).

Non-conservative substitutions are those that reduce an activity of function of the modified hMPV protein, such that the ability to induce an immune response when administered to a subject.

Antibody

An antibody is polypeptide or protein that specifically binds and recognizes an antigen such as the hMPV F protein or an antigenic fragment of MPV F protein. The term "antibody" is used herein in the broadest sense and encompasses various antibody structures, including but not limited to monoclonal antibodies, polyclonal antibodies, multispecific antibodies (e.g., bispecific antibodies), and antibody fragments, so long as they exhibit the desired antigen-binding activity. Non-limiting examples of antibodies include, for example, intact immunoglobulins and variants and fragments thereof known in the art that retain binding affinity for the antigen. Examples of antibody fragments include but are not limited to Fv, Fab, Fab', Fab'-SH, F(ab')2; diabodies; linear antibodies; single-chain antibody molecules (e.g. scFv); and multispecific antibodies formed from antibody fragments. Antibody fragments include antigen-binding fragments either produced by the modification of whole antibodies or those synthesized de novo using recombinant DNA methodologies (see, e.g., Kontermann and Dubel (Ed), Antibody Engineering, Vols. 1-2, 2$^{nd}$ Ed., Springer Press, 2010).

The following antibodies are have been used in the present invention: the MPE8 antibody is a monoclonal antibody that specifically binds to an epitope that is present on the surface of the hMPV F protein in the pre-fusion but not post-fusion conformation is (see Corti et al. 2013. Nature, 501:439-443). Sequences of the heavy and light variable regions of the MPE8 antibody are deposited in the GenBank with the accession Nos. AGU13651.1 and AGU13652.1, respectively. The MF1 antibody recognizes the 6HB domain of the post-fusion hMPV F protein as described in Rodriguez, 2015 (*J Virol Methods* 224: 1-8). The DS7 antibody described in Williams et al., 2007 (*J Virology* 81(15): 8315-24) binds to both the pre- and post-fusion hMPV F protein conformations.

Cavity-Filling Mutation (or Substitution)

A cavity-filling mutation is an amino acid substitution that fills a cavity within the protein core of the hMPV F protein. Cavities are essentially voids within a folded protein where amino acids or amino acid side chains are not present. In several embodiments, a cavity filling amino acid substitution is introduced to fill a cavity in the hMPV F protein ectodomain core present in the pre-fusion conformation.

Foldon Domain

A foldon domain is an amino acid sequence that naturally forms a trimeric structure and may also be referred to as a trimerization helper domain. In some examples, a foldon domain can be included in the amino acid sequence of a disclosed recombinant protein so that the antigen will form a trimer. In one example, a foldon domain is the T4 bacteriophage-derived foldon domain including the amino acid sequence set forth as e.g. GYIPEAPRDGQAY-VRKDGEWVLLSTF (SEQ ID NO:10). The foldon domain may, for example, be cleaved from a purified protein, for example by incorporation of a thrombin cleavage site adjacent to the foldon domain.

Glycosylation Site

A glycosylation site is an amino acid sequence on the surface of a polypeptide, such as a protein, which accommodates the attachment of a glycan. An N-linked glycosylation site is triplet sequence of NX(S/T) in which N is asparagine, X is any residues except proline, and (S/T) is a serine or threonine residue. A glycan is a polysaccharide or oligosaccharide. Glycan may also be used to refer to the carbohydrate portion of a glycoconjugate, such as a glycoprotein, glycolipid, or a proteoglycan.

Heterologous

The term "heterologous" means originating from a different genetic source. An amino acid sequence that is heterologous to a protein or virus originated from a source other than the protein or virus in which it is present or expressed. In one specific, non-limiting example, a heterologous peptide linker present in a recombinant polypeptide between two domains refers to a peptide sequence that is not naturally present in the wild type polypeptide between those two domains, e.g. the peptide linker is an artificial sequence linking the two domains in the recombinant polypeptide.

Homologous

Homologous proteins have a similar structure and function, for example, proteins from two or more species or viral strains that have similar structure and function in the two or more species or viral strains. Homologous proteins share similar protein folding characteristics and can be considered structural homologs. Homologous proteins typically share a high degree of sequence conservation, such as at least 80%, at least 90%, at least 91%, at least 92%, at least 93%, at least 94%, or at least 95%, at least 96%, at least 97%, at least 98%, or at least 99% sequence conservation, and a high degree of sequence identity, such as at least 80%, at least 90%, at least 91%, at least 92%, at least 93%, at least 94%, or at least 95%, at least 96%, at least 97%, at least 98%, or at least 99% sequence identity.

hMPV F Protein

An hMPV F (fusion) protein is an envelope glycoprotein that facilitates fusion of viral and cellular membranes. In nature, the hMPV F protein is synthesized as a single polypeptide precursor approximately 540 amino acids long, which includes the N-terminal signal peptide (approximately the first 18 residues) that directs localization to the endoplasmic reticulum where the signal peptide is cleaved off. The remaining polypeptide, designated F0, constitutes the F protein monomer (protomer), which is processed at a protease cleavage site between positions 102 and 103 in the native F protein sequence of SEQ ID NO: 1 generating two disulfide-linked fragments, F1 and F2. The F2 fragment originates from the N-terminal portion of the F precursor and includes approximately residues 19-102 of SEQ ID NO: 1. The larger of these fragments, F1, includes the C-terminal portion of the F precursor (approximately residues 103-539 of SEQ ID NO: 1) including an extracellular/lumenal region (residues 103-490), a transmembrane domain (residues 491-513), and a cytoplasmic domain (residues 514-539) at the C-terminus. The extracellular portion of the hMPV F protein is the F ectodomain, which includes the F2 domain (approximately the hMPV F protein positions 19-102) and the F1 ectodomain (approximately the hMPV F protein positions 103-490). Three F2-F1 protomers oligomerize in the mature F protein trimer, which adopts a metastable pre-fusion conformation that is triggered to undergo a conformational change to a post-fusion conformation upon contact with a target cell membrane. This conformational change exposes a hydrophobic sequence, known as the fusion peptide (FP), located at the N-terminus of the F1 domain, which associates with the host cell membrane and promotes fusion of the membrane of the virus, or an infected cell, with the target cell membrane. Three hMPV F ectodomains may form a protein complex of three hMPV F protomers. The present invention relates to a modified hMPV F protein or fragment thereof, i.e. a recombinant polypeptide comprising one or more non-natural amino acid mutations with respect to a wild-type, native or naturally-occurring hMPV F protein sequence that stabilize the pre-fusion conformation.

hMPV F0 Polypeptide

The F0 polypeptide is a precursor of the hMPV F protein remained after cleavage of the signal peptide, which consists of the F2 domain and F1 domain including the F1 extracellular domain, transmembrane domain and cytosolic tail. The native F0 polypeptide is processed at a protease cleavage site separating F1 and F2 (approximately between positions 102 and 103 of SEQ ID NO: 1), resulting in the F1 and F2 polypeptide fragments (domains).

hMPV F1 Domain

The hMPV F1 domain is a part of the amino acid sequence of the hMPV F protein. As used herein, “F1 domain” refers to both native F1 sequences and F1 sequences including modifications (e.g. amino acid substitutions, insertions, or deletions). The native F1 domain (SEQ ID NO: 3) includes approximately residues 103-539 of the native hMPV F protein, and includes (from N- to C-terminus) an extracellular/lumenal region (residues 103-490 of SEQ ID NO: 1), a transmembrane domain (residues 491-513 of SEQ ID NO: 1), and a cytosolic domain (residues 514-539 of SEQ ID NO: 1) at the C-terminus. Several embodiments include an F1 domain modified from a native F1 sequence, for example an F1 domain that lacks a fusion peptide (e.g. residues 103-118 of SEQ ID NO: 1). In some embodiments, the F1 domain is an F1 ectodomain, i.e. lacks the transmembrane and cytosolic domain, for example the F1 domain corresponds to residues 103 to 490 or 119 to 490 of SEQ ID NO: 1. In further embodiments, the F1 domain includes one or more amino acid substitutions that stabilize a recombinant single-chain F protein (containing the F1 domain) in a pre-fusion conformation.

hMPV F2 Domain

The hMPV F2 domain is a part of the amino acid sequence of the hMPV F protein. As used herein, “F2 domain” refers to both native F2 polypeptides and F2 polypeptides including modifications (e.g. amino acid substitutions) from the native sequence, for example, modifications designed to stabilize a recombinant F protein (including the modified F2 polypeptide) in a hMPV F protein pre-fusion conformation. The native F2 domain (SEQ ID NO: 2) includes approximately residues 19-102 of SEQ ID NO: 1. In the native mature hMPV F protein, the F2 domain is linked to the F1 domain by two disulfide bonds.

hMPV Fusion Peptide (FP)

The hMPV fusion peptide is a part of the amino acid sequence of the hMPV F protein. The fusion peptide may be residues 103-118 of SEQ ID NO: 1, i.e. the N-terminal residues 1 to 16 of the F1 domain of SEQ ID NO: 3.

hMPV F Protein Pre-Fusion Conformation

The hMPV F protein pre-fusion conformation is a structural conformation adopted by the hMPV F protein prior to triggering of the fusogenic event that leads to transition of the hMPV F protein to the post-fusion conformation and following processing into a mature hMPV F protein in the secretory system. The three-dimensional structure of an exemplary hMPV F protein in a pre-fusion conformation is discussed herein and for example in WO 2016/103238. The pre-fusion conformation of hMPV F protein is similar in overall structure to the pre-fusion conformation of the F protein of other paramyxoviruses (such as RSV), though with some significant differences. In several embodiments, a recombinant hMPV F protein stabilized in the pre-fusion conformation specifically binds to an antibody (such as MPE8 antibody, see WO 2016/103238) specific for the trimeric form of the hMPV F protein in the pre-fusion, but not post-fusion, conformation.

Single-Chain hMPV F Protein

The single-chain hMPV F protein of the present invention is a recombinant hMPV F protein ectodomain (also used herein as a single-chain polypeptide) that is expressed as a single polypeptide chain including a (modified) hMPV F1 domain and a (modified) hMPV F2 domain. The single-chain hMPV F protein can typically trimerize to form a trimeric hMPV F protein subunit, preferentially being fused to a trimerization helper domain, e.g. foldon. In some embodiments, the recombinant single-chain hMPV F polypeptide does not include a protease cleavage site between the F1 domain and F2 domain and is not cleaved into separate F1 domain and F2 domain polypeptides when produced in cells. In one embodiment, F1 domain and F2 domain are linked with a heterologous peptide linker to generate the single-chain construct.

Immune Response

An immune response is a response of a cell of the immune system, such as a B cell, T cell, or monocyte, to a stimulus. In one embodiment, the response is specific for a particular antigen (an “antigen-specific response”). In one embodiment, an immune response is a T cell response, such as a CD4+ response or a CD8+ response. In another embodiment, the response is a B cell response, and results in the production of specific antibodies. “Priming an immune response” refers to pre-treatment of a subject with an adjuvant to increase the desired immune response to a later administered immunogenic agent. “Enhancing an immune response” refers to co-administration of an adjuvant and an immunogenic agent, wherein the adjuvant increases the desired immune response to the immunogenic agent compared to administration of the immunogenic agent to the subject in the absence of the adjuvant.

Immunogen

An immunogen is a compound, composition, or substance that can stimulate production of antibodies or a T cell response in an animal, including compositions that are injected or absorbed into an animal. An immunogen reacts with the products of specific humoral or cellular immunity, including those induced by heterologous antigens, such as the disclosed recombinant hMPV F proteins. An immunogen can include one or more epitopes. In some embodiments, an immunogen can be a recombinant hMPV F protein or immunogenic fragment thereof, a protein nanoparticle or virus-like particle including the recombinant hMPV F protein or immunogenic fragment thereof, or nucleic acid or vector encoding the recombinant hMPV F protein or immunogenic fragment thereof, that is capable of inducing an immune response in a mammal, such as a mammal infected or at risk of infection with a pathogen. Administration of an immunogen to a subject can lead to protective immunity and/or proactive immunity against a pathogen of interest.

Immunogenic Composition

An immunogenic composition is a composition comprising an immunogen that induces a measurable CTL response against an antigen, or induces a measurable B cell response (such as production of antibodies) against an antigen, included on the immunogen or encoded by a nucleic acid molecule included in the immunogen. In one example, an immunogenic composition is a composition that includes the disclosed recombinant hMPV F protein or immunogenic fragment thereof, which induces a measurable CTL response against the hMPV virus, or induces a measurable B cell response (such as production of antibodies) against the hMPV F protein when administered to a subject. An immunogenic composition can include isolated nucleic acids encoding an immunogenic protein that can be used to express the immunogenic protein and thus to elicit an immune response against this protein. Thus, in another example, an immunogenic composition is a composition that includes a nucleic acid molecule encoding the disclosed recombinant hMPV F protein or immunogenic fragment thereof, that induces a measurable CTL response against the hMPV virus, or induces a measurable B cell response (such as production of antibodies) against the hMPV F polypeptide when administered to a subject. For in vivo use, the immunogenic composition will typically include an immunogenic polypeptide or nucleic acid molecule encoding an immunogenic polypeptide in a pharmaceutically acceptable carrier and may also include other agents, such as an adjuvant. Any particular polypeptide, such as a disclosed recombinant hMPV F protein or a nucleic acid encoding the protein, can be readily tested for its ability to induce a CTL or B cell response by art-recognized assays.

Isolated

An "isolated" biological component has been substantially separated or purified away from other biological components, such as other biological components in which the component naturally occurs, such as other chromosomal and extrachromosomal DNA, RNA, and proteins. Proteins, peptides and nucleic acids that have been "isolated" include proteins purified by standard purification methods. The term also embraces proteins or peptides prepared by recombinant expression in a host cell as well as chemically synthesized proteins, peptides and nucleic acid molecules. Isolated does not require absolute purity, and can include protein, peptide, or nucleic acid molecules that are at least 50% isolated, such as at least 75%, 80%, 90%, 95%, 98%, 99%, or even 99.9% isolated. The modified hMPV F proteins disclosed herein that are stabilized in a pre-fusion conformation are isolated from hMPV F proteins in a post-fusion conformation, for example, are at least 80% isolated, at least 90%, 95%, 98%, 99%, or even 99.9% isolated from hMPV F proteins in a post-fusion conformation.

Linker

A linker is a bi-functional molecule that can be used to link two molecules into one contiguous molecule, for example, to link two domains in a single polypeptide. Preferably, the linker is a peptide linker. The linker may be of any suitable length, e.g. 1 to 20, 1 to 15, 1 to 10, 1 to 5 or less amino acid residues. The linker may comprise or consist of e.g. alanine, serine, glycine, cysteine and/or valine residues. Preferably, the linker may comprise at least one cysteine residue.

Native (or Natural) Protein, Sequence, or Disulfide Bond

A native or natural (herein used interchangeably) polypeptide, sequence, residue or disulfide bond is one that has not been modified, for example, by selective mutation to focus the antigenicity of the antigen to a target epitope, or to introduce a disulfide bond into a protein that does not occur in the native protein. Native or natural proteins, residues or sequences are also referred to as wild type proteins, residues or sequences. A non-native or non-natural disulfide bond is a disulfide bond that is not present in a native protein, for example a disulfide bond that forms in a protein due to introduction of one or more cysteine residues into the protein by genetic engineering. Likewise, a non-natural cysteine residue in a domain is a cysteine residue that is not present at that position in a wild type, native or natural sequence.

Neutralizing Antibody

A neutralizing antibody reduces the infectious titer of an infectious agent by binding to a specific antigen on the infectious agent. In some examples, the infectious agent is a virus. In some examples, an antibody that is specific for hMPV F protein neutralizes the infectious titer of hMPV. In some embodiments, the neutralizing antibody binds to and inhibits the function of related antigens, such as antigens that share at least 85%, 90%, 95%, 96%, 97%, 98% or 99% identity antigenic surface of antigen. With regard to an antigen from a pathogen, such as a virus, the antibody can bind to and inhibit the function of an antigen from more than one class and/or subclass of the pathogen. For example, with regard to hMPV, the antibody can bind to and inhibit the function of an antigen, such as hMPV F protein from more than one group. In one embodiment, broadly neutralizing antibodies to hMPV are distinct from other antibodies to hMPV in that they neutralize a high percentage of the many types of hMPV in circulation.

Pharmaceutically Acceptable Carrier

Pharmaceutically acceptable carriers are used to formulate the immunogenic hMPV F protein for clinical administration. Remington's Pharmaceutical Sciences, by E. W. Martin, Mack Publishing Co., Easton, PA, 19th Edition, 1995, describes compositions and formulations suitable for pharmaceutical delivery of the disclosed immunogens. In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate. In particular embodiments, suitable for administration to a subject the carrier may be sterile, and/or suspended or otherwise contained in a unit dosage form containing one or more measured doses of the composition suitable to induce the desired anti-MPV immune response. It may also be accompanied by medications for its use for treatment purposes. The unit dosage form may be, for example, in a sealed vial that contains sterile contents or a syringe for injection into a subject, or lyophilized for subsequent solubilization and administration or in a solid or controlled release dosage.

Polypeptide

A polypeptide is any chain of amino acids, regardless of length or post-translational modification (e.g., glycosylation or phosphorylation). "Polypeptide" applies to amino acid polymers including naturally occurring amino acid polymers and non-naturally occurring amino acid polymer as well as in which one or more amino acid residue is a non-natural amino acid, for example an artificial chemical mimetic of a corresponding naturally occurring amino acid. A "residue" refers to an amino acid or amino acid mimetic incorporated in a polypeptide by an amide bond or amide bond mimetic. A polypeptide has an amino terminal (N-terminal) end and a carboxy terminal (C-terminal) end. "Polypeptide" is used interchangeably with peptide or protein, and is used herein to refer to a polymer of amino acid residues. In many instances, one or more polypeptides can fold into a specific three-dimensional structure including surface-exposed amino acid residues and non-surface-exposed amino acid residues. In some instances, a protein can include multiple polypeptides that fold together into a functional unit. For example, the mature hMPV F protein on the cell surface includes three F2/F1 heterodimers that trimerize in to a multimeric protein. "Surface-exposed amino acid residues" are those amino acids that have some degree of exposure on the surface of the protein, for example such that they can contact the solvent when the protein is in solution. In contrast, non-surface-exposed amino acids are those amino acid residues that are not exposed on the surface of the protein, such that they do not contact solution when the protein is in solution. In some examples, the non-surface-exposed amino acid residues are part of the protein core.

Recombinant Polypeptide or Protein

A recombinant polypeptide (or protein) is one that has a sequence that is not naturally occurring or has a sequence that is made by an artificial combination of two otherwise separated segments of sequence. This artificial combination can be accomplished by chemical synthesis or, more commonly, by the artificial manipulation of isolated segments of amino acid residues, for example, by genetic engineering techniques. In several embodiments, a recombinant single-chain polypeptide is encoded by a heterologous (for example, recombinant) nucleic acid that has been introduced into a host cell, such as a bacterial or eukaryotic cell. The nucleic acid can be introduced, for example, on an expression vector having signals capable of expressing the protein encoded by the introduced nucleic acid or the nucleic acid can be integrated into the host cell chromosome.

Sequence identity Sequence identity is frequently measured in terms of percentage identity: the higher the percentage, the more identical the two sequences are. Homologs, orthologs, or variants of a polypeptide will possess a relatively high degree of sequence identity when aligned using standard methods.

Methods of alignment of sequences for comparison are well known in the art. Various programs and alignment algorithms are described in: Smith & Waterman (Adv. Appl. Math. 2:482, 1981); Needleman & Wunsch (Mol. Biol. 48:443, 1970); Pearson & Lipman (Proc. Natl. Acad. Sci. USA 85:2444, 1988); Higgins & Sharp (Gene, 73:237-44, 1988); Higgins & Sharp (CABIOS 5:151-3, 1989); Corpet et al. (Nuc. Acids Res. 16:10881-90, 1988); Huang et al. (Computer Appls in the Biosciences 8:155-65, 1992); Pearson et al. (Meth. Mol. Bio. 24:307-31, 1994) and Altschul et al. (J. Mol. Biol. 215:403-10, 1990), presents a detailed consideration of sequence alignment methods and homology calculations. Once aligned, the number of matches is determined by counting the number of positions where an identical nucleotide or amino acid residue is present in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. Preferably, the percentage sequence identity is determined over the full length of the sequence. For example, a peptide sequence that has 1166 matches when aligned with a test sequence having 1554 amino acids is 75.0 percent identical to the test sequence ($1166 \div 1554 * 100 = 75.0$). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer.

The NCBI Basic Local Alignment Search Tool (BLAST) (Altschul et al. 1990. *Mol. Biol.* 215:403) is available from several sources, including the National Center for Biotechnology Information (NCBI, Bethesda, MD) and on the internet, for use in connection with the sequence analysis programs BLASTP, BLASTN, BLASTX, TBLASTN and TBLASTX. A description of how to determine sequence identity using this program is available on the NCBI website on the internet. The BLAST and the BLAST 2.0 algorithm are also described in Altschul et al. (*Nucleic Acids Res.* 25: 3389-3402, 1977). Software for performing BLAST analyses is publicly available through the National Center for Biotechnology Information (ncbi.nlm.nih.gov). The BLASTN program (for nucleotide sequences) uses as defaults a word length (W) of 11, alignments (B) of 50, expectation (E) of 10, M=5, N=−4, and a comparison of both strands. The BLASTP program (for amino acid sequences) uses as defaults a word length (W) of 3, and expectation (E) of 10, and the BLOSUM62 scoring matrix (see Henikoff & Henikoff. 1992. *Proc. Natl. Acad. Sci. USA* 89:10915-10919).

Homologs and variants of a polypeptide are typically characterized by possession of at least about 75%, for example at least about 80%, 85%, 90%, 91%, 92%, 93%, 94%, 95%, 96%, 97%, 98% or 99% sequence identity counted over at least 50, 100, 150, 250, 500 amino acid residues of the reference sequence, over the full length of the reference sequence or over the full length alignment with the reference amino acid sequence of interest. Proteins with even greater similarity to the reference sequences will show increasing percentage identities when assessed by this method, such as at least 80%, at least 85%, at least 90%, at least 95%, at least 98%, or at least 99% sequence identity. For sequence comparison of nucleic acid sequences, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters are used.

One example of a useful algorithm is PILEUP. PILEUP uses a simplification of the progressive alignment method of Feng & Doolittle (*Mol. Evol.* 35: 351-360, 1987). The method used is similar to the method described by Higgins & Sharp (*CABIOS* 5:151-153, 1989). Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al. 1984. *Nuc. Acids Res.* 12: 387-395).

As used herein, reference to "at least 80% identity" refers to "at least 80%, at least 85%, at least 90%, at least 91%, at least 92%, at least 93%, at least 94%, at least 95%, at least 96%, at least 97%, at least 98%, at least 99%, or even 100% identity" to a specified reference sequence, e.g. to at least 50, 100, 150, 250, 500 amino acid residues of the reference sequence or to the full length of the sequence. As used herein, reference to "at least 90% identity" refers to "at least 90%, at least 91%, at least 92%, at least 93%, at least 94%, at least 95%, at least 96%, at least 97%, at least 98%, at least 99%, or even 100% identity" to a specified reference sequence, e.g. to at least 50, 100, 150, 250, 500 amino acid residues of the reference sequence or to the full length of the sequence.

Therapeutically Effective Amount

A therapeutically effective amount is the amount of agent, such as a disclosed immunogen or immunogenic composition, that is sufficient to prevent, treat (including prophylaxis), reduce and/or ameliorate symptoms and/or underlying causes of a disorder or disease, for example to prevent, inhibit and/or treat hMPV infection. In some embodiments, a therapeutically effective amount is sufficient to reduce or eliminate a symptom of a disease, such as hMPV infection. For instance, this can be the amount necessary to inhibit or prevent viral replication or to measurably alter outward symptoms of the viral infection. In general, this amount will be sufficient to measurably inhibit virus replication or infectivity. In one example, a desired response is to inhibit, reduce or prevent hMPV infection. The infection does not need to be completely eliminated, reduced or prevented for the method to be effective. For example, administration of a therapeutically effective amount of the agent can decrease the infection (as measured by infection of cells, or by number or percentage of infected subjects) by a desired amount, for example by at least 10%, at least 20%, at least 50%, at least 60%, at least 70%, at least 80%, at least 90%, at least 95%, at least 98%, or even at least 100% (elimination or prevention of detectable hMPV infection) as compared to a suitable control.

It is understood that to obtain a protective immune response against a pathogen can require multiple administrations of the immunogenic composition. Thus, a therapeutically effective amount encompasses a fractional dose that contributes in combination with previous or subsequent administrations to attaining a protective immune response. For example, a therapeutically effective amount of an agent can be administered in a single dose, or in several doses, for example daily, during a course of treatment (such as a prime-boost vaccination treatment). However, the therapeutically effective amount can depend on the subject being treated, the severity and type of the condition being treated, and the manner of administration. A unit dosage form of the agent can be packaged in a therapeutic amount, or in multiples of the therapeutic amount, for example, in a vial (e.g., with a pierceable lid) or syringe having sterile components.

Vaccine

A vaccine is a pharmaceutical composition that elicits a prophylactic or therapeutic immune response in a subject. In some cases, the immune response is a protective immune response. Typically, a vaccine elicits an antigen-specific immune response to an antigen of a pathogen, for example a viral pathogen, or to a cellular constituent correlated with a pathological condition. A vaccine may include a polynucleotide (such as a nucleic acid encoding a disclosed antigen), a peptide or polypeptide (such as a disclosed antigen), a virus, a cell or one or more cellular constituents. In one specific, non-limiting example, a vaccine reduces the severity of the symptoms associated with hMPV infection and/or decreases the viral load compared to a control. In another non-limiting example, a vaccine reduces hMPV infection compared to a control.

Homology Modelling

In one aspect, this disclosure provides a novel modified hMPV F protein stabilized in a pre-fusion conformation. The present disclosure also provides a method for generating stabilized pre-fusion F proteins based on crystal structures and homology modelling. For the analysis of structural basis of stabilizing modification(s), a series of structures of available fusion proteins of hMPV and homologous fusion proteins were used. Among them, the crystal structure models of the pre-fusion hMPV F protein ectodomain (PDB:5WB0) and the post-fusion hMPV F protein ectodomain (PDB: 5L1X), the crystal structure models of the pre-fusion RSV F protein ectodomain (PDB:4DAB) and the post-fusion RSV F protein ectodomain (PDB:3RRR). The so-called trimerization helper domain by using foldon domain was modeled into the homology model based on structural data in PDB: 2IBL, 1OX3 and 1AVY.

Figure 2:
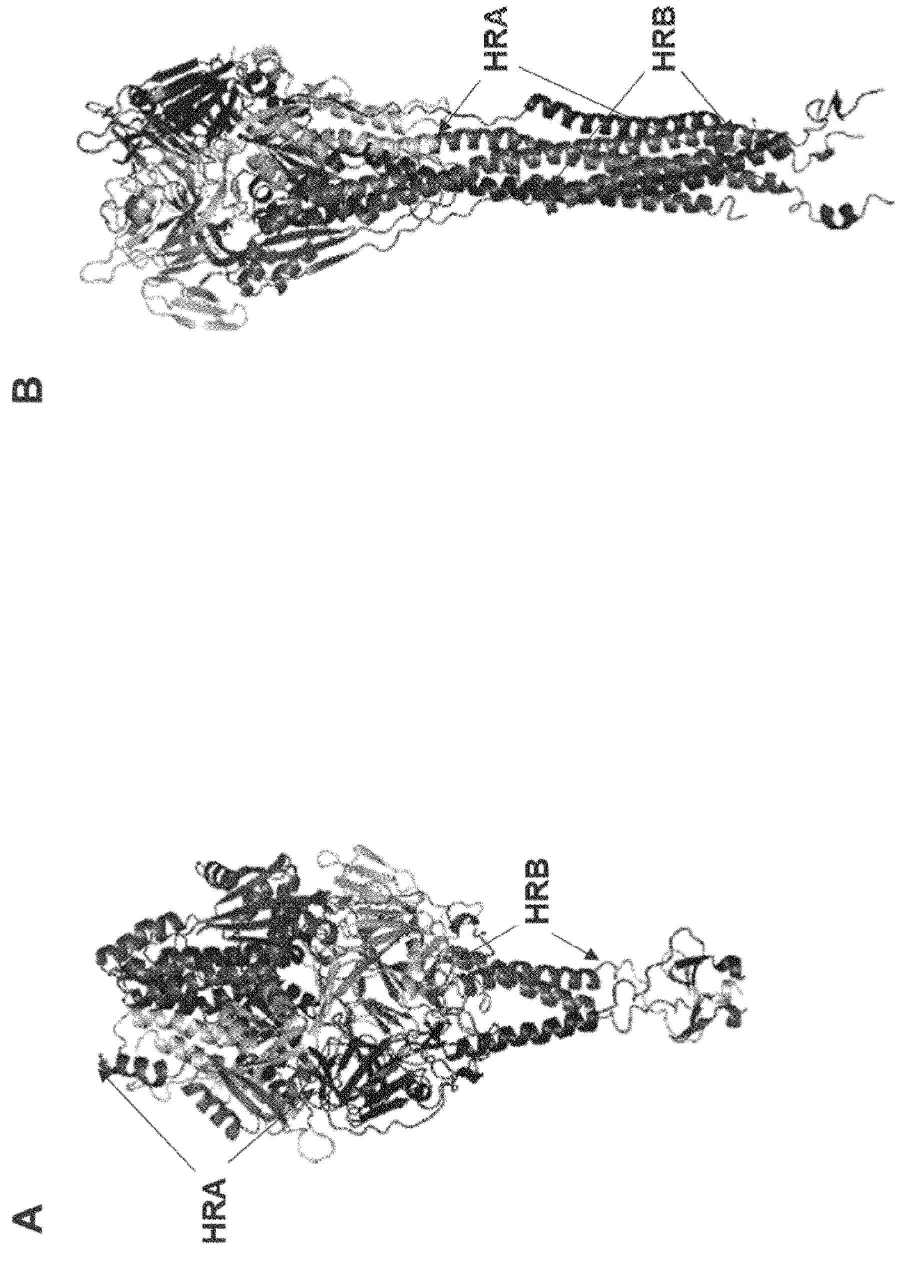
FIG. 2 shows structural changes in the pre-fusion and post-fusion conformations of the native hMPV F protein. (A) Ribbon diagram of the pre-fusion F protein trimer in which the C-termini of HRB are trimerized with a foldon domain and HRA is folded onto the head domain. (B) Ribbon diagram of the post-fusion F protein trimer, wherein HRA forms a long parallel three-helix-bundle, which together with the displaced HRB helices forms a stable six-helix-bundle.

The native mature hMPV F protein is composed of two polypeptides F2 and F1 covalently linked by two disulfide bonds. The maturation process includes one cleavage of the F0 precursor by a trypsin-like protease resulted in generating the free N-terminus of the F1 domain the fusion peptide FP, which interacts with the target cellular membrane and triggers the conformational changes. After the cleavage the relocation of the C-terminal part of F1 into the hydrophobic region of the inner trimeric cavity occurs. This may enhance the stability of the metastable pre-fusion state until a trigger event initiates refolding into the post-fusion conformer (see FIG. 2). In the pre-fusion conformation the HRA-containing region is bent and bound to the head domain, whereas in the post-fusion conformation it is a part of a long protruding helix. The pre-fusion-to-post-fusion transition includes refolding of heptad repeat A (HRA) sequences of the F1 subunit into one long α-helix, and insertion of the fusion peptide (FP), located at the N-terminus of HRA at its tip, into the cell membrane. This refolding promotes assembly of HRA and HRB sequences into a stable six-helix-bundle that drives the membrane fusion.

Single-Chain F Protein

Figure 3:
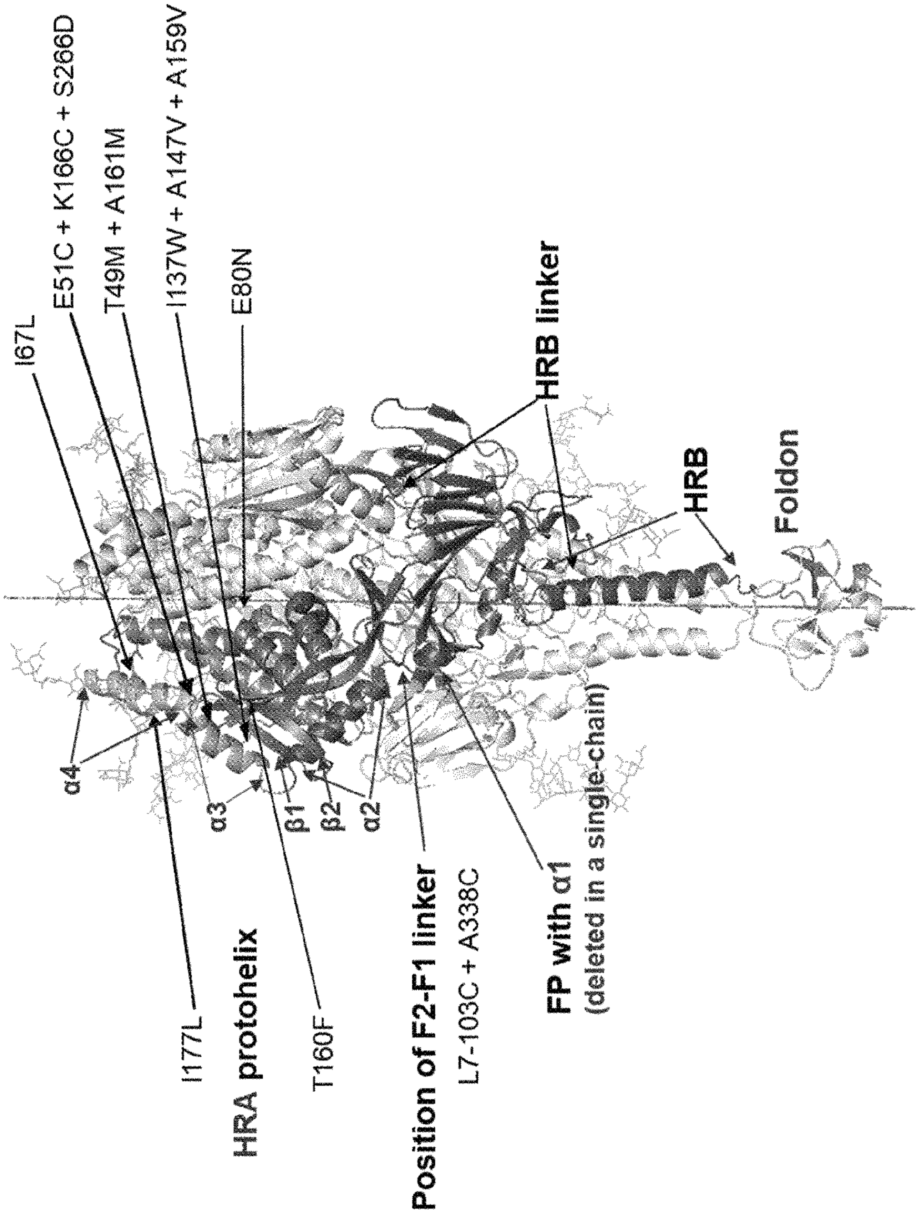
FIG. 3 shows three-dimensional structure (ribbon diagram) of the modified pre-fusion hMPV F protein with indicated mutations.

The modelling of a single-chain F protein was performed aiming to obtain a stabilized pre-fusion conformation and simultaneously keep a maximum structural similarity to the native hMPV F protein (see FIG. 3). It was assumed that deletion of the cleavage site between F1 and F2 would stabilize the pre-fusion conformer. Also elimination of one cleavage step is advantageous for the production process of the recombinant protein. The trypsin-like recognizing motif RQSR spans positions 99 to 102 of the native hMPV F protein sequence of SEQ ID NO: 1, and the cleavage occurs immediately after the second arginine at position 102 (R102). Cleavage elimination can be achieved by at least one mutation in the cleavage site, preferably by a substitution of the arginine at position 102. Particularly, R102 can be substituted for a glycine or another suitable amino acid residue. Especially, in one embodiment of the present invention, the trypsin-cleavage site is eliminated by substitution of the arginine at position 102 for a glycine (R102G).

For achieving a 3D structure similarity of the single-chain F ectodomain to the native pre-fusion hMPV F protein, a loop between the F1 domain and F2 domain was designed. In one embodiment, the loop is constructed by insertion of a heterologous peptide linker. In preferred embodiments, the size and the composition of the linker is optimized for the stability, antibody binding qualities and yield of the antigen. In one embodiment, length of the linker can be between 2 and 10 amino acid residues, preferably between 2 and 5 residues, more preferably between 3 and 5 residues, even more preferably 4 or 5 residues, the most preferably 5 residues. In another embodiment, the linker may be inserted between the amino acid residue at positions 95 to 102, preferably at positions 102, most preferably to the glycine residue at position 102 of SEQ ID NO: 1.

In some embodiments, the linker may be composed of one or more cysteine, glycine, alanine, phenylalanine, valine and/or serine residue(s). The liker may comprise one, two or three alanine residue(s), one or two valine residue(s) and one or two glycine residue(s). For instance, an alanine can be at position 1, 2, 3, 4, and/or 5 of the linker; a glycine can be at position 2, 3 and/or 4 of the linker; and a valine preferably can be at position 3 and/or 5 of the linker. Some non-limiting examples of the linker together with additional modifications of F2 and F1 are provided in Table 1.

In a preferred embodiment, the linker comprises at least one (e.g. one) cysteine residue. The cysteine may be at any position of the linker, preferably at position 1 or 3, that corresponds to position 103 and 105 of SEQ ID NO: 1. More preferably, the cysteine is at position 1 of the linker (i.e. at the N-terminal of the linker, preferably adjacent to the F2 domain) that corresponds to position 103 of the native hMPV F protein sequence of SEQ ID NO: 1. Even more preferably, the linker is CGAGA, CGAGV, CGAAV, AGCGA, CAAAV, CAAFV or CGAGA. In the most preferred embodiment, the linker is CGAGA (SEQ ID NO: 4).

TABLE 1a

Examples of variations of the single-chain linker joining F2 and F1 domains. The indel operation causes the deletion of the fusion peptide and has the effect of a net shortening of the ectodomain sequence. Cysteines marked with matching numbers, such as C(1) or C(2), form disulfide bonds between F1 and F2 domains. Cysteines marked with a prime ('C) are located on the neighboring protomer.

| Construct name | Sequence replacing residues 95-121 of SEQ ID NO: 1 | Additional substitution in SEQ ID NO: 1 |
|---|---|---|
| L7-type single-chain linker-net deletion of 11 aa residues vs F0 ectodomain Intraprotomerical disulfide bond | | |
| SEQ L7-2 | 95-IEQPRQSG C(1)GAGA TAG-121 | A338C(1) |
| SEQ L7-1 | 95-IENPRQSG C(1)GAGA TAG-121 | A338C(1) |
| SEQ L7-16 | 95-IEQPRQSG C(1)GAGV TAG-121 | A338C(1) |
| SEQ L7-17 | 95-IENPRQSG C(1)GAGV TAG-121 | A338C(1) |
| SEQ L7-5 | 95-IENPRQSG C(1)GAAV TAG-121 | A338C(1) |
| SEQ L7-8 | 95-IENPRQSG C(1)AAAV TAG-121 | A338C(1) |
| SEQ L7-9 | 95-IEQPRQSG C(1)AAAV TAG-121 | A338(1) |
| SEQ L7-14 | 95-IEQPRQSG C(1)AAAV TAG-121 | A338C(1) |
| SEQ L7-7 | 95-IEQPRQSG C(1)AAFV TAG-121 | A338C(1) |
| Intraprotomerical disulfide bond and substitution of E96 and/or R99 | | |
| SEQ m37/m40 | 95-IMQPIQSG C(1)GAGA TAG-121 | A338C(1), E433S, E431S |
| SEQ L14-1 | 95-IANPSQSG C(1)GAGA TAG-121 | A338C(1) |
| SEQ L14-2 | 95-IANPSQSG C(1)GAAV TAG-121 | A338C(1) |
| Intra- + interprotomerical disulfide bonds | | |
| SEQ m36a | 95-IEQPRQSG C(1)GAGA TC(2)G-121 | A338C(1), Q426'C(2) |
| Intraprotomerical disulfide bond and substitution of E96 and/or R99 | | |
| SEQ L7-10 | 95-IC(1)QPSQSG C(2)AAAV TAG-121 | T328'C(1), A338C(2) |
| SEQ L7-11 | 95-IC(1)QPSQSG C(2)AAAV TAG-121 | S428'C(1), A338C(2) |

TABLE 1a-continued

Examples of variations of the single-chain linker joining F2 and F1 domains. The indel operation causes the deletion of the fusion peptide and has the effect of a net shortening of the ectodomain sequence. Cysteines marked with matching numbers, such as C(1) or C(2), form disulfide bonds between F1 and F2 domains. Cysteines marked with a prime ('C) are located on the neighboring protomer.

| Construct name | Sequence replacing residues 95-121 of SEQ ID NO: 1 | Additional substitution in SEQ ID NO: 1 |
|---|---|---|
| SEQ L7-12 | 95-IC(1)QPRQSG C(2)AAAV TAG-121 | T328'C(1), A338C(2) |
| SEQ L7-13 | 95-IC(1)QPRQSG C(2)AAAV TAG-121 | S428'C(1), A338C(2) |
| SEQ L7-15 | 95-IC(1)QPRQSG AAC(2)AV TAG-121 | T328'C(1), A338C(2) |
| Single-chain X-net deletion of 12 aa residues vs F0 ectodomain Intraprotomerical disulfide bridge | | |
| SEQ scF_A1_1.3v6.B | 95-IENPRQC(1)S GAGA TAG-121 | A339C(1) |
| L11-type single-chain-net deletion of 13 aa residues vs F0 ectodomain Intraprotomerical disulfide bridge | | |
| SEQ scF_A1_1.2.A | 95-IENPRQSG C(1)GA TAG-121 | A338C(1) |
| SEQ scF_A1_1.2.B | 95-IENPRQSI C(1)GA TAG-121 | A338C(1) |
| SEQ scF_A1_1.2.C | 95-IENPRQSP C(1)GA TAG-121 | A338C(1) |
| SEQ scF_A1_1.3.A | 95-IENPRQGC(1) GGA TAG-121 | A338C(1) |
| SEQ scF_A1_1.3v5.B | 95-IENPRQC(1)G AGA TAG-121 | A339C(1) |
| Combined intra- and inter-protomerical disulfide bonds | | |
| SEQ L11-3 | 95-IC(1)QQSGC(2)G AAV TAG-121 | T328'C(1), A338C(2) |
| SEQ L11-5 | 95-IC(1)QPSGC(2)A AAV TAG-121 | T328'C(1), A338C(2) |
| SEQ L11-5-102G | 95-IC(1)QPSGC(2)G AAV TAG-121 | T328'C(1), A338C(2) |
| Single-chain (shortening by 15 aa) Intraprotomerical disulfide bond | | |
| SEQ scF_A1_2.1 | 95-IENPRQSC(1) VTAG-121 | A338C(1) |
| Intra- and inter-protomerical disulfide bridge and E96 mutated | | |
| SEQ scF_A1_2.2v1 | 95-IC(1)NPRQSC(2) VTAG-121 | S428'C(1), A338C(2) |
| SEQ scF_A1_2.3v1 | 95-IC(1)NPRTSC(2) VTAG-121 | S428'C(1), A338C(2) |
| Single-chain Y-net deletion of 16 aa residues vs F0 ectodomain Interprotomerical disulfide bridge | | |
| SEQ L12-4 m38c/39c | 95-IC(1)NSAAAV TAG-121 | T328'C(1) |
| SEQ L12-5 m51 | 95-IC(1)NTAAAV TAG-121 | T328'C(1) |

TABLE 1b

Examples of the single-chain-linkers, joining F2 and F1domains, presented in a general pattern. Cysteines marked with matching numbers, such as C(1) or C(2), form disulfide bonds between F1 and F2 domains. Cysteines marked with a prime ('C) are located on the neighboring protomer.

| Construct name | Sequence replacing residues 95-119 of SEQ ID NO: 1 | Additional substitution in SEQ ID NO: 1 |
|---|---|---|
| Single-chain delta -11 aa (L7) | 95-I[AC(1)EM][NQ]P[RISP]QSG [AC(2)][AG][AC(2)GS][AGSF][AV]T-119 | T328'C(1) or S428'C(1), A338C(2) |

TABLE 1b-continued

Examples of the single-chain-linkers, joining F2 and F1domains, presented in a general pattern. Cysteines marked with matching numbers, such as C(1) or C(2), form disulfide bonds between F1 and F2 domains. Cysteines marked with a prime ('C) are located on the neighboring protomer.

| Construct name | Sequence replacing residues 95-119 of SEQ ID NO: 1 | Additional substitution in SEQ ID NO: 1 |
|---|---|---|
| Single-chain delta -12 aa (L6) | 95-I ENPRQC(1)S + GAG[AV]-T119 | A339C(1) |
| Single-chain delta -13 aa (L11) | 95-I[ES][NQ][PQ][RS][QG][C(1)G][AC(1)G][AG][AG][AV]T-119 | A338C(1) or A339C(1) |
| | 95-IENPR[IQ][SG][GIPC(1)][C(1)G][G][AV]T-119 | A338C(1) |
| | 95-IC(1)[NQ][PQ][GS][GS]C(2)A[AG][AG][AV]T-119 | T328'C(1), A338C(2) |
| Single-chain delta -15 aa (L2) | 95-I[C(1)E][NQ]P[RS][GQT][SC(2)][GC(2)][AV]T-119 | S428'C(1), A338C(2) |
| Single-chain delta -16 aa (L12) | 95-IC(1)[NQ][ST][AG]A[AG]VT-119 | T328'C(1) |

In some embodiments, the pre-fusion conformation of the single-chain F protein may be covalently stabilized by introducing at least one non-natural intra- or inter-protomer disulfide bond. For instance, a non-natural disulfide bond may be introduced between a cysteine residue of the heterologous peptide linker located between the F2 and F1 domains and a cysteine residue of the F1 domain. The first cysteine residue can be at any position of said linker, for example, at position 1, 2, 3 or 4, preferably at position 1, which corresponds to position 103 of SEQ ID NO: 1. Alternatively, the first cysteine residue can be introduced in the F2 domain at position 96, or 101, or 102 of SEQ ID NO: 1. In the most preferred embodiment, the cysteine at position 103 forms a non-natural disulfide bond with the cysteine substitution of the alanine at position 338 of the native hMPV F sequence of SEQ ID NO: 1. This S—S-bond can stabilize the pre-fusion conformation of the single-chain F protein by fixing the loop between F2 and F1 within the hydrophobic trimeric cavity. Such loop fixation mimics the positioning effect of the internalized cleaved N-termini of F1 in the native hMPV protein. In some embodiments, the single-chain hMPV F protein may comprise further cysteine substitution(s) that can introduce non-native inter-protomer disulfide bonds, e.g. to stabilize a protein trimer by linking it covalently.

In yet one embodiment, the single-chain hMPV F protein lacks amino acid residues 1 to 16 at the N-terminus of the F1 domain of SEQ ID NO: 3, encompassing the entire or partial sequence of the fusion peptide FP. Preferably, the single-chain hMPV F protein lacks the amino acid residues at positions 103-118 of the native hMPV F protein sequence of SEQ ID NO: 1. The deletion of FP further stabilizes the pre-fusion conformation of the single-chain hMPV F protein.

In some embodiments, the single-chain hMPV F protein may comprise one or more further modification(s). On the one hand, the additional modification may compensate an altered geometry of the single-chain hMPV F protein. On the other hand, the additional modification may further stabilize the pre-fusion conformation. The additional modifications can comprise one or more amino acid substitutions, insertions and/or deletions. Among modifications, the conservative substitutions may be, but not necessarily are, preferred. The following groups of substitutions are considered conservative:

1) alanine (A), serine (S), threonine (T);
2) aspartic acid (D), glutamic acid (E);
3) asparagine (N), glutamine (G);
4) arginine (R), lysine (K);
5) leucine (L), isoleucine (I), methionine (M), valine (V); and
6) phenylalanine (F), tyrosine (Y), tryptophan (W).

In one embodiment, the additional modification, which stabilized the single-chain hMPV F protein, is the substitution of a glutamine residue for an asparagine residue at position 97 (N97Q) of the native hMPV F protein sequence of SEQ ID NO: 1.

In another embodiment, the additional modification of the single-chain F ectodomain may comprise one or more cavity filling substitution(s), including but not limited to substitutions at positions 49, 67, 137, 159, 147, 160, 161 and/or 177 relative to the native hMPV F protein sequence of SEQ ID NO: 1. In particular, the cavity filling substitution can be selected from, but is not limited to, a T49M substitution, an I67L substitution, an I137W substitution, an A147V substitution, an A159V substitution, a T160F substitution, an A161M substitution or I177L substitution. Additionally, combinations of two or more cavity filling substitutions are possible. In one particular embodiment, the combination comprises the T160F and I177L substitutions. In another particular embodiment, the combination comprises the T49M, I67L and A161M substitutions. In yet particular embodiment, the combination comprises the T49M, A161M, I137W, A147V, A159V and I177L substitutions.

Rigidification of the HRA α3 by cavity filling. In native and cleaved F protein the N-terminal part of F1 bears the HRA containing domain, a long extended helix in the thermodynamically more stable post-fusion F protein, but folded with several distinct small helices, even bearing a beta hairpin element, in the pre-fusion conformation ("loaded spring"). Additional contacts of this element may allow for stabilization of the protein in pre-fusion conformation. To fill up a cavity beneath the HRA α3 two small residues were replaced with the space-filling aliphatic residue methionine at positions T49M and A161M to form a complementary pair packing together and to strengthen the aliphatic fixation of this surface-located helix. Mutations at the position 161 have been reported for the hMPV F pre-fusion ectodomain by Battles et al., 2017 leading either to non-expressing F protein subunits (A161F) or to subunits poorly reacting with the MPE8 antibody (A161L) (see Battles et al. 2017. *Nat. Commun.* 8(1): 1528).

Covalent attachment of the HRA α4 by a disulfide-bond. HRA α4 extends to the tip of the F protein and is situated C-terminal of the beta-hairpin element following HRA α3 in the pre-fusion structure. All of these elements participate in the transformation to the long alpha-helical element in the post-fusion conformation, which includes a movement away from the head domain towards the host cell membrane in the fusion process of the virus. Here a disulfide bridge is introduced between the HRA α4 helical element (K166C) to a long beta-strand provided by the F2 portion (E51C). This change modifies two charged residues, which participate in a polar network including contacts to HRA α3. An additional modification, S266D, was introduced to allow for a partial reconstitution of the disturbance in the salt-bridge network by this disulfide bond-forming mutation.

Rigidification of the HRA α2-α3 by introduction of tryptophan. HRA α2-α3 forms a bent substructure on the pre-fusion hMPV F protein (while being part a long helix in the post-fusion conformation). Rigidification of this bend would hinder transformation to the post-fusion conformation. For this bend similarly folded substructures can be observed, in which the hMPV F protein I137 is tryptophan in the analog position and providing a more densely packed substructure e.g. in a crystal structure of the N-terminal part of cleaved Protein C Inhibitor bound to Heparin (PDB: 3DY0, W271 of chain A). Based on the homology modeling and molecular simulation, two further mutations A147V and A159V were introduced to provide extra space filling in this substructure to force the tryptophan side chain into the orientation observed in the Protein C Inhibitor structure, which allows additional stabilization of the tryptophan side-chain amide with a polar contact to S149 (an asparagine in Protein C inhibitor). Also, the analog positions to A147 and A159 provide residues with space-filling side-chains.

In some embodiments, the single-chain hMPV F protein may comprise one or more further stabilizing substitution(s), for example, substitutions leading to formation of a non-natural hydrogen bond(s), variant core packing or a salt bridge(s). In particular, the modified single-chain hMPV F protein may comprise the E80N, F258I and/or G294E substitutions. The E80N substitution can establish an inter-protomer H-Bond to D224' (the prime denoting the neighbor protomer) and reduce repulsion with D209. On the other hand, the E80N substitution enhances the recombinant expression of the single-chain hMPV F protein. Another modification, which is helpful for increasing a yield of the recombinant protein, is the G294E substitution.

In some embodiments, the substitution of the vicinal residues I480 and L481 for cysteine residues allows introduction of three disulfide bonds across the three protomers in the form of a covalent ring. The covalently linked trimer is supposed to be more stable than the foldon trimerized particle. Formation of a functional ring requires that all three disulfide bonds, or in case of multiple rings at least one disulfide bond between each protomer, are formed. The distance of the ring to the foldon domain is short and the foldon attachment position optimized for a more rigid geometry.

In preferred embodiment, the following substitution combinations are as follows:

N97Q, R102G and G294E (L7F_A1_23) (e.g. as present in SEQ ID NO: 5)

N97Q, R102G, T160F, I177L and G294E (sF_A1_K_L7) (e.g. as present in SEQ ID NO: 6);

N97Q, R102G, T49M, I67L, A161M, E80N, F258I and G294E (L7F_A1_31) (e.g. as present in SEQ ID NO: 7);

N97Q, R102G, T49M, I67L, A161M, E51C, K166C, S266D, G294E, I480C and L481C (L7F_A1_33) (e.g. as present in SEQ ID NO: 8), and N97Q, R102G, T49M, A161M, I137W, A159V, A147V I177L and G294E (L7F_A1_4.2) (e.g. as present in SEQ ID NO: 9).

Protein Trimer

In some embodiments, the modified single-chain hMPV F proteins of the invention differ from the native hMPV F protein in that they do not possess a transmembrane domain and a cytoplasmic tail. Nevertheless, in some embodiments, the modified single-chain hMPV F proteins can form mono- or hetero-trimers. In order to form a trimer a trimerization helper domain, so called foldon, may be inserted in the C-terminal part of the F ectodomain. Addition of the trimerization helper, which retains the soluble state to the C-terminus of the subunit ectodomain, supports formation of a stable trimeric and soluble protein trimer.

In one embodiment, the foldon domain may derive from fibritin of T4 bacteriophage and comprises the sequence of SEQ ID NO: 10. In another embodiment, the fibritin foldon may be modified by insertion of one or more N-glycosylation site(s) (motif NxT/S, wherein "x" any amino acid residue except proline), which could help to hide hMPV non-specific epitope(s). Some non-limiting examples of modified foldon domain sequences are as following:

```
Foldon
                                          (SEQ ID NO: 10)
GYIPEAPRDGQAYVRKDGEWVLLSTFL

Foldon-glyc-1
                                          (SEQ ID NO: 29)
GYIPEAPRNGTAYVRKDGEWVLLSTFL

Foldon-glyc-2
                                          (SEQ ID NO: 30)
GYIPEAPRDGQAYVRKNGTWVLLSTFL

Foldon-glyc-3
                                          (SEQ ID NO: 31)
GYIPEAPRDGQAYVRKDGNWTLLSTFL

Foldon-glyc-4
                                          (SEQ ID NO: 32)
GYIPEAPRNGTAYVRKNGTWVLLSTFL

Foldon-glyc-5
                                          (SEQ ID NO: 33)
GYIPEAPRNGTAYVRKDGNWTLLSTFL.
```

Alternatively, the foldon domain may possess structural elements from the GCN4 leucine zipper (Harbury et al. 1993. Science 262:1401) or monomers of self-assembling nanoparticles allowing attachments around a C3 axis (e.g. ferritin and lumacine synthase).

In another embodiment, the foldon domain is attached to the C-terminus of the F protein, replacing its transmembrane and cytosolic domains. The glycine residue at the N-terminus of the foldon may be attached to the F1 domain directly or via a peptide linker of a various length, which may include at least one protease site. Longer linkers allow to decouple the movement of the foldon domain, but are less potent to support keeping the helices of the HRB region (stalk) at a defined position. The helices could undergo movements with transversal displacement and bending of the trimerization helper domains into an angle off-axis of the main c3 axis of the particle. Shorter linkers allow more rigid attachment of the foldon domain with stronger fixating effect on the three helices of the stalk domain.

In particular, the foldon domain can be attached via an alanine residue inserted after the S482 of the native hMPV F protein sequence of SEQ ID NO: 1. This allows to keep S482 as C-terminal helix cap and to reproduce the local geometry of the foldon interface. Such geometry may be achieved by the foldon attachment via a short linker, for example, the short linker called "VSL" or "VSA", consisting of the sequence ILSA (SEQ ID NO: 34) and CCSA (SEQ ID NO: 35), respectively. Alanine (A483) therein is in an analog position to the alanine at n−2 position to the tyrosine in the crystal structure PDB:1AVY (corresponding to position 2 in SEQ ID NO: 10) and shows similar contacts to the tyrosine sidechain in structure models. Additionally, the short linker "VSL" or "VSA" may be used in combination with other mutations, e.g. amino acid substitutions in the close vicinity to the linker. For example, the combination of the linker "VSA" with the substitutions C480 and C481 allows to covalently link three protomers via formation of the disulfide ring across the three protomers. In this geometry the cysteine residues of the disulfide ring are kept in spacial proximity, and therefore formation of the fully closed rings, which increases the overall stability of the protomer trimer is supported. An example for a less rigid foldon attachment retains residues 483-485 of SEQ ID NO: 1 (ILSSAE or CCSSAE with a disulfide ring). Some examples of modified foldon linkers forming more than one cysteine ring are shown below:

(SEQ ID NO: 36)
480-CCKQTNECCKNLERAVSA-496

(SEQ ID NO: 37)
480-CCRELKECCKNLENAVSA-496

(SEQ ID NO: 38)
480-CCRELKDCCKNLENAVSA-496

-continued (SEQ ID NO: 39)
480-CCRELKDCCKNLERAVSA-496

(SEQ ID NO: 40)
480-CCRELKDCCKQLNKAVSA-496

(SEQ ID NO: 41)
480-CCRELKECCKQLNKAVSA-496

Other non-limiting examples of short linkers are: GG, SG, GS, GGG, GGA, GGS, SGG, SSG, SGS, SGA, GGA, SSA and SGGS. Such linkers may be used in combinations with cleavage sites, introduced by e.g. replacement of A496. The cleavage site is preferably a thrombin cleavage site, the TEV-cleavage site (Tobacco etch virus protease) or the Xa-cleavage site (Factor Xa) disclosed in Table 2.

TABLE 2

| Description | Cleavage motif | SEQ ID NO |
|---|---|---|
| Thrombin-cleavage site | LVPR-GS | SEQ ID NO: 42 |
| TEV-cleavage site | ENLYFQ-G | SEQ ID NO: 43 |
| Factor Xa cleavage site | IEGR- | SEQ ID NO: 44 |

In some embodiments, for easier purification of the recombinant protein the single-chain polypeptide may comprise any purification tag sequences known in the prior art. Examples of polypeptides that aid purification include, but are not limited to, a His-tag, a myc-tag, an S-peptide tag, a MBP tag, a GST tag, a FLAG tag, a thioredoxin tag, a GFP tag, a BCCP, a calmodulin tag, a streptavidin tag, an HSV-epitope tag, a V5-epitope tag and a CBP tag. The proteins of the present invention preferably comprise the His and/or streptavidin tags having the sequences of SEQ ID NO: 11 and SEQ ID NO: 12, respectively.

The non-limiting examples of combinations that may be applied are shown in Table 3 that may allow forming a parallel three-helix-bundle with two disulfide rings. Trimerization could occur with sequence portion containing 480-495 residues, but can be facilitated by the presence of the foldon domain. Availability of cysteine rings allows forming the disulfide bonds making covalent connection between three protomers. After that the trimerization helper function becomes obsolete and the folder could be cleaved off with the advantage that the immunogenic side-effects from a heterologous sequence (and e.g. non-hMPV) can be avoided.

TABLE 3

| SEQ ID NO: | Foldon sequence | Combination |
|---|---|---|
| SEQ ID NO: 45 | 480-CCKQTNECCKNLERAVS-495 | A + Foldon +/- cleavable His-Tag |
| SEQ ID NO: 46 | 480-CCKQTNECCKNLERAVS-495 | SGRENLYFQSGA + Foldon +/- cleavable His-Tag |
| SEQ ID NO: 47 | 480-CCKQTNECCKNLERAVS-495 | GLVPRGG + Foldon +/- cleavable His-Tag |
| SEQ ID NO: 48 | 480-CCRELKECCKNLENAVS-495 | A + Foldon +/- cleavable His-Tag |
| SEQ ID NO: 49 | 480-CCRELKECCKNLENAVS-495 | SGRENLYFQSGA + Foldon +/- cleavable His-Tag |
| SEQ ID NO: 50 | 480-CCRELKECCKNLENAVS-495 | GLVPRGG + Foldon +/- cleavable His-Tag |

In some embodiments, the recombinant hMPV F protein may comprise or consist of an amino acid sequence having at least 85%, 90%, 95%, 98% or 99% sequence identity to the amino acid sequence any of SEQ ID NOs: 5 to 9 or 24 to 28, e.g. wherein the percentage sequence identity is determined over the full length of the reference sequence. The recombinant single-chain hMPV F protein may comprise an F2 domain comprising or consisting of an amino acid sequence having at least 85%, 90%, 95%, 98% or 99% sequence identity to the amino acid sequence of SEQ ID NO: 2. The recombinant single-chain F protein may comprise an F1 domain comprising or consisting of an amino acid sequence having at least 85%, 90%, 95%, 98% or 99% sequence identity to the amino acid sequence of SEQ ID NO: 3, preferably with respect to at least residues 17-437 or 17-388 of SEQ ID NO: 3.

Encoding Nucleic Acids and Vectors

The present application provides isolated nucleic acid molecules encoding the recombinant hMPV proteins of the present invention. The nucleic may acid encode e.g. a polypeptide comprising for example a) a (modified) F1 domain of the hMPV F protein; b) a (modified) F2 domain of the hMPV F protein, c) a heterologous peptide linker located between F1 and F2 domains; d) a trimerization helper domain; and, optionally, e) a purification tag, wherein the F1 and F2 domains are covalently linked by at least one non-natural disulfide bond introduced between a cysteine in the linker and a cysteine in the F1 domain. The nucleic acids encoding the proteins of the present invention may comprise or consist of the sequences of SEQ ID NOs 19 to 23.

The present application also includes isolated nucleic acid molecules encoding proteins having at least 85%, 90%, 95%, 98% or 99% sequence identity to the amino acid sequence any of SEQ ID NOs 5 to 9 or 24 to 28. The present application also includes isolated nucleic acid molecules having at least 85%, 90%, 95%, 98% or 99% sequence identity to the sequence of SEQ ID NOs 19 to 23, e.g. wherein the percentage sequence identity is determined over the full length of the reference sequence.

The present application also provides vectors comprising the isolated nucleic acid molecules for expression of the recombinant proteins of the present invention. The present invention also provides expression systems designed to assist in expressing and providing the isolated polypeptides. The present application also provides host cells for expression of the recombinant hMPV F proteins of the present invention. The host cell may be a prokaryote. The prokaryote may be e.g. *E. coli*. The host cell may be an eukaryotic cell.

Immunogenic Compositions and Formulations

The recombinant single-chain hMPV F proteins of the present invention are immunogenic and can induce neutralizing antibodies recognizing the native hMPV F protein. The present disclosure also includes immunogenic fragments of the recombinant hMPV proteins and immunogenic proteins having at least 85% sequence identity to the proteins of SEQ ID NOs 5 to 9 or 24 to 28.

The present disclosure also provides immunogenic compositions or vaccines comprising the recombinant hMPV F proteins, or isolated DNA molecules encoding the hMPV F protein, or vectors of the invention, comprising an acceptable carrier and/or excipient or stabilizers known in the art (see generally Remington, 2005. The Science and Practice of Pharmacy, Lippincott, Williams and Wilkins). An immunogenic composition is any composition of material that elicits an immune response in a mammalian host when the immunogenic composition is injected or otherwise introduced. The immune response may be humoral, cellular, or both. A booster effect refers to an increased immune response to an immunogenic composition upon subsequent exposure of the mammalian host to the same immunogenic composition. A humoral response results in the production of antibodies by the mammalian host upon exposure to the immunogenic composition.

The immunogenic compositions or vaccines may further comprise an adjuvant. The adjuvant can be selected based on the method of administration and may include mineral oil-based adjuvants such as Freund's complete and incomplete adjuvant, Montanide incomplete Seppic adjuvant such as ISA, oil in water emulsion adjuvants such as the Ribi adjuvant system, oil-in-water emulsion adjuvants such as MF59® (Novartis AG) or Addavax™ (InvivoGen) (Ott G. et al. 1995. *Pharm Biotechnol* 6: 277-96), monophosphoryl lipid A (MPL) (Cluff C W. 2010. *Adv Exp Med Biol* 667:111-23), aluminum salt adjuvant (alum) (e.g., as described in WO 2013/083726), syntax adjuvant formulation containing muramyl dipeptide (MDP), polycationic polymer, especially polycationic peptide, especially polyarginine or a peptide containing at least two LysLeuLys motifs, especially KLKLLLLLKLK (SEQ ID NO: 55), immunostimulatory oligodeoxynucleotide (ODN) containing non-methylated cytosine-guanine dinucleotides (CpG), e.g. CpG 1018 (Dynavax), in a defined base context (e.g. as described in WO 96/02555) or ODNs based on inosine and cytidine (e.g. as described in WO 01/93903), or deoxynucleic acid containing deoxy-inosine and/or deoxyuridine residues (as described in WO 01/93905 and WO 02/095027), especially oligo$(dIdC)_{13}$ (SEQ ID NO: 56) (as described in WO 01/93903 and WO 01/93905), IC31® (Valneva SE) as described in WO 04/084938 and Olafsdottir et al. 2009 (*Scand J Immunol.* 69(3): 194-202), neuroactive compound, especially human growth hormone (described in WO 01/24822) and others described in Sarkar I. et al. 2019 (*Expert Rev Vaccine:* 18(5): 505-521), or combinations thereof, such as AF03, AS01, AS03 and AS04 described in Giudice G D et al. 2018 (*Seminars in Immunology* 39: 14-21). Some combinations are according to the ones e.g. described in WO 01/93905, WO 02/32451, WO 01/54720, WO 01/93903, WO 02/13857, WO 02/095027 and WO 03/047602. In one preferred embodiment, the adjuvant is aluminium hydroxide or aluminium salt that induces strong antibody and Th2-biased immune response. In another preferred embodiment, the adjuvant is an adjuvant or composition of adjuvants that induce mixed Th1/Th2 responses, such as MF59® or Addavax™, MPL/alum and IC31®.

The present disclosure also provides pharmaceutical compositions comprising the recombinant hMPV F proteins of the invention, further comprising a pharmaceutically acceptable carrier and/or excipient. The pharmaceutical composition may further comprise pharmaceutically acceptable carriers and/or excipients. The pharmaceutically acceptable carriers and/or excipients may include buffers, stabilizers, diluents, preservatives, and solubilizers (see Remington's Pharmaceutical Sciences, by E. W. Martin, Mack Publishing Co., Easton, PA, 15th Edition, 1975).

Acceptable carriers, excipients, or stabilizers are nontoxic to recipients at the dosages and concentrations that are administered. Carriers, excipients or stabilizers may further comprise buffers. Examples of excipients include, but are not limited to, carbohydrates (such as monosaccharide and disaccharide), sugars (such as sucrose, mannitol, and sorbitol), phosphate, citrate, antioxidants (such as ascorbic acid and methionine), preservatives (such as phenol, butanol, benzanol; alkyl parabens, catechol, octadecyldimethylbenzyl ammonium chloride, hexamethonium chloride, resorcinol, cyclohexanol, 3-pentanol, benzalkonium chloride, benzethonium chloride, and m-cresol), low molecular weight polypeptides, proteins (such as serum albumin or immunoglobulins), hydrophilic polymers amino acids, chelating agents (such as EDTA), salt-forming counter-ions, metal complexes (such as Zn-protein complexes), and non-ionic surfactants (such as TWEEN™ and polyethylene glycol).

The immunogenic compositions of the present invention elicit an immune response in a mammalian host, including humans. The immune response may be either a cellular dependent response or an antibody dependent response or both. These immunogenic compositions are useful as vaccines and may provide a protective response against the hMPV infection.

The disclosure further provides immunogenic compositions or vaccines comprising one or more additional antigen(s) derived from at least one different infectious virus, especially virus that causes a respiratory tract infection, such as hMPV, RSV (Respiratory Syncytial Virus), PIV3 (ParaInfluenza Virus type 3), influenza virus or a coronavirus (such as SARS-CoV, SARS-CoV-2, MERS or alike). Preferably, the additional antigen is the RSV F protein, PIV3 F protein, influenza hemagglutinin or coronavirus S-protein.

The immunogenic recombinant proteins, isolated DNA or RNA molecules, vectors and immunogenic compositions or vaccines disclosed herein are suitable for use as a medicament, particularly for the prophylactic and/or therapeutic treatment of viral respiratory tract infections and associated diseases, especially infections and disease caused by hMPV.

Methods of production of the recombinant hMPV F proteins or isolated nucleic acid (DNA or RNA) molecules encoding the hMPV F protein or immunogenic compositions (vaccines) are encompassed in the present disclosure. Methods of generating an immune response in a subject and methods of treating, inhibiting or preventing respiratory tract infections, especially caused by hMPV, are also included.

The invention will now be described by way of examples only with reference to the following non-limiting embodiments.

EXAMPLES

Example 1: Design of the Modified F Proteins

Structural Models

Design of the mutated hMPV F proteins in the stabilized pre-fusion conformation was done based on homology models derived from available crystal structures of the pre-fusion RSV F (PDB:4JHW and 4MMV, also 4MMU, 4MMS), pre-fusion PIV-5 F (PDB:5GIP), pre-fusion hMPV F (PDB: 5WB0) and post-fusion hMPV F (PDB:5L1X) proteins, representing models of different transition phases of the fusion process. The foldon domain was adapted from the model PDB:2IBL. Model construction and structural analysis was performed by using the open-source version of PyMol structure editor package (Schrodinger LLC, https://github.com/schrodinger/pymol-open-source). Models were refined with the NAMD modeling package (Phillips et al. 2005. *J Comput Chem.* 26(16):1781-802) and the charmm36 forcefield (McKerell et al. 1998. *J Phys Chem B.* 102(18): 3586-3616) or Gromacs (Berendsen et al. 1995. *Comp. Phys. Comm.* 91:43-56; Hess et al. 2008, *J. Chem Theory Comput.* 4, 435-447; www.gromacs.org)/OPLS-AA (Jorgensen W L, Yale Univ.). Candidate models were typically refined in a protocol applying after in vacuo relaxation in a NVT, NPT simulation sequence for a total of 13 ns, with application of three cycles of symmetry annealing (adapted from Anishkin et al. 2010. *Proteins.* 78(4): 932-949) followed by free sampling and energy minimization.

Example 2: Production of the Recombinant F Proteins

Strains

The native hMPV F protein can be selected from any hMPV strain and any serotype represented by the sequences of SEQ ID NOs 1, 13 to 18, or variants thereof. In certain exemplary embodiments, the hMPV F protein derives from the strain NL/1/00, serotype A1, represented by SEQ ID NO: 1 and strain CAN97-83, serotype A2, represented by SEQ ID NO: 14.

Expression Vectors

The plasmid pVVS 1371 used for cloning contains:

an HS4 insulator sequence from chicken β-globin locus, two CMV promoters, two chimeric introns, downstream of the CMV promoters, composed of the 5'-donor site from the first intron of the human β-globin gene and the branch and 3'-acceptor sites from the intron of an immunoglobulin gene heavy chain variable region. The sequences of the donor and acceptor sites, along with the branch point site, were adapted to match the consensus sequences for splicing. The intron is located upstream of the cDNA insert in order to prevent utilization of possible cryptic 5'-donor splice sites within the cDNA sequence, the bovine growth hormone polyadenylation signal sequence (bGH A), the neomycin phosphotransferase gene from Tn5 under the regulation of the SV40 enhancer and early promoter region, the HSV TK polyadenylation signal of the thymidine kinase gene of Herpes Virus is located downstream of the neomycin phosphotransferase gene, a kanamycin resistance gene under the regulation of a bacterial promoter, and a pUC origin of the replication.

The coding sequence of the wild type F protein was isolated from the hMPV strain NL/1/00, sublineage A1 and was codon-optimized for expression in CHO cells. The coding sequences of the wild type and modified F proteins were cloned into pVVS1371 plasmid for transient or stable protein expression in CHO cells.

Briefly, the coding sequences were cloned between the chimeric intron and the bGH A polyadenylation site of the pVVS1371 vector using the restriction sites SalI and PacI. The vector and the synthetized coding sequence (synthesis was done by GeneArt) were digested with SalI and PacI before purification on an agarose gel. The fragments were ligated with T4 DNA ligase and the ligation product was used to transform Max efficiency DH5α competent cells. Selected clones were tested for designed mutations by sequence analysis.

Expression in CHO Cells

The protein expression is based on transient transfection of CHO cells using a MaxCyte® STX Scalable Transfection System device and following experimental recommendations of the supplier. Briefly, prior to electroporation, CHO cells are pelleted, suspended in MaxCyte® electroporation buffer and mixed with corresponding expression plasmid DNA. The cell-DNA mixture is transferred to a cassette processing assembly and loaded onto the MaxCyte® STX Scalable Transfection System. Cells are electroporated using the "CHO" protocol preloaded in the device and immediately transferred to culture flasks and incubated for 30 to 40 minutes at 37° C. with 8% $CO_2$. Following the recovery period, cells are resuspended at high density in EX-CELL ACF CHO medium (Sigma Aldrich). Post-electroporation cell culture is carried out at 37° C., with 8% $CO_2$ and orbital shaking.

The production kinetics consist of decreasing the culture temperature to 32° C. and feeding the transfected cells daily with a fed-batch medium developed for transient protein expression in CHO cells (CHO CD EfficientFeed™ A (ThermoFischer Scientific), supplemented with yeastolate, glucose and glutaMax). After about 7 to 14 days of culture, cell viability is checked and conditioned medium is harvested after cell clarification corresponding to two runs of centrifugation at maximum speed for 10 minutes. Clarified product is filtered through a 0.22 μm sterile membrane and stored at −80° C. before protein purification.

Protein Detection by Intracellular Immunostaining

At day 7 post transfection, cells are washed once in PBS and fixed for 10 minutes in 4% paraformaldehyde at room temperature. Fixed cells are permeabilized in BD Perm wash for 15 minutes at room temperature and incubated with the primary antibody diluted in BD Perm wash for 1 hour at 4° C. Finally, a secondary antibody coupled to a fluorescent marker is added for 1 hour at 4° C. and stored in PBS at 4° C. until analysis by flow cytometry (MacsQuant Analyzer, Miltenyi Biotec). As the primary antibody the MPE8 N113S antibody (PRO-2015-026-01) specifically recognizing the pre-fusion conformation of the hMPV F protein, or the DS7 IgG1 antibody (PRO-2016-003) recognizing both pre- and post-fusion hMPV F protein have been used. The fluorescent FITC secondary antibody was goat anti-mouse IgG+IgM (JIR 115-096-068).

Protein Purification

Frozen supernatant is brought to a room temperature and dialyzed with a standard grade regenerated cellulose dialysis membrane Spectra/Por® 1-7 CR (MWCO: 3.5 kDa) (Spectrum) against PBS. Subsequently, it is equilibrated with 50 mM $Na_2HPO_4$ buffer at pH 8.0, 300 mM NaCl and purification of the protein is performed using Immobilized Metal ion Affinity Chromatography (IMAC) followed by gel filtration chromatography.

For IMAC, agarose resin containing $Ni^{2+}$ (His GraviTrap) is packed into chromatography columns by the manufacturer (GE Healthcare). The resin is washed with two volumes of deionized water and equilibrated with three volumes of equilibration and wash buffer (20 mM sodium phosphate, pH 7.4, with 0.5 M sodium chloride and 20 mM imidazole) as indicated by the manufacturer. After sample loading the column is washed with 10 mL of wash buffer. The His-tagged protein is eluted from the column using 3-10 column volumes of elution buffer as indicated by the manufacturer (50 mM sodium phosphate, pH 8.0, with 0.5 M sodium chloride and 500 mM imidazole). Eluate is then filtered on a 0.22 μm filter and dialyzed twice in Slide-A-lyzer™ Dialysis cassettes against a storage buffer (50 mM $Na_2HPO_4$, 300 mM NaCl, 5 mM EDTA, pH 8.0) before being aliquoted and stored at −20° C.

Figure 4:
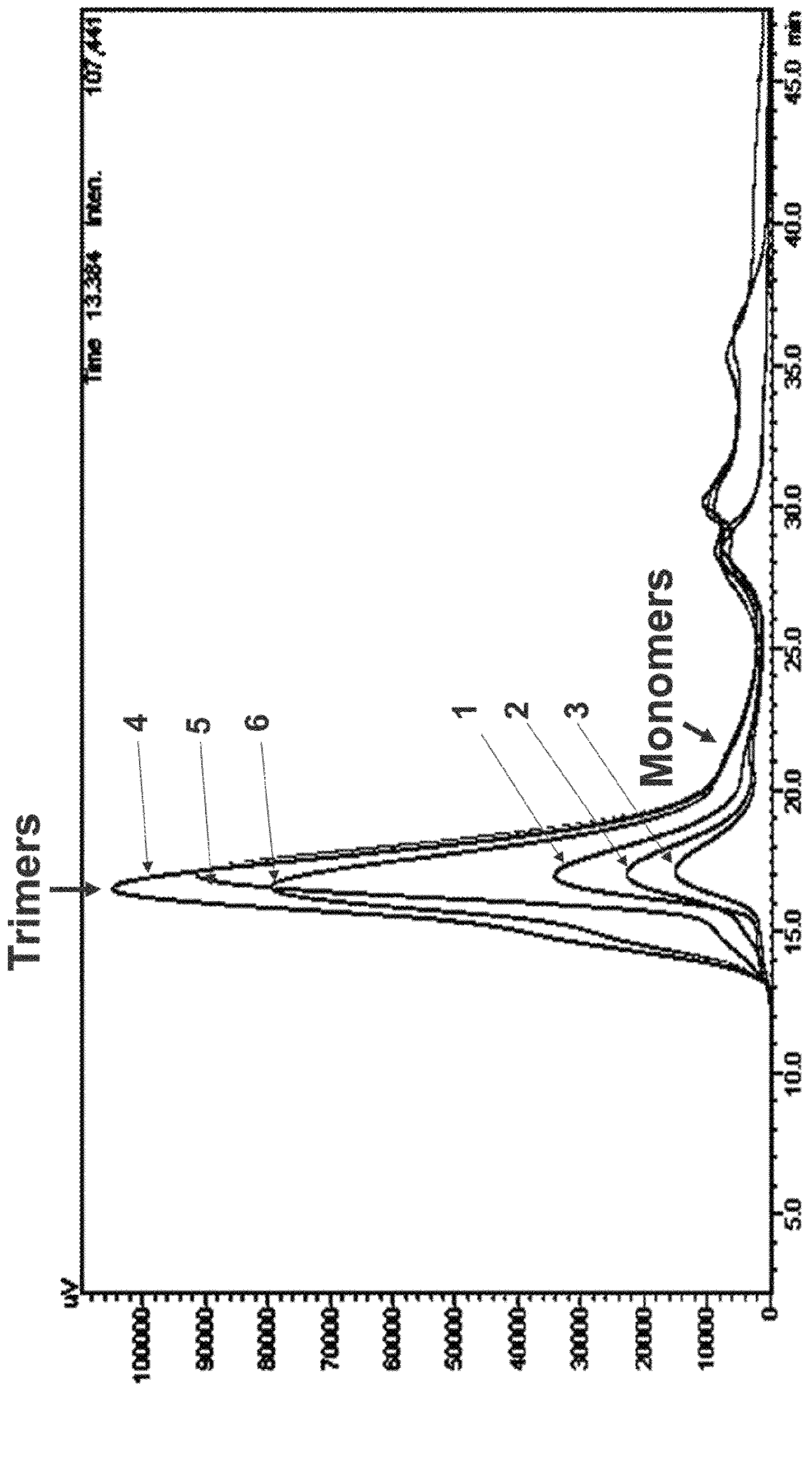
FIG. 4 shows analysis of the recombinant hMPV F proteins by SE-HPLC. 1—sF_A1_K-E294, 2—sF_A1_K_L7, 3—L7F_A1_4.2, 4—L7F_A1_31, 5—L7F_A23, 6—L7F_A1_33.

Analysis of the purity, size and aggregation of the recombinant proteins is performed by size exclusion chromatography (SE-HPLC) and SDS-PAGE SE-HPLC (Shimadzu) is run on the column SUPERDEX200 (GE Healthcare). For SDS-PAGE proteins are diluted in sample buffer (0.08 M Tris-HCl at pH 8.8, 2% SDS, 10% glycerol, 0.01% bromophenol blue), boiled for five minutes in the presence of beta-mercaptoethanol (or DTT) and electrophoretically separated on Criterion XT 4-12% Bis-Tris glycine polyacrylamide gels (BioRad) (SDS-PAGE). The gels are stained in a solution of Coomassie blue (Instant blue, Sigma Aldrich). The excess stain is removed with water and the bands are visualized using the Imager 600 (Amersham). FIG. 4 shows SE-HPLC analysis of the purified recombinant F proteins. The exemplary yields of the recombinant F proteins are shown in Table 4.

TABLE 4

Production yield of the recombinant F proteins

| Protein | SEQ ID NO | UV quantification (mg/50 mL) | Yield (mg/L) |
|---|---|---|---|
| L7F_A1_31 | 7 | 1.44 | 28.8 |
| L7F_A1_33 | 8 | 1.30 | 26.0 |
| L7F_A1_23 | 5 | 1.07 | 21.4 |
| L7F_A1_4.2 | 9 | 0.76 | 15.2 |
| sF_A1_K_L7 | 6 | 0.85 | 17.0 |
| sF_A1_K-E294 | 51 | 0.70 | 14.0 |

Example 3: Conformation of the Recombinant hMPV F Proteins

Determination of a Conformation Profile by Sandwich ELISA

Medium binging plates (Greiner) are coated with the human IgG1 DS7 capture antibody (Williams et al., 2007) at 200 ng/well and incubated overnight at 4° C. The plates are saturated for 2 hours at 37° C. with PBS 0.05% Tween 20 and 5% dried-skimmed milk under agitation (saturation buffer). The liquid is removed from the wells and plates are incubated for 1 hour at 37° C. with 2.5 ng/well of the purified proteins of interest diluted in the saturation buffer. After washing, 5-fold serial dilution in saturation buffer of mouse antibody MPE8 N113S (Corti et al., 2013) directed against pre-fusion hMPV F protein or mouse antibody MF1 (Melero, personal communications) directed against post-fusion hMPV F protein are incubated for 1 hour at 37° C. Then the immune complexes are detected by incubation for one hour at 37° C. with secondary α-Ig species-specific antibody conjugated with peroxidase HRP Goat Anti-Mouse IgG (Covalab #lab0252) followed by 50 μL of peroxidase substrate (TMB, Sigma). The colorimetric reaction is stopped by adding 3 N $H_2SO_4$ and the absorbance of each well is measured at 490 nm with a spectrophotometer (MultiSkan).

Figure 5:
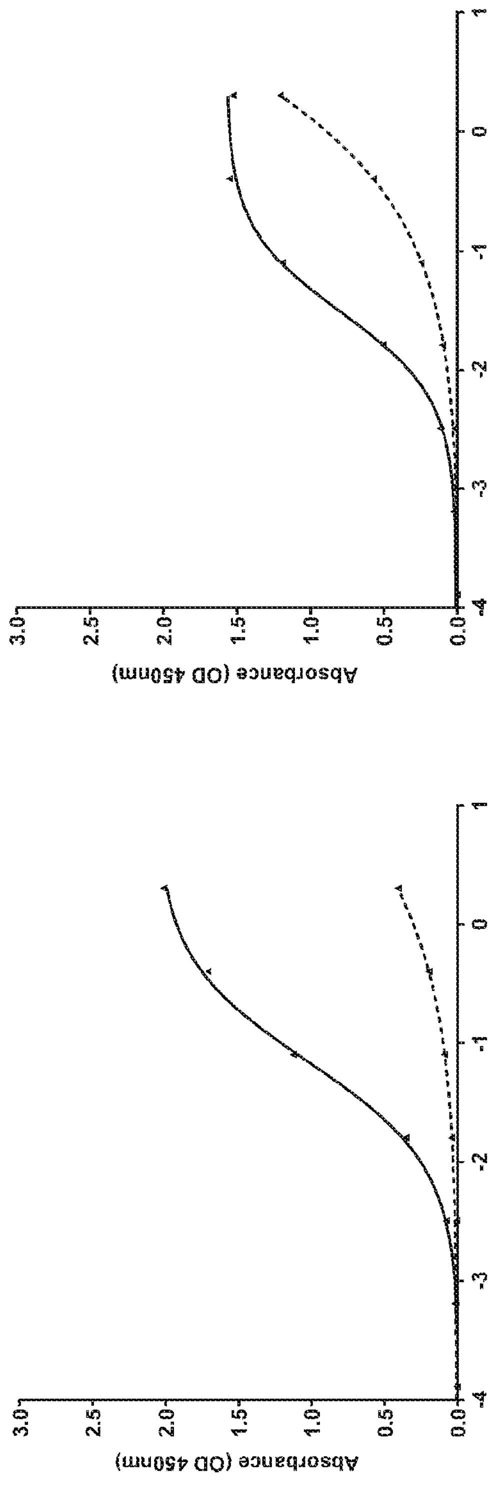
FIG. 5 shows ELISA data obtained with pre- or post-fusion specific antibodies for the recombinant hMPV F proteins: (A) sF_A1_K-E294; (B) sF_A1_K_L7; (C) L7F_A1_4.2; (D) L7F_A1_23; (E) L7F_A1_31; (F) L7F_A1_33; (G) L7F_A1_23.2. In all charts, except (G), the solid line indicates signals obtained by using different dilutions of the anti-pre-fusion antibody MPE8 N113S, and the dotted line indicates signals obtained by using different dilutions of the anti-post-fusion antibody MF1. In (G): the upper line indicates signals obtained with the anti-pre-fusion antibody MPE8 N113S, and the lower line indicates signals obtained with the anti-post-fusion antibody MF1.
Figure 5:
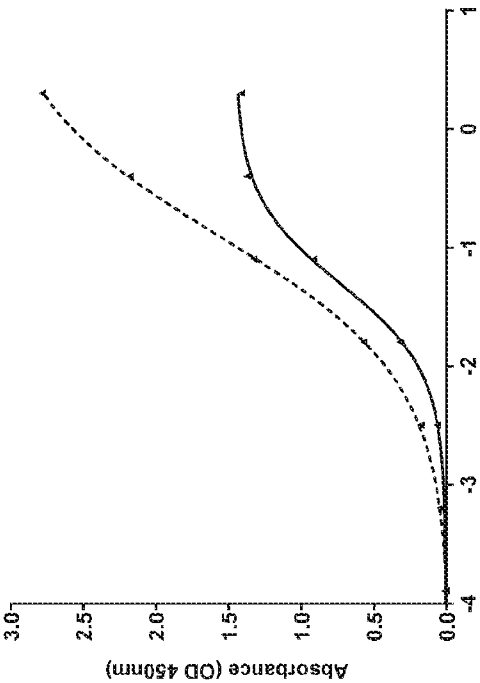
Figure 5:
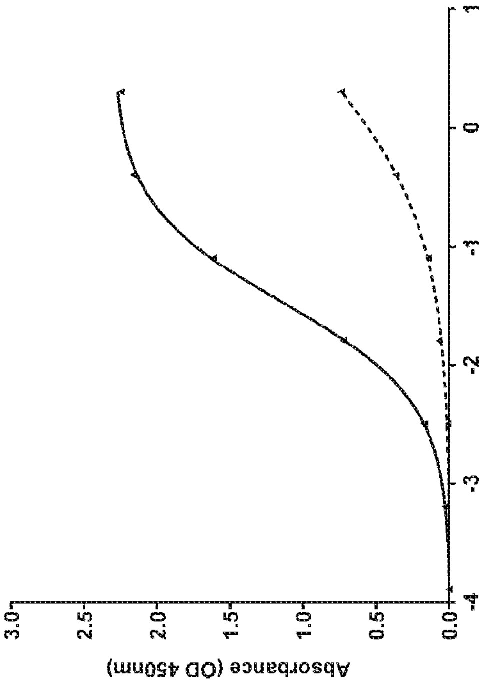
Figure 5:
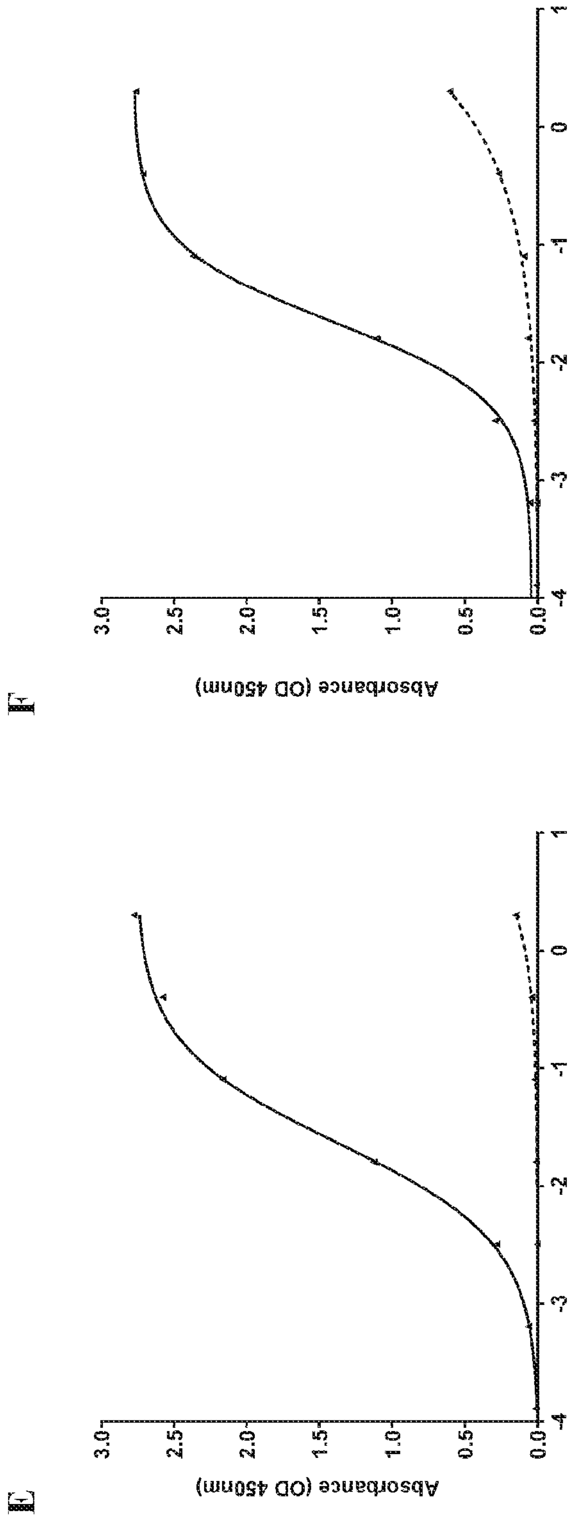
Figure 5:
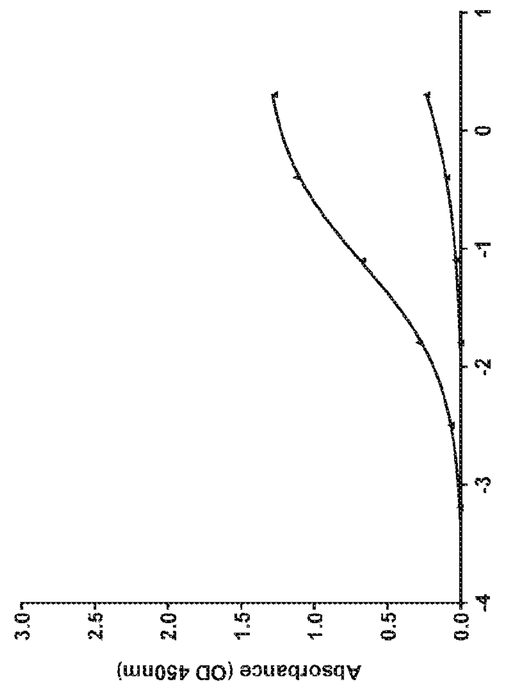

FIG. 5 shows the results of ELISA performed for the recombinant F proteins with the pre- or post-fusion specific antibodies. All tested candidates exhibit the abundance of the pre-fusion profile, except one candidate L7F_A1_4.2, which exists in both pre- and post-fusion conformations. The recombinant protein L7F_A1_23.3 differs from L7F_A1_23 only in one amino acid residue in the heterologous linker, i.e. it comprises the valine at position 5 of the linker (CGAGV), which corresponds to the valine reside at position 118 of SEQ ID NO: 1.

Example 4: Immunogenicity Studying

Immunogenicity in Mice

Groups of five to ten BALB/c mice are immunized three times with three weeks interval (e.g. days 0, 14 or 21 and 28 or 42) subcutaneously with the recombinant F proteins (used in different experiments in amounts from 0.06 μg to 6.0 μg per mouse) with or without different adjuvant, particularly alum, alum+MPL, IC31®, Addavax™ (InvivoGen). Sera are collected by retro-orbital bleeding. One to four weeks after the last vaccination, blood is drawn and sera are prepared. Evaluation of the $Th_1/Th_2$ type immune response is performed by determining $IgG_1/IgG_{2a}$ subtypes in the sera by indirect ELISA as described below.

Subclass IgG ELISA

The recombinant F protein is diluted in carbonate/bicarbonate buffer at pH 9.6, and 50 ng of the protein per well is added to 96-well high binding plate (50 μL/well, Greiner). The plates are incubated overnight at 4° C. The wells are saturated for 30 minutes at room temperature with 150 μL of PBS 0.05% Tween 20 and 5% dried skimmed milk (saturation buffer). The liquid is removed from the wells and plates are incubated for 1 hour at room temperature with 50 μL/well of the sera of immunized mice at different dilutions (5-fold serial dilution) in saturation buffer. After washing 3 times with PBS 0.05% Tween 20, the immune complexes are detected by incubation for one hour at room temperature with 50 μl of secondary anti-$IgG_1$ or $IgG_{2a}$ mouse-specific antibody conjugated with peroxidase followed by 50 μL of peroxidase substrate (TMB, Sigma). The colorimetric reaction is stopped by adding orthophosphoric acid and the absorbance of each well is measured at 490 nm with a spectrophotometer (MultiSkan).

Figure 6:
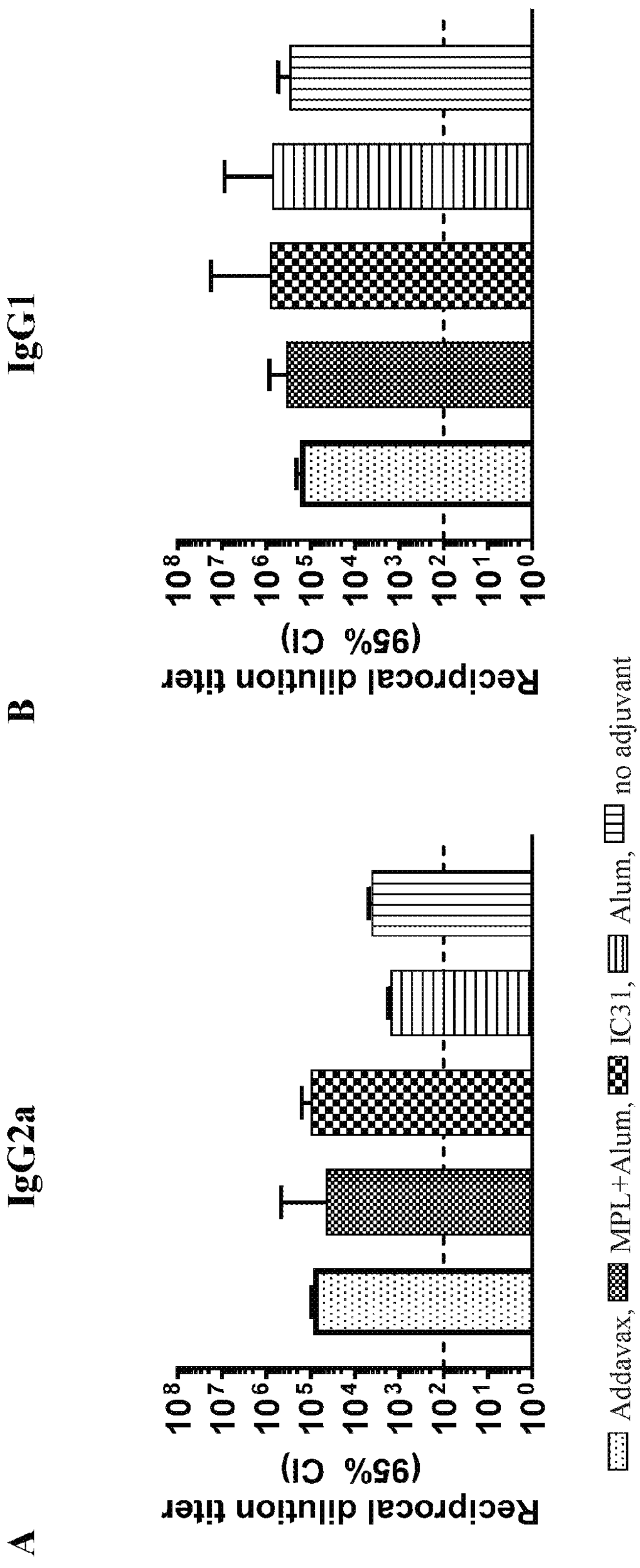
FIG. 6 shows serum IgG titers in mice immunized with the recombinant F proteins in combination with different adjuvants. (A and B) mice immunized with 2 μg of sF_A1_K_L7; (C and D) mice immunized with 2 μg of sF_A1_MFur.
Figure 6:
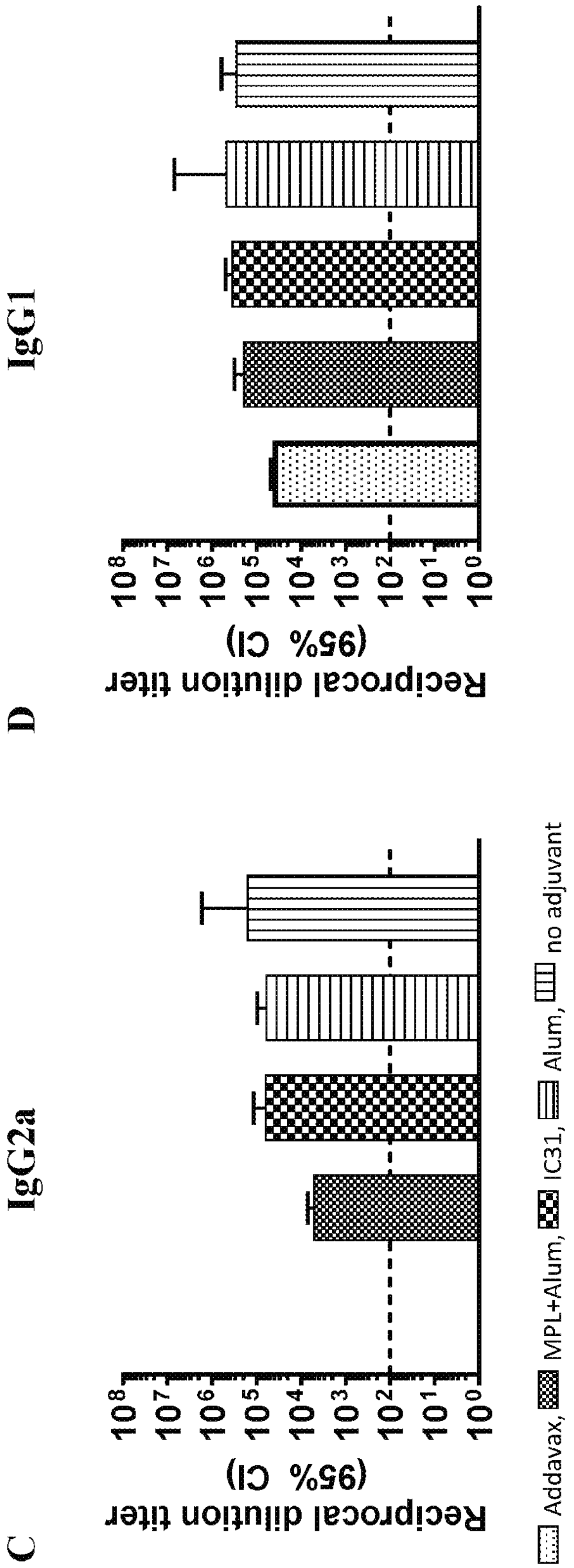

FIG. 6 shows results of IgG ELISA obtained by testing sera from mice immunized with 2 μg per mouse of the recombinant protein sF_A1_K_L7 (SEQ ID NO: 6) or sF_A1_MFur (SEQ ID NO: 53) administered in combination with different adjuvants. Induction of high $IgG_1/IgG_{2a}$ titers is demonstrated for both F proteins disregarding which adjuvant has been used.

Figure 7:
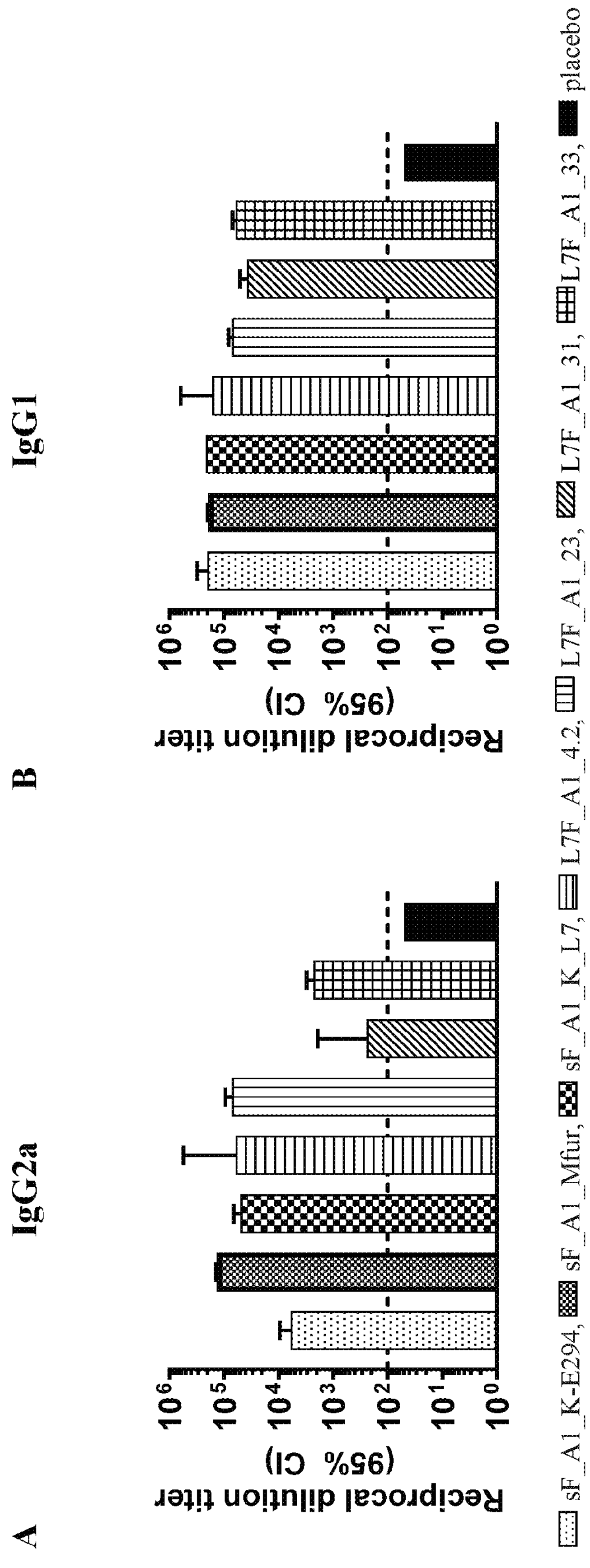
FIG. 7 shows serum IgG reciprocal dilution titers in mice immunized with the recombinant F proteins adjuvanted with Addavax™. The dotted line represent the limit of detection. (A) $IgG_{2a}$ reciprocal titer dilutions. (B) IgG1 reciprocal titer dilutions.

FIG. 7 shows results of $IgG_1$ and $IgG_{2a}$ titers which were measured in mice immunized with one of the recombinant F protein (2 μg) adjuvanted with Addavax™ mixed 1:1 (v/v).

Figure 8:
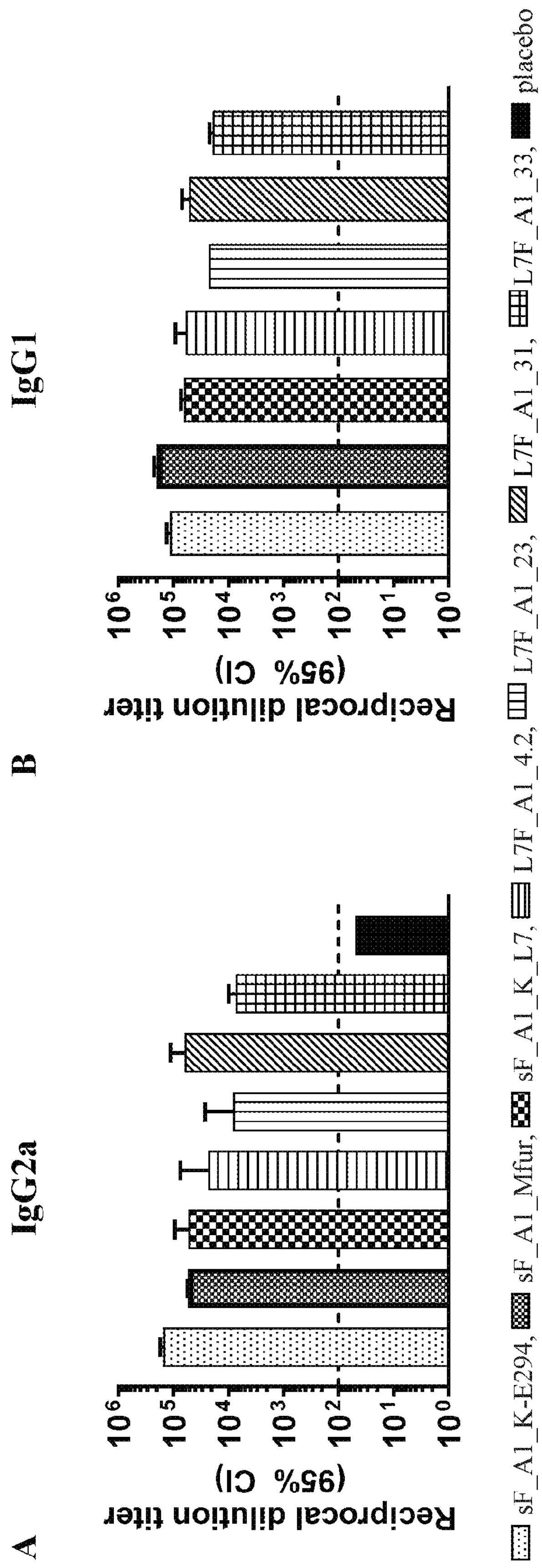
FIG. 8 shows serum IgG reciprocal dilution titers in mice immunized with the recombinant F proteins adjuvanted with IC31®. The dotted line represent the limit of detection. (A) $IgG_{2a}$ reciprocal titer dilutions. (B) IgG1 reciprocal titer dilutions.

FIG. 8 also shows serum $IgG_1$ and $IgG_{2a}$ titers measured in mice immunized with one of the recombinant F protein (2 μg) adjuvanted with IC31®. Despite some variabilities, the data clearly indicate that all vaccine candidates are highly immunogenic and able to elicit $IgG_1/IgG_{2a}$ antibodies.

Example 5: Induction of Neutralizing Antibodies

Neutralization Assay

Briefly, the plaque reduction neutralization test (PRNT) is used to determine a serum/antibody titer of an immunized subject required to reduce the number of hMPV virus plaques by 50% (PRNT50) as compared to a control serum/antibody. The PRNT50 is carried out by using monolayers of cells that can be infected with hMPV. Sera from subjects are diluted and incubated with the live hMPV virus. Plaques formed on cell monolayers are counted and compared to the number of plaques formed by the virus in the absence of serum or a control antibody. A threshold of neutralizing antibodies of 1:10 dilution of serum in a PRNT50 is generally accepted as evidence of protection (Hombach et. al. 2005. *Vaccine* 23: 5205-5211).

PRNT Protocol

The 24-well plate is seeded with LLC-MK2 cells, $1.2\times10^5$ cells per well, under 1 mL of EMEM (Lonza), 2 mM L-Gln (Ozyme), 5% FBS and 1% NeAA (Ozyme) buffer and incubated 24 hours at 37° C. and 5% $CO_2$. The hMPV A1 virus (Valneva MVB 1611-009 bank) is diluted to 50 pfu/62.5 μL (per well) or 800 pfu/mL. Equal volumes of the virus and serum dilution (2×62.5 μL) are combined and incubated at 37° C. with 5% $CO_2$ for approximately 1 hour. After plate washing with PBS, 125 μL of the virus/serum mixture is added to each well and the plate is incubated for 2 hours at 37° C. under shaking (100 rpm). Then, 225 μL/well of the overlay solution (EMEM, 2 mM Gln, 0.75% methylcellulose) is added and the plate is incubated 5 days at 37° C. with 5% $CO_2$. For cell fixation, 225 μL/well of 4% PFA/PBS is added, incubated for 10 minute at room temperature and subsequently washed 3 times with PBS. For cell permeabilization, 0.5 ml of PBS, 0.5% Tween, 0.1% BSA is added to each well and incubated 30 minutes at 4° C. Primary antibody (human DS7-PRO-2016-003) (0.91 μg/mL) is diluted in PBS to 5 μL/mL final concentration and 150 μL of primary antibody dilution is added per well and incubated 45 minutes at 37° C. under shaking. After removing the primary antibody and washing the plate 3 times with the blocking buffer, 150 μL/well of the diluted secondary antibody—anti-human-HRP (UP783493)—are added and the plate is incubate for another 45 minutes at 37° C. under shaking. Then, the secondary antibody are removed and the plate is washed 3 times with the blocking buffer. For staining, 150 μL of DAB 1× substrate per well is added. After 1 hour incubation at room temperature cells are counted manually under the microscope.

Figure 9:
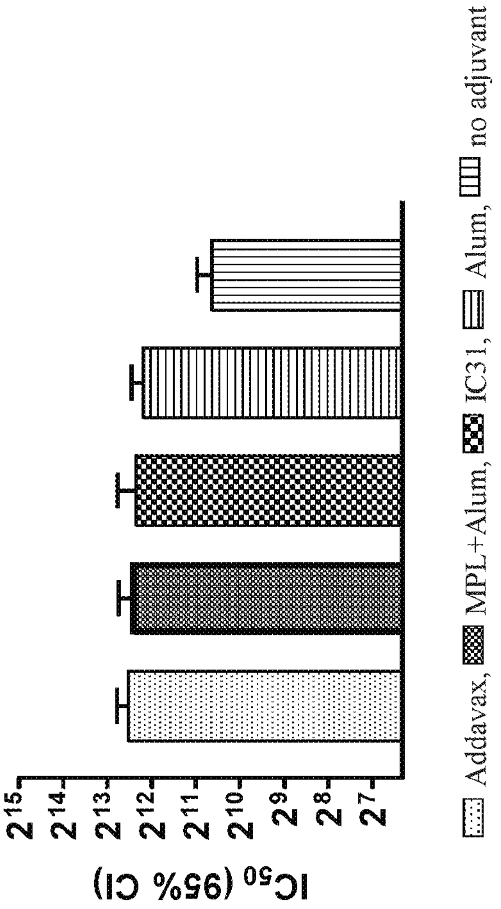
FIG. 9 shows neutralizing antibody titers ($IC_{50}$, reciprocal dilution titers) in mouse sera raised against the sF_A1_K_L7 protein in combination with different adjuvants.

FIG. 9 shows results of the neutralization assay obtained with sera harvested at day 57 from mice immunized with the recombinant protein sF_A1_K_L7 (2 μg) in the context of different adjuvants. Generally, the neutralizing antibodies against the tested F protein are present in the mouse sera disregard the used adjuvant.

Figure 10:
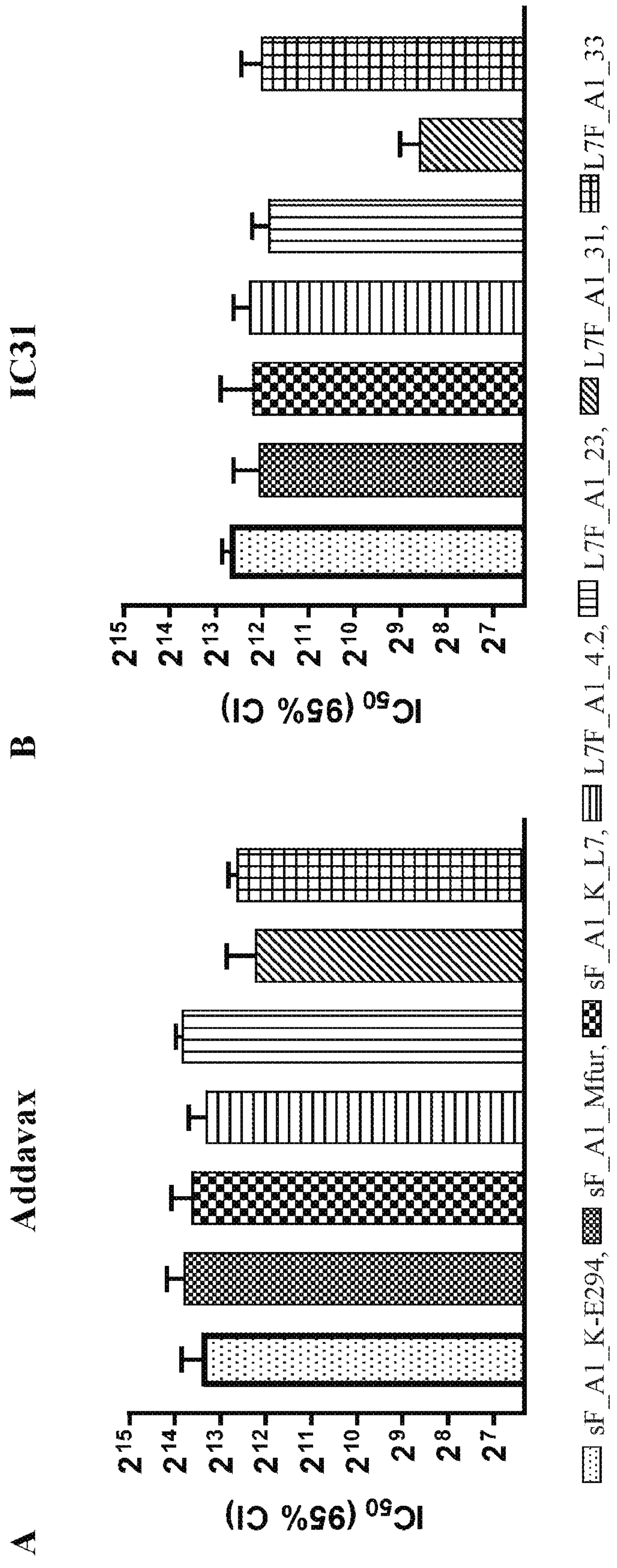
FIG. 10 shows neutralizing antibody titers ($IC_{50}$, reciprocal dilution titers) in mouse sera raised against the recombinant F proteins adjuvanted with (A) Addavax™ or (B) IC31®.

In the experiments where all protein candidates were tested alongside, the $IC_{50}$ values were highest for the L7F_A1_23 candidate adjuvanted with Addavax™ and for the L7F_A1_23 candidate adjuvanted with IC31® (see FIG. 10 and Table 5). The lowest $IC_{50}$ values were calculated for the L7F_A1_31 candidate independently from the used adjuvant.

TABLE 5

| Protein | SEQ ID NO | $IC_{50}$ - Addavax | $IC_{50}$ - IC31 |
|---|---|---|---|
| sF_A1_K-E294 | 51 | 9423 | 6536 |
| sF_A1_K_L7 | 6 | 11832 | 5250 |
| L7F_A1_4.2 | 9 | 9344 | 4829 |
| L7F_A1_23 | 5 | 14592 | 3891 |
| L7F_A1_31 | 7 | 4896 | 409 |
| L7F_A1_33 | 8 | 6236 | 6320 |

Figure 11:
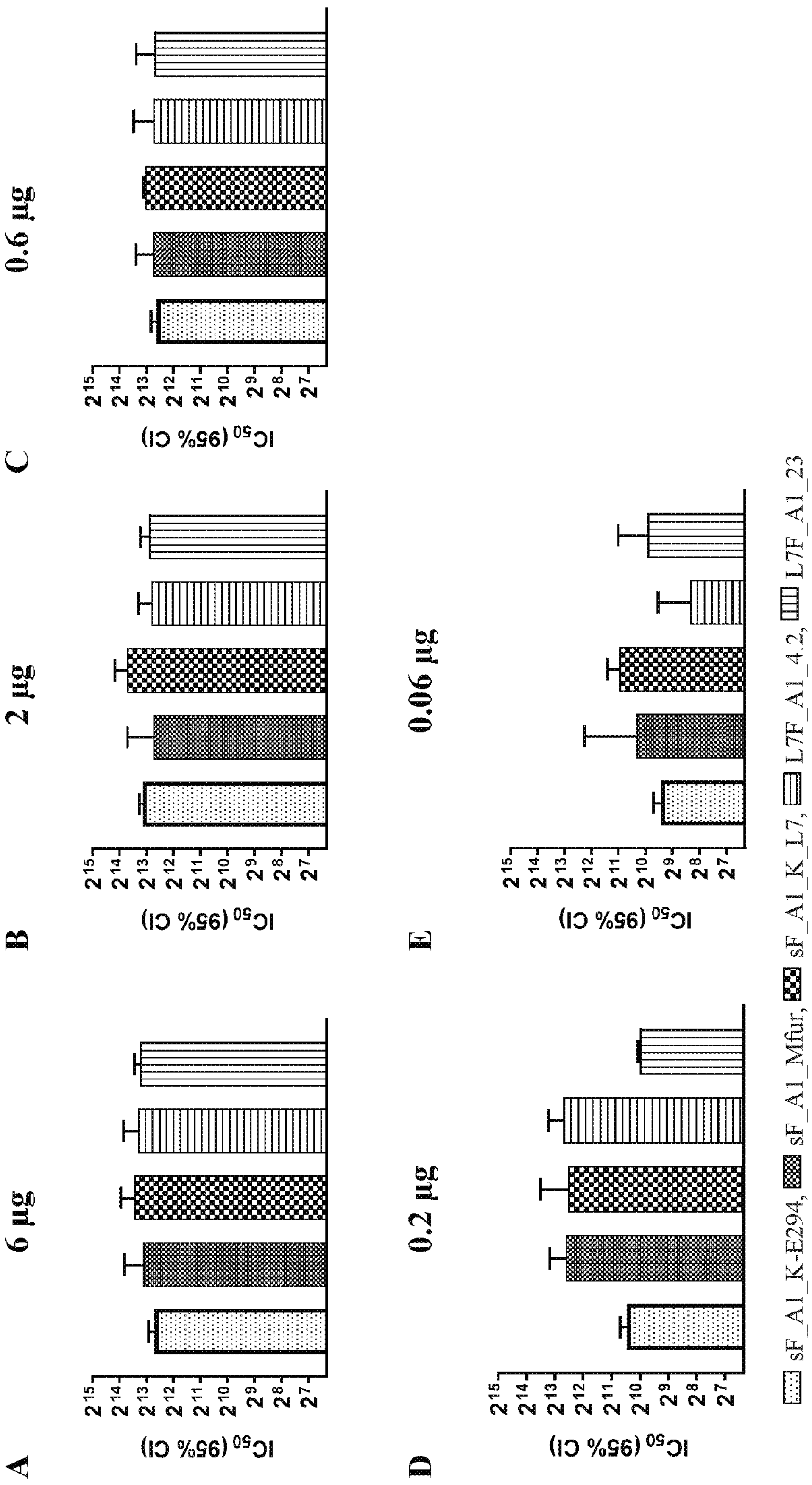
FIG. 11 shows neutralizing antibody titers ($IC_{50}$, reciprocal dilution titers) in mouse sera raised against different doses of the recombinant F proteins. (A) mice immunized with 6 μg F protein, (B) mice immunized with 2 μg F protein, (C) mice immunized with 0.6 μg F protein, (D) mice immunized with 0.2 μg F protein and (E) mice immunized with 0.06 μg F protein.

FIG. 11 demonstrates a dose-response study performed to evaluate the immunogenicity of the recombinant F proteins when inoculated into mice in combination with Addavax™. In contrast to the placebo group (data not shown), neutralizing antibodies are detected in the sera of mice immunized with 0.06 μg to 6.0 μg of the recombinant F protein. No significant difference of $IC_{50}$ was observed among the constructs.

Example 6: Protection in Mice

Virus Plaque (Foci) Immunostaining

The assay for hMPV foci quantification was developed based on the methods published in Williams et al., 2005. *J Virology* 79(17):10944-51; Williams et al., 2007. *J Virology* 81(15):8315-24; and Cox et al., 2012. J. Virology 86(22): 12148-60. Briefly, confluent cultures of Vero cells or LLC-MK2 cells in 24-well plates are infected with 50 μL/well of the hMPV virus pre-incubated for 30 minutes at room temperature in the presence or absence of mouse sera diluted in the medium. The mouse $IgG_{2a}$ DS7 monoclonal antibody is used for detection of hMPV. After a period of two hours of virus adsorption at 37° C., 1.5% methylcellulose overlay containing EMEM medium supplemented with 2 mM L-Gln and 20 to 50 μg/mL of trypsin is added. At day 6 post-infection, the supernatant is removed and the cells are washed twice with PBS. Cell monolayers are fixed and stained with the human $IgG_1$ DS7 antibody. Foci are counted and 50% plaque reduction titers are calculated taking into account relevant negative and positive controls. Cell images are captured with a Zeiss microscope using a 2.5× or 10× objective. Results of the immunostaining are expressed as focus forming units per milliliter, or FFU/mL.

Challenge Protocol

The hMPV A1 and A2 isolates, grown on LLC-MK2 cells, are used in animal challenge experiments. BALB/c mice are immunized three times in two weeks interval with adjuvanted recombinant F protein, as described previously, and on day 42 post-immunization they are challenged intranasally with around $1\times10^6$ pfu of the hMPV. Four to five days later, the animals are sacrificed and individual serum samples are taken and frozen. Lung tissue samples are harvested, weighed and homogenized for determination of viral titer. Viral load in lung tissues is determined by virus foci immunostaining, as described above. Alternatively or additionally, RT-qPCR is used to determine viral load in the harvested tissues.

Figure 12:
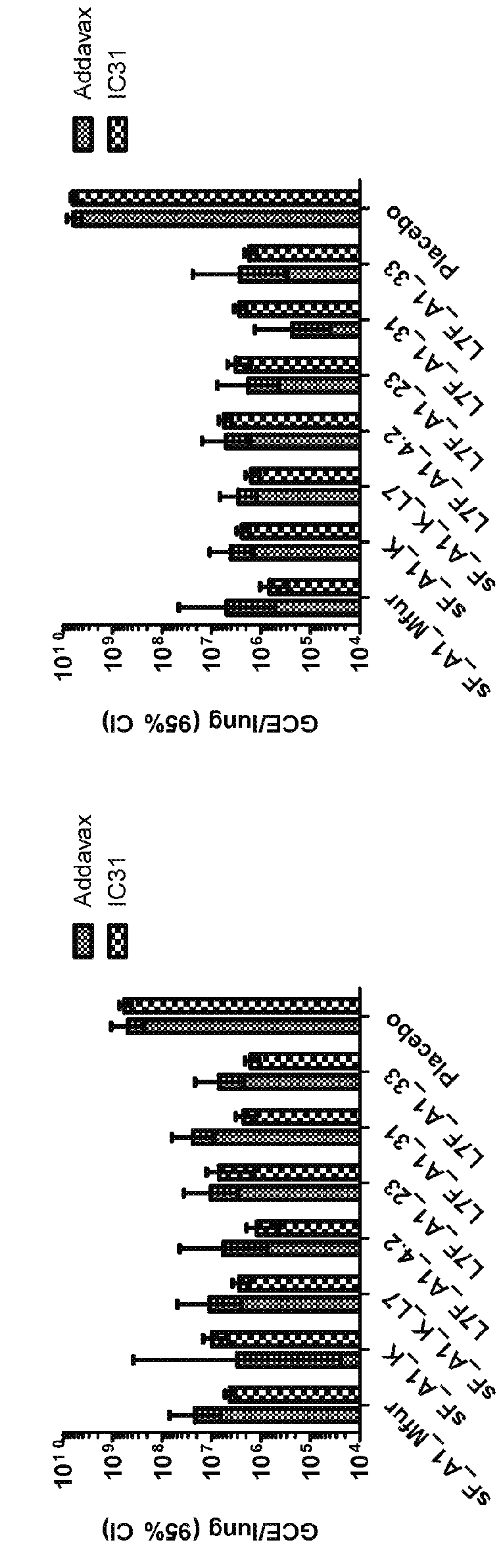
FIG. 12 shows viral RNA load in lungs of mice immunized with 2 μg of the recombinant F proteins adjuvanted with Addavax and subsequently challenged with the wild type hMPV (measured by RT-qPCR). A and B represent two independent experiments.
Figure 13:
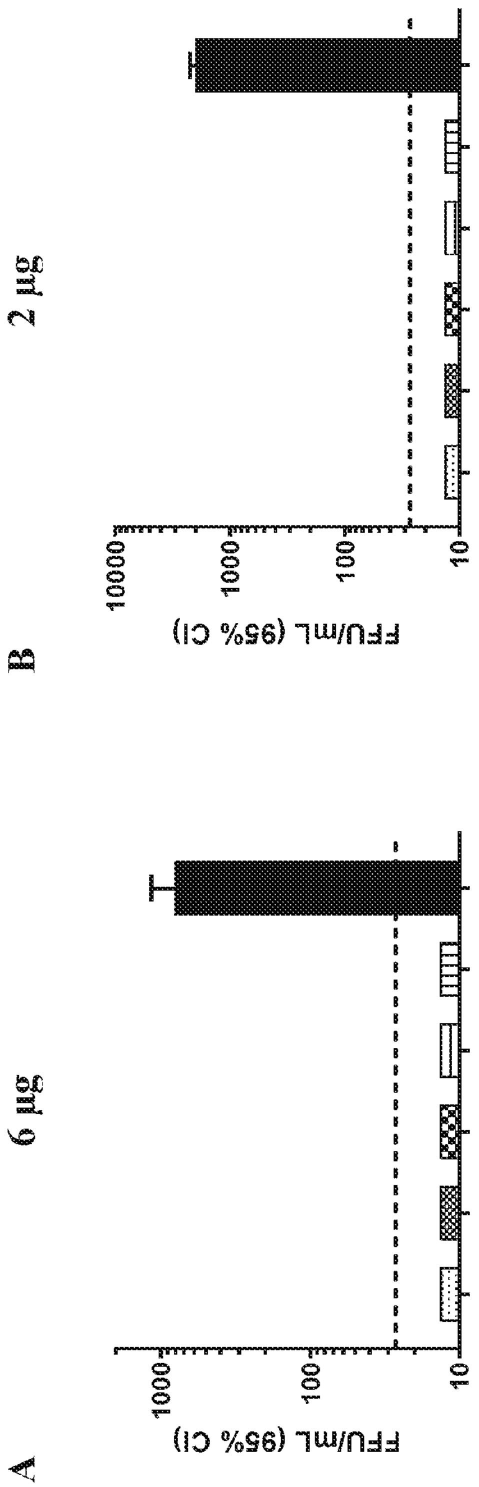
FIG. 13 shows protection in mice after immunization with the recombinant F proteins adjuvanted with Addavax™ and subsequent challenge with the wild type hMPV (lung colonization assay). (A) mice immunized with 6 μg F protein, (B) mice immunized with 2 μg F protein, (C) mice immunized with 0.6 μg F protein, (D) mice immunized with 0.2 μg F protein, and (E) mice immunized with 0.06 μg F protein.
Figure 13:
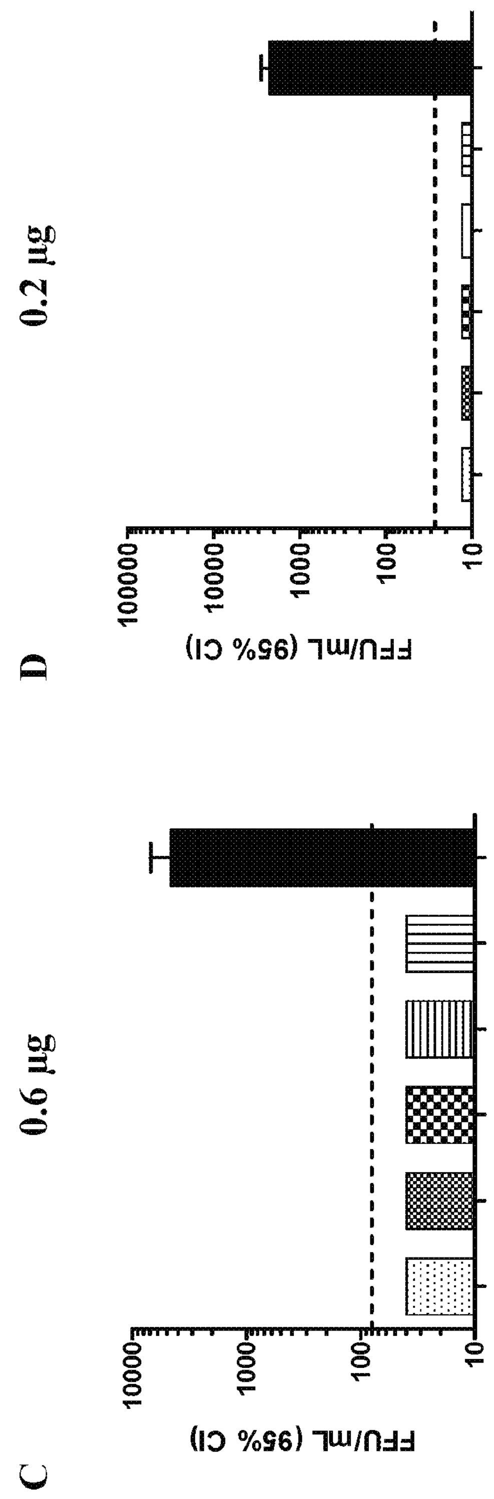
Figure 13:
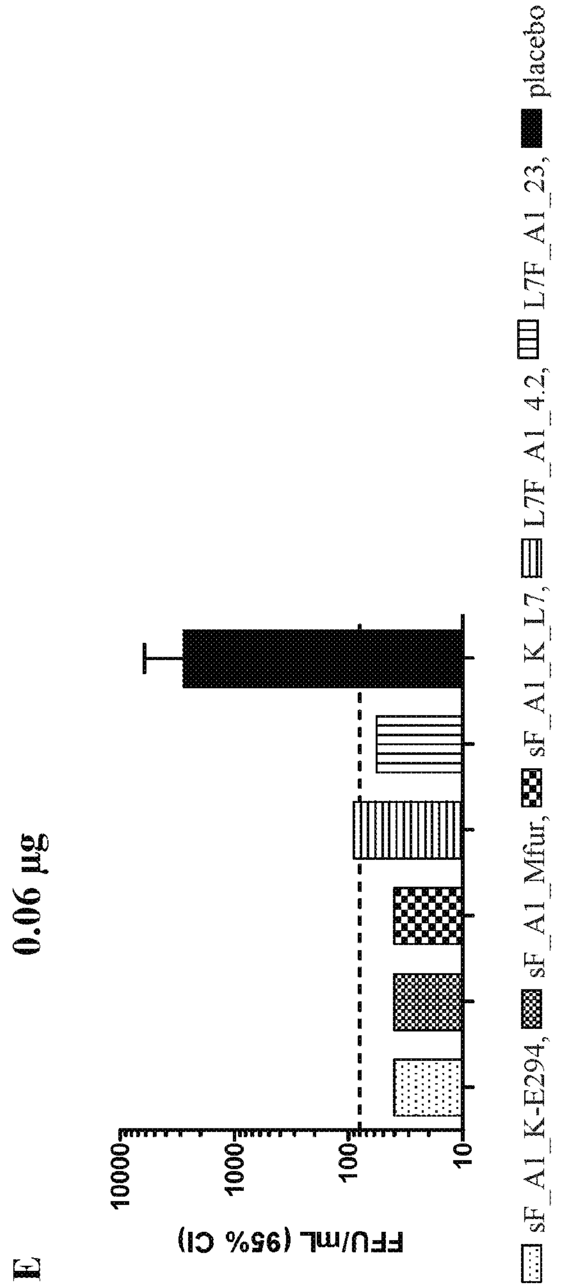

FIG. 12 demonstrates viral RNA load (GCE) in lungs of mice immunized with the adjuvanted recombinant F protein after the challenge with the wild type hMPV performed by RT-qPCR. The highest hMPV RNA load is observed in the placebo groups, while a strong reduction in the viral load is seen in lungs of the immunized mice demonstrating protection by the vaccine candidates. The protection effect is even more evident when virus plaque (foci) immunostaining is used. A strong reduction (up to 4 logs) of the viral load, calculated in FFU/mL, is observed in mice immunized with different protein doses (from 0.06 to 6.0 μg per mouse) as compared to the placebo group for all tested hMPV F protein candidates, as shown in FIG. 13.

It will be apparent that the precise details of the methods or compositions described may be varied or modified without departing from the spirit of the described embodiments. We claim all such modifications and variations that fall within the scope and spirit of the claims below. All publications described in the present application are incorporated herein by reference.

SEQUENCES

Native hMPV F protein sequence of strain NL/1/00, serotype genotype A1 (GenBank: AAK62968.2)

SEQ ID NO: 1

MSWKVVIIFSLLITPQHGLKESYLEESCSTITEGYLSVLRTGWYTNVFTLEVGDVENLTCADGPSLIK

TELDLTKSALRELRTVSADQLAREEQIENPRQSRFVLGAIALGVATAAAVTAGVAIAKTIRLESEVTA

IKNALKKTNEAVSTLGNGVRVLATAVRELKDFVSKNLTRAINKNKCDIADLKMAVSFSQFNRRFLNVV

RQFSDNAGITPAISLDLMTDAELARAVSNMPTSAGQIKLMLENRAMVRRKGFGFLIGVYGSSVIYMVQ

LPIFGVIDTPCWIVKAAPSCSGKKGNYACLLREDQGWYCQNAGSTVYYPNEKDCETRGDHVFCDTAAG

INVAEQSKECNINISTTNYPCKVSTGRHPISMVALSPLGALVACYKGVSCSIGSNRVGIIKQLNKGCS

YITNQDADTVTIDNTVYQLSKVEGEQHVIKGRPVSSSFDPVKFPEDQFNVALDQVFESIENSQALVDQ

SNRILSSAEKGNTGFIIVIILIAVLGSTMILVSVFIIIKKTKKPTGAPPELSGVTNNGFIPHN

Native hMPV F2 domain sequence of strain NL/1/00, serotype A1

SEQ ID NO: 2

LKESYLEESCSTITEGYLSVLRTGWYTNVFTLEVGDVENLTCADGPSLIKTELDLTKSALRELRTVSA

DQLAREEQIENPRQSR

Native hMPV F1 domain sequence of strain NL/1/00, serotype A1

SEQ ID NO: 3

FVLGAIALGVATAAAVTAGVAIAKTIRLESEVTAIKNALKKTNEAVSTLGNGVRVLATAVRELKDFVS

KNLTRAINKNKCDIADLKMAVSFSQFNRRFLNVVRQFSDNAGITPAISLDLMTDAELARAVSNMPTSA

GQIKLMLENRAMVRRKGFGFLIGVYGSSVIYMVQLPIFGVIDTPCWIVKAAPSCSGKKGNYACLLRED

QGWYCQNAGSTVYYPNEKDCETRGDHVFCDTAAGINVAEQSKECNINISTTNYPCKVSTGRHPISMVA

LSPLGALVACYKGVSCSIGSNRVGIIKQLNKGCSYITNQDADTVTIDNTVYQLSKVEGEQHVIKGRPV

SSSFDPVKFPEDQFNVALDQVFESIENSQALVDQSNRILSSAEKGNTGFIIVIILIAVLGSTMILVSV

FIIIKKTKKPTGAPPELSGVTNNGFIPHN

Heterologous peptide linker

SEQ ID NO: 4

CGAGA

L7F_A1_23 protein sequence

SEQ ID NO: 5

MSWKVVIIFSLLITPQHGLKESYLEESCSTITEGYLSVLRTGWYTNVFTLEVGDVENLTCADGPSLIK

TELDLTKSALRELRTVSADQLAREEQIEQPRQSGCGAGATAGVAIAKTIRLESEVTAIKNALKKTNEA

VSTLGNGVRVLATAVRELKDFVSKNLTRAINKNKCDIADLKMAVSFSQFNRRFLNVVRQFSDNAGITP

AISLDLMTDAELARAVSNMPTSAGQIKLMLENRAMVRRKGFGFLIGVYGSSVIYMVQLPIFGVIDTPC

WIVKAAPSCSEKKGNYACLLREDQGWYCQNAGSTVYYPNEKDCETRGDHVFCDTCAGINVAEQSKECN

-continued

INISTTNYPCKVSTGRHPISMVALSPLGALVACYKGVSCSIGSNRVGIIKQLNKGCSYITNQDADTVT

IDNTVYQLSKVEGEQHVIKGRPVSSSFDPVKFPEDQFNVALDQVFESIENSQALVDQSNRILSAGYIP

EAPRDGQAYVRKDGEWVLLSTFLGGLVPRGSHHHHHHSAWSHPQFEK sF_A1_K_L7 protein sequence

SEQ ID NO: 6

MSWKVVIIFSLLITPQHGLKESYLEESCSTITEGYLSVLRTGWYTNVFTLEVGDVENLTCADGPSLIK

TELDLTKSALRELRTVSADQLAREEQIEQPRQSGCGAGATAGVAIAKTIRLESEVTAIKNALKKTNEA

VSTLGNGVRVLAFAVRELKDFVSKNLTRALNKNKCDIADLKMAVSFSQFNRRFLNVVRQFSDNAGITP

AISLDLMTDAELARAVSNMPTSAGQIKLMLENRAMVRRKGFGFLIGVYGSSVIYMVQLPIFGVIDTPC

WIVKAAPSCSEKKGNYACLLREDQGWYCQNAGSTVYYPNEKDCETRGDHVFCDTCAGINVAEQSKECN

INISTTNYPCKVSTGRHPISMVALSPLGALVACYKGVSCSIGSNRVGIIKQLNKGCSYITNQDADTVT

IDNTVYQLSKVEGEQHVIKGRPVSSSFDPVKFPEDQFNVALDQVFESIENSQALVDQSNRILSSAESA

IGGYIPEAPRDGQAYVRKDGEWVLLSTFLGGLVPRGSHHHHHHSAWSHPQFEK

L7F_A1_31 protein sequence

SEQ ID NO: 7

MSWKVVIIFSLLITPQHGLKESYLEESCSTITEGYLSVLRTGWYTNVFMLEVGDVENLTCADGPSLLK

TELDLTKSALRNLRTVSADQLAREEQIEQPRQSGCGAGATAGVAIAKTIRLESEVTAIKNALKKTNEA

VSTLGNGVRVLATMVRELKDFVSKNLTRAINKNKCDIADLKMAVSFSQFNRRFLNVVRQFSDNAGITP

AISLDLMTDAELARAVSNMPTSAGQIKLMLENRAMVRRKGFGILIGVYGSSVIYMVQLPIFGVIDTPC

WIVKAAPSCSEKKGNYACLLREDQGWYCQNAGSTVYYPNEKDCETRGDHVFCDTCAGINVAEQSKECN

INISTTNYPCKVSTGRHPISMVALSPLGALVACYKGVSCSIGSNRVGIIKQLNKGCSYITNQDADTVT

IDNTVYQLSKVEGEQHVIKGRPVSSSFDPVKFPEDQFNVALDQVFESIENSQALVDQSNRILSAGYIP

EAPRDGQAYVRKDGEWVLLSTFLGGLVPRGSHHHHHHSAWSHPQFEK

L7F_A1_33 protein sequence

SEQ ID NO: 8

MSWKVVIIFSLLITPQHGLKESYLEESCSTITEGYLSVLRTGWYTNVFMLCVGDVENLTCADGPSLLK

TELDLTKSALRELRTVSADQLAREEQIEQPRQSGCGAGATAGVAIAKTIRLESEVTAIKNALKKTNEA

VSTLGNGVRVLATMVRELCDFVSKNLTRAINKNKCDIADLKMAVSFSQFNRRFLNVVRQFSDNAGITP

AISLDLMTDAELARAVSNMPTSAGQIKLMLENRAMVRRKGFGFLIGVYGSDVIYMVQLPIFGVIDTPC

WIVKAAPSCSEKKGNYACLLREDQGWYCQNAGSTVYYPNEKDCETRGDHVFCDTCAGINVAEQSKECN

INISTTNYPCKVSTGRHPISMVALSPLGALVACYKGVSCSIGSNRVGIIKQLNKGCSYITNQDADTVT

IDNTVYQLSKVEGEQHVIKGRPVSSSFDPVKFPEDQFNVALDQVFESIENSQALVDQSNRCCSAGYIP

EAPRDGQAYVRKDGEWVLLSTFLGGLVPRGSHHHHHHSAWSHPQFEK

L7F_A1_4.2 protein sequence

SEQ ID NO: 9

MSWKVVIIFSLLITPQHGLKESYLEESCSTITEGYLSVLRTGWYTNVFMLEVGDVENLTCADGPSLIK

TELDLTKSALRELRTVSADQLAREEQIEQPRQSGCGAGATAGVAIAKTIRLESEVTAWKNALKKTNEV

VSTLGNGVRVLVTMVRELKDFVSKNLTRALNKNKCDIADLKMAVSFSQFNRRFLNVVRQFSDNAGITP

AISLDLMTDAELARAVSNMPTSAGQIKLMLENRAMVRRKGFGFLIGVYGSSVIYMVQLPIFGVIDTPC

WIVKAAPSCSEKKGNYACLLREDQGWYCQNAGSTVYYPNEKDCETRGDHVFCDTCAGINVAEQSKECN

INISTTNYPCKVSTGRHPISMVALSPLGALVACYKGVSCSIGSNRVGIIKQLNKGCSYITNQDADTVT

IDNTVYQLSKVEGEQHVIKGRPVSSSFDPVKFPEDQFNVALDQVFESIENSQALVDQSNRILSSAESA

IGGYIPEAPRDGQAYVRKDGEWVLLSTFLGGLVPRGSHHHHHHSAWSHPQFEK

Trimerization helper domain (foldon) from fibritin of T4 bacteriophage

SEQ ID NO: 10

-continued

GYIPEAPRDGQAYVRKDGEWVLLSTFL

His-tag sequence with leading GS as linker

SEQ ID NO: 11

GSHHHHHH

Streptavidin-tag sequence

SEQ ID NO: 12

SAWSHPQFEK

Native hMPV F protein sequence of strain NL/17/00, serotype A2 (GenBank: AY304360.1)

SEQ ID NO: 13

MSWKVVIIFSLLITPQHGLKESYLEESCSTITEGYLSVLRTGWYTNVFTLEVGDVENLTCSDGPS

LIKTELDLTKSALRELKTVSADQLAREEQIENPRQSRFVLGAIALGVATAAAVTAGVAIAKTIRL

ESEVTAIKNALKTTNEAVSTLGNGVRVLATAVRELKDFVSKNLTRAINKNKCDIDDLKMAVSFSQ

FNRRFLNVVRQFSDNAGITPAISLDLMTDAELARAVSNMPTSAGQIKLMLENRAMVRRKGFGILI

GVYGSSVIYTVQLPIFGVIDTPCWIVKAAPSCSEKKGNYACLLREDQGWYCQNAGSTVYYPNEKD

CETRGDHVFCDTAAGINVAEQSKECNINISTTNYPCKVSTGRHPISMVALSPLGALVACYKGVSC

SIGSNRVGIIKQLNKGCSYITNQDADTVTIDNTVYQLSKVEGEQHVIKGRPVSSSFDPIKFPEDQ

FNVALDQVFENIENSQALVDQSNRILSSAEKGNTGFIIVIILIAVLGSSMILVSIFIIIKKTKKP

TGAPPELSGVTNNGFIPHS

Native hMPV F protein sequence of strain CAN97-83, serotype A2 (Uniprot Q6WB98)

SEQ ID NO: 14

MSWKVVIIFSLLITPQHGLKESYLEESCSTITEGYLSVLRTGWYTNVFTLEVGDVENLTCSDGPS

LIKTELDLTKSALRELKTVSADQLAREEQIENPRQSRFVLGAIALGVATAAAVTAGVAIAKTIRL

ESEVTAIKNALKTTNEAVSTLGNGVRVLATAVRELKDFVSKNLTRAINKNKCDIDDLKMAVSFSQ

FNRRFLNVVRQFSDNAGITPAISLDLMTDAELARAVSNMPTSAGQIKLMLENRAMVRRKGFGILI

GVYGSSVIYMVQLPIFGVIDTPCWIVKAAPSCSGKKGNYACLLREDQGWYCQNAGSTVYYPNEKD

CETRGDHVFCDTAAGINVAEQSKECNINISTTNYPCKVSTGRHPISMVALSPLGALVACYKGVSC

SIGSNRVGIIKQLNKGCSYITNQDADTVTIDNTVYQLSKVEGEQHVIKGRPVSSSFDPIKFPEDQ

FNVALDQVFENIENSQALVDQSNRILSSAEKGNTGFIIVIILIAVLGSSMILVSIFIIIKKTKKP

TGAPPELSGVTNNGFIPHS

Native hMPV F protein sequence of strain NCL174, serotype A2 (Uniprot G0ZRI7)

SEQ ID NO: 15

MSWKVVIIFSLLITPQHSLKESYLEESCSTITEGYLSVLRTGWYTNVFTLEVGDVENLTCADGPS

LIKTELDLTKSALRELKPVSADQLAREEQIENPRQSRFVLGAIALGVATAAAVTAGVAIAKTIRL

ESEVTAIKNALKKTNEAVSTLGNGVRVLATAVRELKDFVSKNLTRAINKNKCDIDDLKMAVSFSQ

FNRRFLNVVRQFSDNAGITPAISLDLMTDAELARAVSNMPTAAGQIKLMLENRAMVRRKGFGILI

GVYGSSVIYMVQLPIFGVIDTPCWIVKAAPSCSEKKGNYACLLREDQGWYCQNAGSTVYYPNEKD

CETRGDHVFCDTAAGINVAEQSKECNINISTTNYPCKVSTGRHPISMVALSPLGALVACYKGVSC

SIGSNRVGIIKQLNKGCSYITNQDADTVTIDNTVYQLSKVEGEQHVIKGRPVSSSFDPVKFPEDQ

FNVALDQVFENIENSQALVDQSNRILSSAEKGNTGFIIVIILIAVLGSSMILVSVFIIIKKTRKP

TGAPPELSGVTNNGFIPHS

Native hMPV F protein sequence of strain NL/1/99 serotype B1 (GenBank: AY304361.1)

SEQ ID NO: 16

MSWKVMIIISLLITPQHGLKESYLEESCSTITEGYLSVLRTGWYTNVFTLEVGDVENLTCTDGPS

LIKTELDLTKSALRELKTVSADQLAREEQIENPRQSRFVLGAIALGVATAAAVTAGIAIAKTIRL

ESEVNAIKGALKQTNEAVSTLGNGVRVLATAVRELKEFVSKNLTSAINRNKCDIADLKMAVSFSQ

-continued

FNRRFLNVVRQFSDNAGITPAISLDLMTDAELARAVSYMPTSAGQIKLMLENRAMVRRKGFGILI

GVYGSSVIYMVQLPIFGVIDTPCWIIKAAPSCSEKNGNYACLLREDQGWYCKNAGSTVYYPNEKD

CETRGDHVFCDTAAGINVAEQSRECNINISTTNYPCKVSTGRHPISMVALSPLGALVACYKGVSC

SIGSNWVGIIKQLPKGCSYITNQDADTVTIDNTVYQLSKVEGEQHVIKGRPVSSSFDPIKFPEDQ

FNVALDQVFESIENSQALVDQSNKILNSAEKGNTGFIIVVILVAVLGLTMISVSIIIIIKKTRKP

TGAPPELNGVTNGGFIPHS

Native hMPV F protein sequence of strain NDL00-1, serotype B1
(GenBank: AAK62968.2)

SEQ ID NO: 17

MSWKVVIIFSLLITPQHGLKESYLEESCSTITEGYLSVLRTGWYTNVFTLEVGDVENLTCADGPS

LIKTELDLTKSALRELRTVSADQLAREEQIENPRQSRFVLGAIALGVATAAAVTAGVAIAKTIRL

ESEVTAIKNALKKTNEAVSTLGNGVRVLATAVRELKDFVSKNLTRAINKNKCDIADLKMAVSFSQ

FNRRFLNVVRQFSDNAGITPAISLDLMTDAELARAVSNMPTSAGQIKLMLENRAMVRRKGFGFLI

GVYGSSVIYMVQLPIFGVIDTPCWIVKAAPSCSGKKGNYACLLREDQGWYCQNAGSTVYYPNEKD

CETRGDHVFCDTAAGINVAEQSKECNINISTTNYPCKVSTGRHPISMVALSPLGALVACYKGVSC

SIGSNRVGIIKQLNKGCSYITNQDADTVTIDNTVYQLSKVEGEQHVIKGRPVSSSFDPVKFPEDQ

FNVALDQVFESIENSQALVDQSNRILSSAEKGNTGFIIVIILIAVLGSTMILVSVFIIIKKTKKP

TGAPPELSGVTNNGFIPHN

Native hMPV F protein sequence of strain CAN98-75, serotype B2
(Uniprot: 6WBA7)

SEQ ID NO: 18

MSWKVMIIISLLITPQHGLKESYLEESCSTITEGYLSVLRTGWYINVFTLEVGDVENLTCTDGPS

LIKTELDLTKSALRELKTVSADQLAREEQIENPRQSRFVLGAIALGVATAAAVTAGIAIAKTIRL

ESEVNAIKGALKTTNEAVSTLGNGVRVLATAVRELKEFVSKNLTSAINKNKCDIADLKMAVSFSQ

FNRRFLNVVRQFSDNAGITPAISLDLMTDAELARAVSYMPTSAGQIKLMLENRAMVRRKGFGILI

GVYGSSVIYMVQLPIFGVIDTPCWIIKAAPSCSEKDGNYACLLREDQGWYCKNAGSTVYYPNKKD

CETRGDHVFCDTAAGINVAEQSRECNINISTTNYPCKVSTGRHPISMVALSPLGALVACYKGVSC

SIGSNRVGIIKQLPKGCSYITNQDADTVTIDNTVYQLSKVEGEQHVIKGRPVSSSFDPIKFPEDQ

FNVALDQVFESIENSQALVDQSNKILNSAEKGNTGFIIVIILIAVLGLTMISVSIIIIIKKTRKP

TGAPPELNGVTNGGFIPHS sF_A1_K_L7 coding nucleotide sequence, codon optimized

SEQ ID NO: 19

ATGTCTTGGAAGGTGGTCATCATCTTCTCCCTGCTGATCACCCCTCAGCACGGCCTGAAAGAGTCCTA

CCTGGAAGAGAGCTGCTCCACCATCACCGAGGGCTACCTGTCTGTGCTGAGAACCGGCTGGTACACCA

ACGTGTTCACCCTGGAAGTGGGCGACGTGGAAAACCTGACCTGTGCTGATGGCCCCAGCCTGATCAAG

ACCGAGCTGGACCTGACCAAGTCTGCCCTGAGAGAACTGAGGACCGTGTCTGCCGATCAGCTGGCCAG

AGAGGAACAGATCGAGCAGCCTAGACAGTCCGGATGTGGTGCTGGTGCTACAGCTGGCGTGGCCATTG

CCAAGACCATCCGGCTGGAATCTGAAGTGACCGCCATCAAGAACGCCCTGAAAAAGACCAACGAGGCC

GTGTCTACCCTCGGCAATGGCGTTAGAGTGCTGGCCTTTGCTGTGCGCGAGCTGAAGGACTTCGTGTC

CAAGAACCTGACCAGGGCTCTGAACAAGAACAAGTGTGATATCGCCGACCTGAAGATGGCCGTGTCCT

TTAGCCAGTTCAACCGGCGGTTCCTGAACGTCGTGCGGCAGTTCTCTGATAACGCCGGCATCACCCCT

GCCATCAGCCTGGATCTGATGACCGATGCCGAGCTGGCTAGAGCCGTGTCCAACATGCCTACCTCTGC

CGGCCAGATCAAGCTGATGCTGGAAAACAGAGCCATGGTCCGACGGAAAGGCTTCGGCTTTCTGATCG

GCGTGTACGGCTCCTCCGTGATCTACATGGTGCAGCTGCCTATCTTCGGCGTGATCGACACCCCTTGC

-continued

TGGATCGTGAAGGCCGCTCCTAGCTGCTCTGAGAAGAAGGGCAACTACGCCTGCCTGCTGAGAGAGGA

CCAAGGCTGGTACTGTCAGAACGCCGGCTCCACCGTGTACTACCCCAACGAGAAGGACTGCGAGACAA

GAGGCGACCACGTGTTCTGCGATACCTGCGCTGGCATCAATGTGGCCGAGCAGTCCAAAGAGTGCAAC

ATCAACATCTCCACCACCAACTATCCCTGCAAGGTGTCCACCGGCAGGCACCCTATTTCCATGGTGGC

TCTGTCTCCACTGGGCGCCCTGGTGGCTTGTTATAAGGGCGTGTCCTGCTCCATCGGCTCCAACAGAG

TGGGCATCATCAAGCAGCTGAACAAGGGCTGCAGCTACATCACCAACCAGGACGCCGATACCGTGACC

ATCGACAATACCGTGTATCAGCTGTCCAAGGTGGAAGGCGAGCAGCACGTGATCAAGGGCAGACCTGT

GTCCTCCAGCTTCGACCCCGTGAAGTTCCCTGAGGATCAGTTCAACGTGGCCCTGGACCAGGTGTTCG

AGTCCATCGAGAACTCTCAGGCTCTGGTGGACCAGTCCAACCGGATCCTGTCCTCTGCCGAGTCTGCT

ATCGGCGGCTATATCCCCGAGGCTCCTAGAGATGGCCAGGCCTATGTTCGGAAGGATGGCGAATGGGT

GCTGCTGTCTACCTTCCTCGGAGGCCTGGTGCCTAGAGGCTCTCACCACCATCATCACCACTCCGCTT

GGTCCCATCCACAGTTCGAGAAGTGA

L7F_A1_23 coding nucleotide sequence, codon optimized

SEQ ID NO: 20

ATGTCTTGGAAGGTGGTCATCATCTTCTCCCTGCTGATCACCCCTCAGCACGGCCTGAAAGAGTCCTA

CCTGGAAGAGAGCTGCTCCACCATCACCGAGGGCTACCTGTCTGTGCTGAGAACCGGCTGGTACACCA

ACGTGTTCACCCTGGAAGTGGGCGACGTGGAAAACCTGACCTGTGCTGATGGCCCCAGCCTGATCAAG

ACCGAGCTGGACCTGACCAAGTCTGCCCTGAGAGAACTGAGGACCGTGTCTGCCGATCAGCTGGCCAG

AGAGGAACAGATCGAGCAGCCTAGACAGTCCGGATGTGGTGCTGGTGCTACAGCTGGCGTGGCCATTG

CCAAGACCATCCGGCTGGAATCTGAAGTGACCGCCATCAAGAACGCCCTGAAAAAGACCAACGAGGCC

GTGTCTACCCTCGGCAATGGCGTTAGAGTGCTGGCCACAGCCGTGCGCGAGCTGAAGGATTTCGTGTC

CAAGAACCTGACCAGGGCCATCAACAAGAACAAGTGTGATATCGCCGACCTGAAGATGGCCGTGTCCT

TCAGCCAGTTCAACCGGCGGTTCCTGAATGTCGTGCGGCAGTTCTCTGACAACGCCGGCATCACCCCT

GCCATCAGCCTGGATCTGATGACCGATGCCGAGCTGGCTAGAGCCGTGTCCAACATGCCTACCTCTGC

CGGCCAGATCAAGCTGATGCTGGAAAACAGAGCCATGGTCCGACGGAAAGGCTTCGGCTTTCTGATCG

GCGTGTACGGCTCCTCCGTGATCTACATGGTGCAGCTGCCTATCTTCGGCGTGATCGACACCCCTTGC

TGGATCGTGAAGGCCGCTCCTAGCTGCTCTGAGAAGAAGGGCAACTACGCCTGCCTGCTGAGAGAGGA

CCAAGGCTGGTACTGTCAGAACGCCGGCTCCACCGTGTACTACCCCAACGAGAAGGACTGCGAGACAA

GAGGCGACCACGTGTTCTGCGATACCTGCGCTGGCATCAATGTGGCCGAGCAGTCCAAAGAGTGCAAC

ATCAACATCTCCACCACCAACTATCCCTGCAAGGTGTCCACCGGCAGGCACCCTATTTCCATGGTGGC

TCTGTCTCCACTGGGCGCCCTGGTGGCTTGTTATAAGGGCGTGTCCTGCTCCATCGGCTCCAACAGAG

TGGGCATCATCAAGCAGCTGAACAAGGGCTGCAGCTACATCACCAACCAGGACGCCGATACCGTGACC

ATCGACAATACCGTGTATCAGCTGTCCAAGGTGGAAGGCGAGCAGCACGTGATCAAGGGCAGACCTGT

GTCCTCCAGCTTCGACCCCGTGAAGTTCCCTGAGGATCAGTTCAACGTGGCCCTGGACCAGGTGTTCG

AGTCCATCGAGAACTCTCAGGCTCTGGTGGACCAGTCCAACCGGATTCTGTCTGCCGGCTACATCCCC

GAGGCTCCTAGAGATGGACAGGCCTACGTCAGAAAGGACGGCGAATGGGTGCTGCTGTCTACCTTTCT

CGGAGGCCTGGTGCCTAGAGGCTCTCACCACCATCATCACCACTCCGCTTGGTCCCATCCACAGTTCG

AGAAGTGA

L7F_A1_31 coding nucleotide sequence, codon optimized

SEQ ID NO: 21

ATGTCTTGGAAGGTGGTCATCATCTTCTCCCTGCTGATCACCCCTCAGCACGGCCTGAAAGAGTCCTA

CCTGGAAGAGAGCTGCTCCACCATCACCGAGGGCTACCTGTCTGTGCTGAGAACCGGCTGGTACACCA

ACGTGTTCATGCTGGAAGTGGGCGACGTGGAAAACCTGACCTGTGCTGATGGCCCCAGCCTGCTGAAA

-continued

ACAGAGCTGGACCTGACCAAGAGCGCCCTGAGAAATCTGAGGACCGTGTCTGCCGATCAGCTGGCCAG

AGAGGAACAGATCGAGCAGCCTAGACAGTCCGGATGTGGTGCTGGTGCTACAGCTGGCGTGGCCATTG

CCAAGACCATCCGGCTGGAATCTGAAGTGACCGCCATCAAGAATGCCCTGAAAAAGACCAACGAGGCC

GTGTCTACCCTCGGCAATGGCGTTAGAGTGCTGGCCACAATGGTCCGAGAGCTGAAGGACTTCGTGTC

CAAGAACCTGACCAGGGCCATCAACAAGAACAAGTGTGATATCGCCGACCTGAAGATGGCCGTGTCCT

TTAGCCAGTTCAACCGGCGGTTCCTGAACGTCGTGCGGCAGTTCTCTGATAACGCCGGCATCACCCCT

GCCATCAGCCTGGATCTGATGACCGATGCCGAGCTGGCTAGAGCCGTGTCCAACATGCCTACCTCTGC

CGGCCAGATCAAGCTGATGCTCGAGAACAGAGCTATGGTCCGACGGAAAGGCTTCGGCATCCTGATCG

GCGTGTACGGCTCCTCCGTGATCTACATGGTGCAGCTGCCTATCTTCGGCGTGATCGACACCCCTTGC

TGGATCGTGAAGGCCGCTCCTAGCTGCTCTGAGAAGAAGGGCAACTACGCCTGCCTGCTGAGAGAGGA

CCAAGGCTGGTACTGTCAGAACGCCGGCTCCACCGTGTACTACCCCAACGAGAAGGACTGCGAGACAA

GAGGCGACCACGTGTTCTGCGATACCTGCGCTGGCATCAATGTGGCCGAGCAGTCCAAAGAGTGCAAC

ATCAACATCTCCACCACCAACTATCCCTGCAAGGTGTCCACCGGCAGGCACCCTATTTCCATGGTGGC

TCTGTCTCCACTGGGCGCCCTGGTGGCTTGTTATAAGGGCGTGTCCTGCTCCATCGGCTCCAACAGAG

TGGGCATCATCAAGCAGCTGAACAAGGGCTGCAGCTACATCACCAACCAGGACGCCGATACCGTGACC

ATCGACAATACCGTGTATCAGCTGTCCAAGGTGGAAGGCGAGCAGCACGTGATCAAGGGCAGACCTGT

GTCCTCCAGCTTCGACCCCGTGAAGTTCCCTGAGGATCAGTTCAACGTGGCCCTGGACCAGGTGTTCG

AGTCCATCGAGAACTCTCAGGCTCTGGTGGACCAGTCCAACCGGATTCTGTCTGCCGGCTACATCCCC

GAGGCTCCTAGAGATGGACAGGCCTACGTCAGAAAGGACGGCGAATGGGTGCTGCTGTCTACCTTTCT

CGGAGGCCTGGTGCCTAGAGGCTCTCACCACCATCATCACCACTCCGCTTGGTCCCATCCTCAGTTCG

AGAAGTGA

L7F_A1_33 coding nucleotide sequence, codon optimized

SEQ ID NO: 22

ATGTCTTGGAAGGTGGTCATCATCTTCTCCCTGCTGATCACCCCTCAGCACGGCCTGAAAGAGTCCTA

CCTGGAAGAGAGCTGCTCCACCATCACCGAGGGCTACCTGTCTGTGCTGAGAACCGGCTGGTACACCA

ACGTGTTCATGCTGTGTGTGGGCGACGTGGAAAACCTGACCTGTGCTGATGGCCCCAGCCTGCTGAAA

ACAGAGCTGGACCTGACCAAGAGCGCCCTGAGAGAACTGAGGACCGTGTCTGCAGATCAGCTGGCCAG

AGAGGAACAGATCGAGCAGCCTAGACAGTCCGGATGTGGTGCTGGTGCTACAGCTGGCGTGGCCATTG

CCAAGACCATCCGGCTGGAATCTGAAGTGACCGCCATCAAGAATGCCCTGAAAAAGACCAACGAGGCC

GTGTCTACCCTCGGCAATGGCGTTAGAGTGCTGGCCACAATGGTCCGAGAGCTGTGCGACTTCGTGTC

CAAGAATCTGACCCGGGCCATCAACAAGAACAAGTGTGATATCGCCGACCTGAAGATGGCCGTGTCCT

TCAGCCAGTTCAACCGGCGGTTCCTGAATGTCGTGCGGCAGTTCTCTGACAACGCCGGCATCACCCCT

GCCATCAGCCTGGATCTGATGACCGATGCCGAGCTGGCTAGAGCCGTGTCCAACATGCCTACCTCTGC

CGGCCAGATCAAGCTGATGCTCGAGAACAGAGCTATGGTCCGACGGAAAGGCTTCGGCTTCCTGATCG

GCGTGTACGGCTCTGACGTGATCTACATGGTGCAGCTGCCTATCTTCGGCGTGATCGACACCCCTTGC

TGGATCGTGAAGGCCGCTCCTAGCTGCTCTGAGAAGAAGGGCAACTACGCCTGCCTGCTGAGAGAGGA

CCAAGGCTGGTACTGTCAGAACGCCGGCTCCACCGTGTACTACCCCAACGAGAAGGACTGCGAGACAA

GAGGCGACCACGTGTTCTGCGATACCTGCGCTGGCATCAATGTGGCCGAGCAGTCCAAAGAGTGCAAC

ATCAACATCTCCACCACCAACTATCCCTGCAAGGTGTCCACCGGCAGACACCCCATTTCCATGGTGGC

TCTGTCTCCACTGGGTGCCCTGGTGGCTTGTTATAAGGGCGTGTCCTGCTCCATCGGCTCCAACAGAG

TGGGCATCATCAAGCAGCTGAACAAGGGCTGCAGCTACATCACCAACCAGGACGCCGATACCGTGACC

-continued

ATCGACAATACCGTGTATCAGCTGTCCAAGGTGGAAGGCGAGCAGCACGTGATCAAGGGCAGACCTGT

GTCCTCCAGCTTCGACCCCGTGAAGTTCCCTGAGGATCAGTTCAACGTGGCCCTGGACCAGGTGTTCG

AGTCCATCGAGAACTCTCAGGCTCTGGTGGACCAGTCCAACAGATGCTGTTCCGCCGGCTACATCCCC

GAGGCTCCTAGAGATGGACAGGCCTACGTCAGAAAGGACGGCGAATGGGTGCTGCTGTCTACCTTTCT

CGGAGGCCTGGTGCCTAGAGGCTCTCACCACCATCATCACCACTCCGCTTGGTCCCATCCACAGTTCG

AGAAGTGA

L7F_A1_4.2 coding nucleotide sequence, codon optimized

SEQ ID NO: 23

ATGTCTTGGAAGGTGGTCATCATCTTCTCCCTGCTGATCACCCCTCAGCACGGCCTGAAAGAGTCCTA

CCTGGAAGAGAGCTGCTCCACCATCACCGAGGGCTACCTGTCTGTGCTGAGAACCGGCTGGTACACCA

ACGTGTTCATGCTGGAAGTGGGCGACGTGGAAAACCTGACCTGTGCTGATGGCCCCAGCCTGATCAAG

ACCGAGCTGGACCTGACCAAGTCTGCCCTGAGAGAACTGAGGACCGTGTCTGCCGATCAGCTGGCCAG

AGAGGAACAGATCGAGCAGCCTAGACAGTCCGGATGTGGTGCTGGTGCTACAGCTGGCGTGGCCATTG

CCAAGACCATCCGGCTGGAATCTGAAGTGACCGCCTGGAAGAACGCCCTGAAAAAGACCAACGAGGTG

GTGTCTACCCTCGGCAACGGCGTCAGAGTGCTGGTCACAATGGTCCGAGAGCTGAAGGACTTCGTGTC

CAAGAACCTGACCAGGGCTCTGAACAAGAACAAGTGTGATATCGCCGACCTGAAGATGGCCGTGTCTT

TCAGCCAGTTCAACCGGCGGTTCCTGAACGTCGTGCGGCAGTTCTCTGATAACGCCGGCATCACCCCT

GCCATCAGCCTGGATCTGATGACCGATGCCGAGCTGGCTAGAGCCGTGTCCAACATGCCTACCTCTGC

CGGCCAGATCAAGCTGATGCTGGAAAACAGAGCCATGGTCCGACGGAAAGGCTTCGGCTTTCTGATCG

GCGTGTACGGCTCCTCCGTGATCTACATGGTGCAGCTGCCTATCTTCGGCGTGATCGACACCCCTTGC

TGGATCGTGAAGGCCGCTCCTAGCTGCTCTGAGAAGAAGGGCAACTACGCCTGCCTGCTGAGAGAGGA

CCAAGGCTGGTACTGTCAGAACGCCGGCTCCACCGTGTACTACCCCAACGAGAAGGACTGCGAGACAA

GAGGCGACCACGTGTTCTGCGATACCTGCGCTGGCATCAATGTGGCCGAGCAGTCCAAAGAGTGCAAC

ATCAACATCTCCACCACCAACTATCCCTGCAAGGTGTCCACCGGCAGGCACCCTATTTCCATGGTGGC

TCTGTCTCCACTGGGCGCCCTGGTGGCTTGTTATAAGGGCGTGTCCTGCTCCATCGGCTCCAACAGAG

TGGGCATCATCAAGCAGCTGAACAAGGGCTGCAGCTACATCACCAACCAGGACGCCGATACCGTGACC

ATCGACAATACCGTGTATCAGCTGTCCAAGGTGGAAGGCGAGCAGCACGTGATCAAGGGCAGACCTGT

GTCCTCCAGCTTCGACCCCGTGAAGTTCCCTGAGGATCAGTTCAACGTGGCCCTGGACCAGGTGTTCG

AGTCCATCGAGAACTCTCAGGCTCTGGTGGACCAGTCCAACCGGATCCTGTCCTCTGCCGAGTCTGCT

ATCGGCGGCTATATCCCCGAGGCTCCTAGAGATGGCCAGGCCTATGTTCGGAAGGATGGCGAATGGGT

GCTGCTGTCTACCTTCCTCGGAGGCCTGGTGCCTAGAGGCTCTCACCACCATCATCACCACTCCGCTT

GGTCCCATCCACAGTTCGAGAAGTGA sF_A1_K_L7 mature protein sequence without purification tags

SEQ ID NO: 24

LKESYLEESCSTITEGYLSVLRTGWYTNVFTLEVGDVENLTCADGPSLIKTELDLTKSALRELRTVSA

DQLAREEQIEQPRQSGCGAGATAGVAIAKTIRLESEVTAIKNALKKTNEAVSTLGNGVRVLAFAVREL

KDFVSKNLTRALNKNKCDIADLKMAVSFSQFNRRFLNVVRQFSDNAGITPAISLDLMTDAELARAVSN

MPTSAGQIKLMLENRAMVRRKGFGFLIGVYGSSVIYMVQLPIFGVIDTPCWIVKAAPSCSEKKGNYAC

LLREDQGWYCQNAGSTVYYPNEKDCETRGDHVFCDTCAGINVAEQSKECNINISTTNYPCKVSTGRHP

ISMVALSPLGALVACYKGVSCSIGSNRVGIIKQLNKGCSYITNQDADTVTIDNTVYQLSKVEGEQHVI

KGRPVSSSFDPVKFPEDQFNVALDQVFESIENSQALVDQSNRILSSAESAIGGYIPEAPRDGQAYVRK

DGEWVLLSTFL

L7F_A1_23 mature protein sequence without purification tags

-continued

SEQ ID NO: 25
LKESYLEESCSTITEGYLSVLRTGWYTNVFTLEVGDVENLTCADGPSLIKTELDLTKSALRELRTVSA

DQLAREEQIEQPRQSGCGAGATAGVAIAKTIRLESEVTAIKNALKKTNEAVSTLGNGVRVLATAVREL

KDFVSKNLTRAINKNKCDIADLKMAVSFSQFNRRFLNVVRQFSDNAGITPAISLDLMTDAELARAVSN

MPTSAGQIKLMLENRAMVRRKGFGFLIGVYGSSVIYMVQLPIFGVIDTPCWIVKAAPSCSEKKGNYAC

LLREDQGWYCQNAGSTVYYPNEKDCETRGDHVFCDTCAGINVAEQSKECNINISTTNYPCKVSTGRHP

ISMVALSPLGALVACYKGVSCSIGSNRVGIIKQLNKGCSYITNQDADTVTIDNTVYQLSKVEGEQHVI

KGRPVSSSFDPVKFPEDQFNVALDQVFESIENSQALVDQSNRILSAGYIPEAPRDGQAYVRKDGEWVL

LSTFL

L7F_A1_31 mature protein sequence without purification tags

SEQ ID NO: 26
LKESYLEESCSTITEGYLSVLRTGWYTNVFMLEVGDVENLTCADGPSLLKTELDLTKSALRNLRTVSA

DQLAREEQIEQPRQSGCGAGATAGVAIAKTIRLESEVTAIKNALKKTNEAVSTLGNGVRVLATMVREL

KDFVSKNLTRAINKNKCDIADLKMAVSFSQFNRRFLNVVRQFSDNAGITPAISLDLMTDAELARAVSN

MPTSAGQIKLMLENRAMVRRKGFGILIGVYGSSVIYMVQLPIFGVIDTPCWIVKAAPSCSEKKGNYAC

LLREDQGWYCQNAGSTVYYPNEKDCETRGDHVFCDTCAGINVAEQSKECNINISTTNYPCKVSTGRHP

ISMVALSPLGALVACYKGVSCSIGSNRVGIIKQLNKGCSYITNQDADTVTIDNTVYQLSKVEGEQHVI

KGRPVSSSFDPVKFPEDQFNVALDQVFESIENSQALVDQSNRILSAGYIPEAPRDGQAYVRKDGEWVL

LSTFL

L7F_A1_33 mature protein sequence without purification tags

SEQ ID NO: 27
LKESYLEESCSTITEGYLSVLRTGWYTNVFMLCVGDVENLTCADGPSLLKTELDLTKSALRELRTVSA

DQLAREEQIEQPRQSGCGAGATAGVAIAKTIRLESEVTAIKNALKKTNEAVSTLGNGVRVLATMVREL

CDFVSKNLTRAINKNKCDIADLKMAVSFSQFNRRFLNVVRQFSDNAGITPAISLDLMTDAELARAVSN

MPTSAGQIKLMLENRAMVRRKGFGFLIGVYGSDVIYMVQLPIFGVIDTPCWIVKAAPSCSEKKGNYAC

LLREDQGWYCQNAGSTVYYPNEKDCETRGDHVFCDTCAGINVAEQSKECNINISTTNYPCKVSTGRHP

ISMVALSPLGALVACYKGVSCSIGSNRVGIIKQLNKGCSYITNQDADTVTIDNTVYQLSKVEGEQHVI

KGRPVSSSFDPVKFPEDQFNVALDQVFESIENSQALVDQSNRCCSAGYIPEAPRDGQAYVRKDGEWVL

LSTFL

L7F_A1_4.2 mature protein sequence without purification tags

SEQ ID NO: 28
LKESYLEESCSTITEGYLSVLRTGWYTNVFMLEVGDVENLTCADGPSLIKTELDLTKSALRELRTVSA

DQLAREEQIEQPRQSGCGAGATAGVAIAKTIRLESEVTAWKNALKKTNEVVSTLGNGVRVLVTMVREL

KDFVSKNLTRALNKNKCDIADLKMAVSFSQFNRRFLNVVRQFSDNAGITPAISLDLMTDAELARAVSN

MPTSAGQIKLMLENRAMVRRKGFGFLIGVYGSSVIYMVQLPIFGVIDTPCWIVKAAPSCSEKKGNYAC

LLREDQGWYCQNAGSTVYYPNEKDCETRGDHVFCDTCAGINVAEQSKECNINISTTNYPCKVSTGRHP

ISMVALSPLGALVACYKGVSCSIGSNRVGIIKQLNKGCSYITNQDADTVTIDNTVYQLSKVEGEQHVI

KGRPVSSSFDPVKFPEDQFNVALDQVFESIENSQALVDQSNRILSSAESAIGGYIPEAPRDGQAYVRK

DGEWVLLSTFL

Foldon-glyc-1

SEQ ID NO: 29
GYIPEAPRNGTAYVRKDGEWVLLSTFL

Foldon-glyc-2

SEQ ID NO: 30
GYIPEAPRDGQAYVRKNGTWVLLSTFL

Foldon-glyc-3

SEQ ID NO: 31

-continued

GYIPEAPRDGQAYVRKDGNWTLLSTFL

Foldon-glyc-4

SEQ ID NO: 32

GYIPEAPRNGTAYVRKNGTWVLLSTFL

Foldon-glyc-5

SEQ ID NO: 33

GYIPEAPRNGTAYVRKDGNWTLLSTFL

Trimerization helper VSL motif

SEQ ID NO: 34

ILSA

Trimerization helper VSA motif

SEQ ID NO: 35

CCSA

SEQ ID NO: 36

CCKQTNECCKNLERAVSA

SEQ ID NO: 37

CCRELKECCKNLENAVSA

SEQ ID NO: 38

CCRELKDCCKNLENAVSA

SEQ ID NO: 39

CCRELKDCCKNLERAVSA

SEQ ID NO: 40

CCRELKDCCKQLNKAVSA

SEQ ID NO: 41

CCRELKECCKQLNKAVSA

Thrombin-cleavage site

SEQ ID NO: 42

LVPRGS

TEV-cleavage site

SEQ ID NO: 43

ENLYFQG

Factor Xa cleavage site

SEQ ID NO: 44

IEGR

SEQ ID NO: 45

CCKQTNECCKNLERAVS

SEQ ID NO: 46

CCKQTNECCKNLERAVS

SEQ ID NO: 47

CCKQTNECCKNLERAVS

SEQ ID NO: 48

CCRELKECCKNLENAVS

SEQ ID NO: 49

CCRELKECCKNLENAVS

SEQ ID NO: 50

CCRELKECCKNLENAVS sF_A1_K-E294 protein sequence with substitutions A113C, A339C, T160F, I177L and trimerization helper KLL

SEQ ID NO: 51

MSWKVVIIFSLLITPQHGLKESYLEESCSTITEGYLSVLRTGWYTNVFTLEVGDVENLTCADGPSLIK

TELDLTKSALRELRTVSADQLAREEQIENPRQSRFVLGAIALGVCTAAAVTAGVAIAKTIRLESEVTA

IKNALKKTNEAVSTLGNGVRVLAFAVRELKDFVSKNLTRALNKNKCDIADLKMAVSFSQFNRRFLNVV

RQFSDNAGITPAISLDLMTDAELARAVSNMPTSAGQIKLMLENRAMVRRKGFGFLIGVYGSSVIYMVQ

LPIFGVIDTPCWIVKAAPSCSEKKGNYACLLREDQGWYCQNAGSTVYYPNEKDCETRGDHVFCDTACG

INVAEQSKECNINISTTNYPCKVSTGRHPISMVALSPLGALVACYKGVSCSIGSNRVGIIKQLNKGCS

-continued

YITNQDADTVTIDNTVYQLSKVEGEQHVIKGRPVSSSFDPVKFPEDQFNVALDQVFESIENSQALVDQ

SNRILSSAESAIGGYIPEAPRDGQAYVRKDGEWVLLSTFLGGLVPRGSHHHHHHSAWSHPQFEK sF_A1_K-E294 coding nucleotide sequence, codon optimized

SEQ ID NO: 52

ATGTCTTGGAAGGTGGTCATCATCTTCTCCCTGCTGATCACCCCTCAGCACGGCCTGAAAGAGTCCTA

CCTGGAAGAGAGCTGCTCCACCATCACCGAGGGCTACCTGTCTGTGCTGAGAACCGGCTGGTACACCA

ACGTGTTCACCCTGGAAGTGGGCGACGTGGAAAACCTGACCTGTGCTGATGGCCCCAGCCTGATCAAG

ACCGAGCTGGACCTGACCAAGTCTGCCCTGAGAGAACTGAGGACCGTGTCTGCCGATCAGCTGGCCAG

AGAGGAACAGATCGAGAACCCTCGGCAGTCCAGATTCGTGCTGGGAGCTATTGCTCTGGGCGTGTGTA

CAGCCGCTGCTGTGACAGCTGGTGTCGCTATCGCCAAGACCATCCGGCTGGAATCTGAAGTGACCGCC

ATCAAGAACGCCCTGAAAAAGACCAACGAGGCCGTGTCCACACTCGGCAATGGCGTTAGAGTGCTGGC

CTTTGCTGTGCGCGAGCTGAAGGACTTCGTGTCCAAGAACCTGACCAGGGCTCTGAACAAGAACAAGT

GTGATATCGCCGACCTGAAGATGGCCGTGTCTTTCAGCCAGTTCAACCGGCGGTTCCTGAACGTCGTG

CGGCAGTTCTCTGATAACGCCGGCATCACCCCTGCCATCAGCCTGGATCTGATGACCGATGCCGAGCT

GGCTAGAGCCGTGTCTAACATGCCTACCTCTGCCGGCCAGATCAAGCTGATGCTGGAAAACAGAGCCA

TGGTCCGACGGAAAGGCTTCGGCTTTCTGATCGGCGTGTACGGCTCCTCCGTGATCTACATGGTGCAG

CTGCCTATCTTCGGCGTGATCGACACCCCTTGCTGGATCGTGAAGGCCGCTCCTAGCTGCTCTGAGAA

GAAGGGCAACTACGCCTGCCTGCTGAGAGAGGACCAAGGCTGGTACTGTCAGAACGCCGGCTCCACCG

TGTACTACCCCAACGAGAAGGACTGCGAGACAAGAGGCGACCACGTGTTCTGCGATACCGCCTGTGGC

ATCAATGTGGCCGAGCAGTCCAAAGAGTGCAACATCAACATCTCCACCACCAACTATCCCTGCAAGGT

GTCCACCGGCAGGCACCCTATTTCCATGGTGGCTCTGTCTCCACTGGGCGCCCTGGTGGCTTGTTATA

AGGGCGTGTCCTGCTCCATCGGCTCCAACAGAGTGGGCATCATCAAGCAGCTGAACAAGGGCTGCAGC

TACATCACCAACCAGGACGCCGATACCGTGACCATCGACAATACCGTGTATCAGCTGTCCAAGGTGGA

AGGCGAGCAGCACGTGATCAAGGGCAGACCTGTGTCCTCCAGCTTCGACCCCGTGAAGTTCCCTGAGG

ATCAGTTCAACGTGGCCCTGGACCAGGTGTTCGAGTCCATCGAGAACTCTCAGGCTCTGGTGGACCAG

TCCAACCGGATCCTGTCCTCTGCCGAGTCTGCTATCGGCGGCTATATCCCCGAGGCTCCTAGAGATGG

CCAGGCCTATGTTCGGAAGGATGGCGAATGGGTGCTGCTGTCTACCTTCCTCGGAGGCCTGGTGCCTA

GAGGCTCTCACCACCATCATCACCACTCCGCTTGGTCCCATCCACAGTTCGAGAAGTGA sF_A1_MFur protein sequence with deletion of amino acids at positions 103 to 111, replacement of R102 by a furin site KKRKRR and the substitution G294E, stabilized in post-fusion conformation

SEQ ID NO: 53

MSWKVVIIFSLLITPQHGLKESYLEESCSTITEGYLSVLRTGWYINVFTLEVGDVENLTCADGPSLIK

TELDLTKSALRELRTVSADQLAREEQIENPRQSKKRKRRVATAAAVTAGVAIAKTIRLESEVTAIKNA

LKKTNEAVSTLGNGVRVLATAVRELKDFVSKNLTRAINKNKCDIADLKMAVSFSQFNRRFLNVVRQFS

DNAGITPAISLDLMTDAELARAVSNMPTSAGQIKLMLENRAMVRRKGFGFLIGVYGSSVIYMVQLPIF

GVIDTPCWIVKAAPSCSEKKGNYACLLREDQGWYCQNAGSTVYYPNEKDCETRGDHVFCDTAAGINVA

EQSKECNINISTTNYPCKVSTGRHPISMVALSPLGALVACYKGVSCSIGSNRVGIIKQLNKGCSYITN

QDADTVTIDNTVYQLSKVEGEQHVIKGRPVSSSFDPVKFPEDQFNVALDQVFESIENSQALVDQSNRI

LSSAEKGNTSGRENLYFQGGGGSGYIPEAPRDGQAYVRKDGEWVLLSTFLGGIEGRHHHHHH sF_A1_MFur coding nucleotide sequence, codon optimized

SEQ ID NO: 54

ATGTCCTGGAAGGTCGTGATCATCTTCTCCCTGCTGATCACCCCCCAGCACGGCCTGAAAGAGTCCTA

CCTGGAAGAGAGCTGCTCCACCATCACCGAGGGCTACCTGTCTGTGCTGCGGACCGGCTGGTACACCA

ACGTGTTCACCCTGGAAGTGGGCGACGTGGAAAACCTGACCTGCGCCGATGGCCCCAGCCTGATCAAG

-continued

```
ACCGAGCTGGACCTGACCAAGTCCGCCCTGCGGGAACTGAGAACCGTGTCTGCCGATCAGCTGGCCAG

AGAGGAACAGATCGAGAACCCCCGGCAGTCCAAGAAACGGAAGCGGAGAGTGGCCACCGCCGCTGCTG

TGACAGCTGGCGTGGCCATTGCCAAGACCATCCGGCTGGAATCCGAAGTGACCGCCATCAAGAACGCC

CTGAAAAAGACCAACGAGGCCGTGTCTACCCTGGGCAATGGCGTGCGAGTGCTGGCTACAGCTGTGCG

CGAGCTGAAGGACTTCGTGTCCAAGAACCTGACCCGGGCCATCAACAAGAACAAGTGTGATATCGCCG

ACCTGAAGATGGCCGTGTCCTTTAGCCAGTTCAACCGGCGGTTCCTGAACGTCGTGCGGCAGTTCTCT

GACAACGCCGGCATCACCCCTGCCATCTCCCTGGATCTGATGACCGACGCCGAGCTGGCTAGAGCCGT

GTCCAACATGCCTACCTCTGCCGGCCAGATCAAGCTGATGCTGGAAAACCGGGCCATGGTGCGACGGA

AGGGCTTCGGCTTTCTGATCGGCGTGTACGGCTCCTCCGTGATCTACATGGTGCAGCTGCCTATCTTC

GGCGTGATCGACACCCCCTGCTGGATCGTGAAGGCCGCTCCTAGCTGCTCCGAGAAGAAGGGCAACTA

CGCCTGCCTGCTGAGAGAGGACCAGGGCTGGTACTGTCAGAACGCCGGCTCCACCGTGTACTACCCCA

ACGAGAAGGACTGCGAGACACGGGGCGACCACGTGTTCTGTGATACCGCTGCTGGCATCAACGTGGCC

GAGCAGTCCAAAGAGTGCAACATCAACATCTCCACCACCAACTACCCCTGCAAGGTGTCCACCGGCAG

GCACCCCATCTCTATGGTGGCCCTGTCTCCTCTGGGCGCCCTGGTGGCTTGTTACAAGGGCGTGTCCT

GCTCCATCGGCTCCAACAGAGTGGGCATCATCAAGCAGCTGAACAAGGGCTGCAGCTACATCACCAAC

CAGGACGCCGACACCGTGACCATCGACAATACCGTGTATCAGCTGTCCAAGGTGGAAGGCGAGCAGCA

CGTGATCAAGGGCAGACCCGTGTCCTCCAGCTTCGACCCCGTGAAGTTCCCCGAGGATCAGTTCAATG

TGGCCCTGGACCAGGTGTTCGAGTCCATCGAGAACTCCCAGGCTCTGGTGGACCAGTCCAACCGGATC

CTGTCCTCTGCCGAGAAGGGAAACACCTCCGGCAGAGAGAACCTGTATTTTCAAGGCGGCGGAGGCTC

CGGCTACATCCCTGAGGCTCCTAGAGATGGCCAGGCCTACGTGCGGAAGGATGGCGAATGGGTGCTGC

TGTCCACCTTCCTGGGCGGCATCGAGGGCAGACACCACCATCATCACCACTGA
```

---

The invention claimed is:

1. An immunogenic human metapneumovirus (hMPV) modified F protein or fragment thereof, comprising a recombinant single-chain polypeptide lacking a fusion peptide (FP) and comprising an F2 domain, a heterologous peptide linker and an F1 domain, wherein the linker is positioned between the F2 and F1 domains and contains a cysteine residue which forms a disulfide bond with a non-natural cysteine residue present in the F1 domain, wherein the F2 domain comprises or consists of an amino acid sequence having at least 85%, at least 90%, at least 95% or at least 99% sequence identity to SEQ ID NO: 2, wherein the F1 domain comprises or consists of an amino acid sequence having at least 85%, at least 90%, at least 95% or at least 99% sequence identity to SEQ ID NO: 3 or to residues 17-388 thereof, and wherein:

(a) the F1 domain comprises a cysteine residue substituted at position 236 of SEQ ID NO: 3;

(b) the recombinant single-chain polypeptide comprises a cysteine residue substituted at position 338 relative to the amino acid positions of a native hMPV F protein sequence of SEQ ID NO: 1;

(c) the linker comprises a cysteine residue which forms a disulfide bond with a non-natural cysteine residue substituted at position 236 in the F1 domain of SEQ ID NO: 3; and/or (d) the linker comprises a cysteine residue which forms a disulfide bond with a non-natural cysteine residue substituted at position 338 relative to the amino acid positions of the native hMPV F protein sequence of SEQ ID NO: 1.

2. The immunogenic protein of claim 1, wherein the linker consists of 1 to 5, preferably 5 amino acids, and wherein the cysteine residue is at position 1 or 3, preferably at position 1 of the linker.

3. The immunogenic protein of claim 1, wherein the linker comprises a sequence selected from the group consisting of CGAGA (SEQ ID NO: 4), CGAGV (SEQ ID NO: 57, CGAAV (SEQ ID NO: 58), AGCGA (SEQ ID NO: 59), CAAAV (SEQ ID NO: 60), and CAAFV (SEQ ID NO: 61), preferably CGAGA (SEQ ID NO: 4).

4. The immunogenic protein of claim 1, wherein the single-chain polypeptide further comprises one or more substitution(s) relative to the native hMPV F protein sequence of SEQ ID NO: 1 that stabilize the pre-fusion conformation.

5. The immunogenic protein of claim 1, wherein the single-chain polypeptide comprises one or more substitution(s) selected from the group consisting of T49M, E51C, E80N, I137W, A147V, A159V, T160F, A161M, K166C, I67L, I177L, F258I, S266D, I480C and/or L481C relative to the native hMPV F protein sequence of SEQ ID NO: 1.

6. The immunogenic protein of claim 1, wherein the single-chain polypeptide comprises one of the following substitution combinations: N97Q, R102G and G294E; N97Q, R102G, T160F, I177L and G294E; T49M, I67L, E80N, N97Q, R102G, A161M, F258I and G294E; T49M, E51C, I67L, N97Q, R102G, A161M, K166C, S266D, G294E, I480C and L481C; or T49M, N97Q, R102G, I137W, A147V, A159V, A161M, I177L and G294E, wherein the positions are relative to the amino acid positions of the native hMPV F protein sequence of SEQ ID NO: 1.

7. The immunogenic protein of claim 1, wherein the single-chain polypeptide comprises a trimerization helper domain (foldon) consisting of the amino acid sequence of SEQ ID NO: 10 or any of SEQ ID NOs 29 to 33, and the amino acid sequence of SEQ ID NO: 34 or SEQ ID NO: 35 upstream of the foldon domain.

8. The immunogenic protein of claim 1, wherein the single-chain polypeptide comprises or consists of the amino acid sequence any of SEQ ID NOs: 5 to 9 or 24 to 28.

9. An immunogenic composition or vaccine comprising the immunogenic protein of claim 1.

10. An immunogenic composition or vaccine comprising the immunogenic protein of claim 1, wherein said immunogenic protein comprises or consists of the amino acid sequence as set forth in SEQ ID NO: 5 or SEQ ID NO: 25 (L7F_A1_23), or a variant thereof having at least 85%, 90%, 95%, 98% or 99% sequence identity thereto.

11. An immunogenic composition or vaccine comprising the immunogenic protein of claim 1, wherein said immunogenic protein comprises or consists of the amino acid sequence as set forth in as set forth in SEQ ID NO: 6 or SEQ ID NO: 24 (sF_A1_K_L7), or a variant thereof having at least 85%, 90%, 95%, 98% or 99% sequence identity thereto.

12. An immunogenic composition or vaccine comprising the immunogenic protein of claim 1, wherein said immunogenic protein comprises or consists of the amino acid sequence as set forth in as set forth in SEQ ID NO: 7 or SEQ ID NO: 26 (L7F_A1_31), or a variant thereof having at least 85%, 90%, 95%, 98% or 99% sequence identity thereto.

13. An immunogenic composition or vaccine comprising the immunogenic protein of claim 1, wherein said immunogenic protein comprises or consists of the amino acid sequence as set forth in SEQ ID NO: 8 or SEQ ID NO: 27 (L7F_A1_33), or a variant thereof having at least 85%, 90%, 95%, 98% or 99% sequence identity thereto.

14. An immunogenic composition or vaccine comprising the immunogenic protein of claim 1, wherein said immunogenic protein comprises or consists of the amino acid sequence as set forth in SEQ ID NO: 9 or SEQ ID NO: 28 (L7F_A1_4.2), or a variant thereof having at least 85%, 90%, 95%, 98% or 99% sequence identity thereto.

15. A method for generating an immune response against hMPV comprising administering to a human subject an effective amount of the immunogenic protein of claim 1 or immunogenic composition comprising said immunogenic protein.

16. A method for treating or preventing a respiratory tract infection in a human subject comprising administering to the subject an effective amount of the immunogenic protein of claim 1 or immunogenic composition comprising the immunogenic protein of claim 1.

17. A method for producing the immunogenic protein of claim 1, wherein said method comprises expressing the immunogenic protein from a nucleic acid molecule of any of the sequences of SEQ ID NOs: 19 to 23 or a nucleic acid molecule having at least 85%, 90%, 95%, 98% or 99% sequence identity to any of SEQ ID NOs: 19 to 23.

18. The method of claim 17, further comprising combining the expressed protein with a pharmaceutically acceptable carrier and/or excipient.

19. The immunogenic composition or vaccine of claim 9, further comprising a pharmaceutically acceptable carrier and/or excipient.

20. The immunogenic composition or vaccine of claim 9, further comprising an adjuvant.

* * * * *